US011472894B2

(12) United States Patent
Matyjaszewski et al.

(10) Patent No.: US 11,472,894 B2
(45) Date of Patent: Oct. 18, 2022

(54) ENZYME-ASSISTED ATRP PROCEDURES

(71) Applicant: Carnegie Mellon University, Pittsburgh, PA (US)

(72) Inventors: Krzysztof Matyjaszewski, Pittsburgh, PA (US); Alan Enciso Barros, Pittsburgh, PA (US); Liye Fu, Pittsburgh, PA (US); Alan J. Russell, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 321 days.

(21) Appl. No.: 16/520,008

(22) Filed: Jul. 23, 2019

(65) Prior Publication Data

US 2020/0024372 A1  Jan. 23, 2020

Related U.S. Application Data

(60) Provisional application No. 62/764,221, filed on Jul. 23, 2018.

(51) Int. Cl.
| | |
|---|---|
| *C08F 4/10* | (2006.01) |
| *C08F 2/16* | (2006.01) |
| *C08K 5/1545* | (2006.01) |
| *C08F 4/26* | (2006.01) |
| *C12P 7/00* | (2006.01) |
| *C08F 220/28* | (2006.01) |

(52) U.S. Cl.
CPC .............. *C08F 4/10* (2013.01); *C08F 2/16* (2013.01); *C08F 4/26* (2013.01); *C08K 5/1545* (2013.01); *C12P 7/00* (2013.01); *C08F 220/28* (2013.01); *C08F 220/286* (2020.02); *C08F 2438/01* (2013.01); *C12Y 101/03004* (2013.01); *C12Y 111/01007* (2013.01)

(58) Field of Classification Search
CPC .... C08F 2438/01; C08F 220/286; C08F 4/10; C08F 4/26; C08F 2/16; C08F 220/28; C08F 2/38; C12P 7/00; C12P 13/02; C12Y 111/01007; C12Y 101/03004; C08K 5/1545

See application file for complete search history.

(56) References Cited

U.S. PATENT DOCUMENTS

| | | | |
|---|---|---|---|
| 3,424,839 | A | 1/1969 | Montandraud et al. |
| 4,350,801 | A | 9/1982 | Grasshoff |
| 5,639,633 | A | 6/1997 | Callstrom et al. |
| 5,763,546 | A | 6/1998 | Jung et al. |
| 5,789,487 | A | 8/1998 | Matyjaszewski et al. |
| 5,807,937 | A | 9/1998 | Matyjaszewski et al. |
| 5,998,588 | A | 2/1999 | Hoffman et al. |
| 5,945,491 | A | 8/1999 | Matyjaszewski et al. |
| 6,111,022 | A | 8/2000 | Matyjaszewski et al. |
| 6,121,371 | A | 9/2000 | Matyjaszewski et al. |
| 6,124,411 | A | 9/2000 | Matyjaszewski et al. |
| 6,162,882 | A | 12/2000 | Matyjaszewski et al. |
| 6,291,200 | B1 | 9/2001 | LeJeune et al. |
| 6,407,187 | B1 | 6/2002 | Matyjaszewski et al. |
| 6,512,060 | B1 | 1/2003 | Matyjaszewski et al. |
| 6,538,091 | B1 | 3/2003 | Matyjaszewski et al. |
| 6,541,580 | B1 | 4/2003 | Matyjaszewski et al. |
| 6,624,262 | B2 | 9/2003 | Matyjaszewski et al. |
| 6,624,263 | B2 | 9/2003 | Matyjaszewski et al. |
| 6,627,314 | B2 | 9/2003 | Matyjaszewski et al. |
| 6,642,037 | B2 | 11/2003 | Gordon et al. |
| 6,759,220 | B1 | 7/2004 | LeJeune et al. |
| 6,759,491 | B2 | 7/2004 | Matyjaszewski et al. |
| 6,790,919 | B2 | 9/2004 | Matyjaszewski et al. |
| 6,887,962 | B2 | 5/2005 | Matyjaszewski et al. |
| 7,019,082 | B2 | 3/2006 | Matyjaszewski et al. |
| 7,049,373 | B2 | 5/2006 | Matyjaszewski et al. |
| 7,064,166 | B2 | 6/2006 | Matyjaszewski et al. |
| 7,125,938 | B2 | 10/2006 | Matyjaszewski et al. |
| 7,157,530 | B2 | 1/2007 | Matyjaszewski et al. |
| 7,332,550 | B2 | 2/2008 | Matyjaszewski et al. |
| 7,407,995 | B2 | 8/2008 | Ok et al. |
| 7,572,764 | B2 | 8/2009 | Cohen et al. |
| 7,572,874 | B2 | 8/2009 | Matyjaszewski et al. |
| 7,678,869 | B2 | 3/2010 | Matyjaszewski et al. |
| 7,722,838 | B2 | 5/2010 | Hyacinthe |
| 7,795,355 | B2 | 9/2010 | Matyjaszewski et al. |
| 7,825,199 | B1 | 11/2010 | Matyjaszewski et al. |
| 7,893,173 | B2 | 2/2011 | Matyjaszewski et al. |
| 7,893,174 | B2 | 2/2011 | Matyjaszewski et al. |
| 8,252,880 | B2 | 8/2012 | Matyjaszewski et al. |
| 8,273,823 | B2 | 9/2012 | Matyjaszewski et al. |
| 8,349,410 | B2 | 1/2013 | Huang et al. |

(Continued)

FOREIGN PATENT DOCUMENTS

| | | |
|---|---|---|
| CN | 103451174 | 12/2013 |
| EP | 0136728 | 4/1985 |

(Continued)

OTHER PUBLICATIONS

Averick et al., "Solid-Phase Incorporation of an ATRP Initiator for Polymer-DNA Biohybrids", Angew. Chem. Int. Ed. 2014, vol. 53, pp. 2739-2744. (Year: 2014).*

Zavada et al., "Radical-Mediated Enzymatic Polymerizations", Int. J. Mol. Sci., 2016,17, 195; (total pp. 1-27); (doi:10.3390/ijms17020195) (Year: 2016).*

Abzalimov et al., "Structural characterization of protein-polymer conjugates. I. Assessing heterogeneity of a small PEGylated protein and mapping conjugation sites using ion exchange chromatography and top-down tandem mass spectrometry," International Journal of Mass Spectrometry, 2012, 312: 135-143.

Axelsen et al., "Structure and dynamics of the active site gorge of acetylcholinesterase: Synergistic use of molecular dynamics simulation and X-ray crystallography," Protein Science, 1994, 3(2): 188-197.

(Continued)

*Primary Examiner* — Satyendra K Singh
(74) *Attorney, Agent, or Firm* — Fish & Richardson P.C.

(57) ABSTRACT

Materials and methods for conducting an atom transfer radical polymerization in the presence of oxygen by interlocking enzymatic activities are provided herein.

18 Claims, 18 Drawing Sheets

(56) References Cited

U.S. PATENT DOCUMENTS

| | | |
|---|---|---|
| 8,367,051 B2 | 2/2013 | Matyjaszewski et al. |
| 8,404,788 B2 | 3/2013 | Matyjaszewski et al. |
| 8,445,610 B2 | 5/2013 | Matyjaszewski et al. |
| 8,816,001 B2 | 8/2014 | Mehl et al. |
| 8,865,795 B1 | 10/2014 | Xin et al. |
| 8,865,797 B2 | 10/2014 | Matyjaszewski et al. |
| 8,871,831 B2 | 10/2014 | Huang et al. |
| 8,962,764 B2 | 5/2015 | Matyjaszewski et al. |
| 9,243,274 B2 | 1/2016 | Mehl et al. |
| 9,410,020 B2 | 8/2016 | Matyjaszewski et al. |
| 9,447,042 B2 | 9/2016 | Kita et al. |
| 9,533,297 B2 | 1/2017 | Matyjaszewski et al. |
| 9,539,338 B2 | 1/2017 | Russell et al. |
| 9,644,042 B2 | 5/2017 | Matyjaszewski et al. |
| 10,400,232 B2 | 9/2019 | Russell et al. |
| 2004/0152880 A1 | 8/2004 | Minden |
| 2005/0065300 A1 | 3/2005 | Lewandowski et al. |
| 2005/0107277 A1 | 5/2005 | Lin et al. |
| 2007/0123646 A1 | 5/2007 | Lele et al. |
| 2007/0219330 A1 | 9/2007 | Haddleton et al. |
| 2007/0276088 A1 | 11/2007 | Maynard et al. |
| 2007/0287828 A1 | 12/2007 | Minden |
| 2008/0206182 A1 | 8/2008 | Sommermeyer et al. |
| 2009/0095668 A1 | 4/2009 | Busson |
| 2009/0171024 A1 | 7/2009 | Jakubowski et al. |
| 2010/0130721 A1 | 5/2010 | Iwakura et al. |
| 2011/0091957 A1 | 4/2011 | Lele et al. |
| 2012/0213986 A1 | 8/2012 | Kowalewski |
| 2013/0058910 A1 | 3/2013 | Koepsel et al. |
| 2013/0071394 A1 | 3/2013 | Troyer et al. |
| 2013/0131278 A1 | 5/2013 | Huang et al. |
| 2014/0183055 A1 | 7/2014 | Matyjaszewski et al. |
| 2014/0275420 A1 | 9/2014 | Matyjaszewski et al. |
| 2015/0087795 A1 | 3/2015 | Matyjaszewski et al. |
| 2016/0101190 A1 | 4/2016 | Russell et al. |
| 2016/0200840 A1 | 7/2016 | Matyjaszewski et al. |
| 2016/0244741 A1 | 8/2016 | Russell et al. |
| 2017/0113934 A1 | 4/2017 | Kowalewski |
| 2018/0051271 A1 | 2/2018 | Russell et al. |
| 2019/0358335 A1 | 11/2019 | Russell et al. |
| 2020/0369716 A1 | 11/2020 | Murata et al. |
| 2021/0290769 A1 | 9/2021 | Russell et al. |
| 2021/0316001 A1 | 10/2021 | Russell et al. |
| 2021/0388337 A1 | 12/2021 | Murata et al. |

FOREIGN PATENT DOCUMENTS

| | | |
|---|---|---|
| GB | 2215335 | 9/1989 |
| WO | WO 1998/15620 | 4/1998 |
| WO | WO 2002/083708 | 10/2002 |
| WO | WO 2013/028756 | 2/2013 |
| WO | WO 2014/176279 | 10/2014 |
| WO | WO 2015/051326 | 4/2015 |
| WO | WO 2016/130677 | 8/2015 |
| WO | WO 2019/028168 | 2/2019 |
| WO | WO 2020/123023 | 6/2020 |

OTHER PUBLICATIONS

Bhattacharjee et al., "Site-Specific Zwitterionic Polymer Conjugates of a Protein Have Long Plasma Circulation," ChemBioChem, 2015, 16(17):2451-2455.

Browne et al., "A possible three-dimensional structure of bovine α-lactalbumin based on that of hen's egg-white lysozyme," Journal of Molecular Biology, May 1969, 42(1):65-86.

Broyer et al., "Emerging synthetic approaches forprotein-polymerconjugations," Chem. Commun., 2011, 47(8):2212-2226.

Calligari et al., "Adaptation of Extremophilic Proteins with Temperature and Pressure: Evidence from Initiation Factor 6," The Journal of Physical Chemistry B, May 2015, 119(25):7860-7873.

Campbell et al., "Intramolecular Electron Transfer through Poly-Ferrocenyl Glucose Oxidase Conjugates to Carbon Electrodes: 1. Sensor Sensitivity, Selectivity and Longevity," Electrochimica Acta, Sep. 2017, 248:578-584.

Canfield, "The Amino Acid Sequence of Egg White Lysozyme," Journal of Biological Chemistry, Aug. 1963, 228(8)2698-2707.

Cao et al., "Super-hydrophilic zwitterionic poly(carboxybetaine) and amphiphilic non-ionic poly(ethylene glycol) for stealth nanoparticles," Nano Today, Oct. 2012, 7(5):404-413.

Carmali et al., "Polymer-Based Protein Engineering: Synthesis and Characterization of Armored, High Graft Density Polymer-Protein Conjugates.," Methods in Enzymology, 2017, 590: 347-380.

Carmali et al., "Tertiary Structure-Based Prediction of How ATRP Initiators React with Proteins," ACS Biomaterials Science & Engineering, Jul. 2017, 3(9):2086-2097.

Chen et al., "Site-Selective Lysine Modification of Native Proteins and Peptides via Kinetically Controlled Labeling," Bioconjugate Chemistry, Feb. 2012, 23(3):500-508.

Coker, "Extremophiles and biotechnology: current uses and prospects [version 1; peer review: 2 approved]," FI000Research, 2016, 5: 1-7.

Colloc'h et al., "Functional relevance of the internal hydrophobic cavity of urate oxidase," FEBS Letters, May 2014, 588(9): 1715-1719.

Da Silva Freitas et al., "Biochemical and biophysical characterization of lysozyme modified by PEGylation," International Journal of Pharmaceutics, Jun. 2010, 392(1-2): 111-117.

Davis et al., "Statistical, Gradient, Block and Graft Copolymers by Controlled/Living Radical Polymerizations," Advances in Polymer Science, Oct. 2002, 159(1):1-13.

De Champdore et al., "Proteins from extremophiles as stable tools for advanced biotechnological applications of high social interest," Journal of The Royal Society Interface, 2007, 4(13):183-191.

Dill, "Dominant forces in protein folding," Biochemistry, Aug. 1990, 29(31):7133-7155.

Dorovska-Taran et al., "Comparison of the dynamic structure of α-chymotrypsin in aqueous solution and in reversed micelles by fluorescent active-site probing," European Journal of Biochemistry, Jan. 1993, 211(1-2):47-55.

Dvir et al., "Acetylcholinesterase: From 3D structure to function," Chemico-Biological Interactions, Sep. 2010, 187(1-3):10-22.

Dwyer et al., "Computational Design of a Biologically Active Enzyme," Science, Jun. 2004, 304(5679): 1967-1971.

Fersht, "Conformational equilibria in α- and δ-chymotrypsin: The energetics and importance of the salt bridge," Journal of Molecular Biology, Mar. 1972, 64(2):497-509.

Finn, "PEGylation of Human Growth Hormone: Strategies and Properties.," PEGylated Protein Drugs: Basic Science and Clinical Applications, 2009, pp. 187-203.

Foser et al., "Isolation, structural characterization, and antiviral activity of positional isomers of monopegylated interferon α-2a (PEGASYS)," Protein Expression and Purification, Jul. 2003, 30(1):78-87.

Gabison et al., "Structural analysis of urate oxidase in complex with its natural substrate inhibited by cyanide: Mechanistic implications," BMC Structural Biology, Jul. 2008, 8(1):32, 8 pages.

Gao et al., "In situ growth of a PEG-like polymer from the C terminus of an intein fusion protein improves pharmacokinetics and tumor accumulation," Proceedings of the National Academy of Sciences of the USA, 2009, 106(36): 15231-15236.

Gerislioglu et al., "Characterization of singly and multiply PEGylated insulin isomers by reversed-phase ultra-performance liquid chromatography interfaced with ion mobility mass spectrometry," Analytica Chimica Acta, Dec. 2017, 1004:58-66.

Girard et al., "Structure-Function Perturbation and Dissociation of Tetrameric Urate Oxidase by High Hydrostatic Pressure," Biophysical Journal, May 2010, 98(10):2365-2373.

Hollecker et al., "Effect on protein stability of reversing the charge on amino groups," Biochimica et Biophysica Acta (BBA)—Protein Structure and Molecular Enzymology, Mar. 1982, 701(3):395-404.

Huang et al., "Highly Active Biocatalytic Coatings from Protein-Polymer Diblock Copolymers," ACS Applied Materials & Interfaces, Jul. 2015, 7(27): 14660-14669.

(56) References Cited

OTHER PUBLICATIONS

Isom et al., "Large shifts in pKa values of lysine residues buried inside a protein," Proc. Natl. Acad Sci. USA, 2011, 108(13):5260-5265.
Johnson, "The Structure and Function of Lysozyme," Science Progress, Jul. 1966, 54(21):367-385.
Koide et al., "Stabilization of a Fibronectin Type III Domain by the Removal of Unfavorable Electrostatic Interactions on the Protein Surface," Biochemistiy, Aug. 2001, 40(34):10326-10333.
Kovaliov et al., "Synthesis of lipase polymer hybrids with retained or enhanced activity using the grafting-from strategy," Polymer, Feb. 2018, 137:338-345.
Laurents et al., "Charge-Charge Interactions are Key Determinants of the pK Values of Ionizable Groups in Ribonuclease Sa (pI=3.5) and a Basic Variant (pI=10.2)," Journal of Molecular Biology, Jan. 2003, 325(5): 1077-1092.
Le Droumaguet et al., "Recent advances in the design of bioconjugates from controlled/living radical polymerization," Polymer Chemistry, Jul. 2010, 1(5):545-756.
Lee et al., "A Novel Method for Identifying PEGylation Sites of Protein Using Biotinylated PEG Derivatives," Journal of Pharmaceutical Sciences, Jan. 2003, 92(1):97-103.
Lee et al., "Effects of Charge-to-Alanine Substitutions on the Stability of Ribosomal Protein L30e from Thermococcus celer," Biochemistiy, Dec. 2005, 44(51):16817-16825.
Lee et al., "Non-coding RNAs derived from an alternatively spliced REST transcript (REST-003) regulate breast cancer invasiveness," Scientific Reports, Jun. 2015, 5:892.
Levitsky et al., "Reversible conformational transition gives rise to 'zig-zag' temperature dependence of the rate constant of irreversible thermoinactivation of enzymes," European Journal of Biochem. 1994, 219(1-2):219-230.
Li et al., "Protein conjugation of thermoresponsive amine-reactive polymers prepared by RAFT," Polymer Chemistry, 2011, 2(2):323-327.
Liu et al., "Semi-permeable coatings fabricated from comb-polymers efficiently protect proteins in vivo," Nature Communications, Nov. 2014, 5(5526): 1-8.
Loladze et al., "Removal of surface charge-charge interactions from ubiquitin leaves the protein folded and very stable," Protein Science, Jan. 2002, 11(1): 174-177.
Lozano et al., "Dynamic Structure/Function Relationships in the α-Chymotrypsin Deactivation Process by Heat and pH," European Journal of Biochemistry, Aug. 1997, 248(1):80-85.
Lozano et al., "Effect of polyols on α-chymotrypsin thermostability: a mechanistic analysis of the enzyme stabilization," Journal of Biotechnology, Jun. 1994, 35(1):9-18.
Lozano et al., "Stabilization of α-chymotrypsin by ionic liquids in transesterification reactions," Biotechnology and Bioengineering, Dec. 2001, 75(5):563-569.
Matyjaszewski et al., "3.12—Copper-Mediated Atom Transfer Radical Polymerization," Polymer Science: A Comprehensive Reference, 2012; 3:377-428.
Matyjaszewski et al., "Atom Transfer Radical Polymerization," Chemical Reviews, 2001, 101 :2921-2990.
Matyjaszewski et al., "Controlled/"Living" Radical Polymerization. Kinetics of the Homogeneous Atom Transfer Radical Polymerization of Styrene," Journal of the American Chemical Society, Jan. 1997, 119(4):674-680.
Matyjaszewski, "Architecturally Complex Polymers with Controlled Heterogeneity," Science, Aug. 2011, 333(6046):1104-1105.
Mozhaev et al., "Multipoint attachment to a support protects enzyme from inactivation by organic solvents: α-Chymotrypsin in aqueous solutions of alcohols and diols," Biotechnology and Bioengineering, Mar. 1990, 35(7):653-659.
Pace et al., "Forces contributing to the conformational stability of proteins," FASEB Journal, Jan. 1996, 10(1):75-83.
Pace et al., "Forces stabilizing proteins," FEES Letters, Jun. 2014, 588(14):2177-2184.

Paeth et al., "Chapter Nine—Approaches for Conjugating Tailor-Made Polymers to Proteins," Methods in Enzymology, 2017, 590:193-224.
Panganiban et al., "Random heteropolymers preserve protein function in foreign environments," Science, Mar. 2018, 359(6381):1239-1243.
Park et al., "Advances in computational protein design," Current Opinion in Structural Biology, Aug. 2004, 14(4):487-494.
Parrott et al., "Drug Delivery: Relieving PEGylation," Nature Chemistry, Dec. 2011, 4(1):13-14.
PCT International Preliminary Report on Patentability for International Application No. PCT/US2014/035033 dated Oct. 27, 2015.
PCT International Preliminary Report on Patentability in International Application No. PCT/US2019/044723, dated Feb. 2, 2021, 7 pages.
PCT International Preliminary Report on Patentability in International Application No. PCT/US2019/044743, dated Feb. 2, 2021, 7 pages.
PCT International Search Report and Written Opinion in International Application No. PCT/US2019/044723, dated Dec. 5, 2019, 11 pages.
PCT International Search Report and Written Opinion in International Application No. PCT/US2019/044743, dated Oct. 16, 2019, 9 pages.
PCT International Search Report and Written Opinion for International Application No. PCT/US2016/017351 dated, Apr. 21, 2016, 9 pages.
PCT International Search Report and Written Opinion in International Application No. PCT/US2014/035033, dated Aug. 28, 2014.
Peeler et al., "Genetically Encoded Initiator for Polymer Growth from Proteins," Journal of the American Chemical Society, 2010, 132(39): 13575-13577.
Pelegri-Oday et al., "Therapeutic Protein-Polymer Conjugates: Advancing Beyond PEGylation," Journal of the American Chemical Society, Dec. 2014, 136(41):14323-14332.
Perry et al., "PEGylated PRINT Nanoparticles: The Impact of PEG Density on Protein Binding, Macrophage Association, Biodistribution, and Pharmacokinetics," Nano Letters, Aug. 2012, 12(10):5304-5310.
Perutz, "Electrostatic effects in proteins," Science, Sep. 1978, 201(4362): 1187-1191.
Pokala et al., "Review: protein design—where we were, where we are, where we're going," Journal of Structural Biology, 2001, 134(2-3):269-281.
Price et al., "Surface charge measurements on Micrococcus lysodeikticus and the catalytic implications for lysozyme," Biochimica et Biophysica Acta (BBA)—Molecular Cell Research, Nov. 1986, 889(2):128-135.
Radestock et al., "Exploiting the Link between Protein Rigidity and Thermostability for Data-Driven Protein Engineering," Engineering in Life Sciences, Oct. 2008, 8(5):507-522.
Shakya et al., "An update on smart biocatalysts for industrial and biomedical applications," Journal of Royal Society Interface, Febmary 2018, 15(139): 1-15.
Shental-Bechor et al., "Effect of glycosylation on protein folding: A close look at thermodynamic stabilization," PNAS. Jun. 2008, 105(24):8256-8261.
Shoichet et al., "A relationship between protein stability and protein function.," Proc. Natl. Acad Sci. USA, 1995, 92(2):452-456.
Sola et al., "Glycosylation of Therapeutic Proteins," BioDrugs, Aug. 2010, 24(1):9-21.
Suckau et al., "Protein surface topology-probing by selective chemical modification and mass spectrometric peptide mapping," Proceedings of the National Academy of Sciences of the USA, Jun. 1992, 89(12):5630-5634.
Taverna et al., "Why are proteins marginally stable?," Proteins, Nov. 2002, 46(1):105-109.
Thilakarathne et al., "Protein Polymer Conjugates: Improving the Stability of Hemoglobin with Poly(acrylic acid)," Langmuir, May 2011, 27(12):7663-7671.
Trzebicka et al., "Thermoresponsive polymer-peptide/protein conjugates," Progress in Polymer Science, May 2017, 68:35-76.

(56) References Cited

OTHER PUBLICATIONS

Ugarova et al., "Chemical modification of the ε-amino groups of lysine residues in horseradish peroxidase and its effect on the catalytic properties and thermostability of the enzyme," Biochimica et Biophysica Acta (BBA)—Enzymology, Sep. 1979, 570(1):31-42.
Veronese et al., "PEGylation, successful approach to drug delivery," Drug Discovery Today, 2005, 10(21):1451-1458.
Veronese et al., "The impact of PEGylation on biological therapies," BioDrugs, 2008, 22(5): 315-329.
Wang et al., "Enhancing Accuracy in Molecular Weight Determination of Highly Heterogeneously Glycosylated Proteins by Native Tandem Mass Spectrometry," Analytical Chemistry, 2017, 89(9):4793-4797.
Wang et al., "Structural and biological characterization of pegylated recombinant interferon alpha-2b and its therapeutic implications," Advanced Drug Delivery Reviews, Jun. 2002, 54(4):547-570.
Wang et al., "Tuning the molecular size of site-specific interferon-polymer conjugate for optimized antitumor efficacy," Science China Materials, Jun. 2017, 60(6):563-570.
Welinder et al., "Effects of glycosylation on protein folding, stability and solubility. Studies of chemically modified or engineered plant and fungal peroxidases," Progress in Biotechnology, 1995, 10:205-210.
Wenck et al., "A Noncovalent Switch for Lysozyme," Journal of the American Chemical Society, 2007, 129(51):16015-16019.
Williams et al., "Strategies for Biophysical Characterization of Protein-Polymer Conjugates," NanoArmoring of Enzymes: Rational Design of Polymer-Wrapped Enzymes, 2017, 590:93-114.
Xiao et al., "Rational modification of protein stability by targeting surface sites leads to complicated results," Proc. Natl. Acad Sci. USA, Jul. 2013, 110(28): 11337-11342.
Zhang et al., "On the role of electrostatics in protein-protein interactions," Physical Biology, May 2011, 8(3):35001.
Ahmed et al., "Surface Plasmon Resonance (SPR) Spectrometry as a Tool to Analyze Nucleic Acid-Protein Interactions in Crude Cellular Extracts," Cancer Genomics & Proteomics, Nov. 2010, 7(6):303-309.
Bi et al., "Introducing Biobased Ionic Liquids as the Nonaqueous Media for Enzymatic Synthesis of Phosphatidylserine," Journal of Agricultural and Food Chemistry, Jan. 2015, 63(5):1558-1561.
Burczak et al., "Protein permeation through poly(vinyl alcohol) hydrogel membranes," Biomaterials, Feb. 1994, 15(3):231-238.
Carmali et al., "Tailoring Site Specificity of Bioconjugation Using Step-Wise Atom-Transfer Radical Polymerization on Proteins," Biomacromolecules, Sep. 2018, 19(10):4044-4051.
Chen et al., "Surface hydration: Principles and applications toward low-fouling/nonfouling biomaterials," Polymer, Oct. 2010, 51(23):5283-5293.
Chien et al., "Surface conjugation of zwitterionic polymers to inhibit cell adhesion and protein adsorption," Colloids and Surfaces B: Biointerfaces, Jul. 2013, 107:152-159.
Ghisaidoobe et al., "Intrinsic Tryptophan Fluorescence in the Detection and Analysis of Proteins: A Focus on Förster Resonance Energy Transfer Techniques," International Journal of Molecular Sciences, Dec. 2014, 15:22518-22538.
Green et al., "Surface plasmon resonance for real time in situ analysis of protein adsorption to polymer surfaces," Biomaterials, Mar. 1997, 18(5):405-413.
Green et al., "Surface plasmon resonance analysis of dynamic biological interactions with biomaterials," Biomaterials, Sep. 2000, 21(18):1823-1835.
Grewer et al., "Mechanism of the Triplet-State Quenching by Molecular Oxygen in Solution," Journal of Physical Chemistry, Apr. 1994, 98(16):4230-4235.
Grover et al., "Protein-polymer conjugates: synthetic approaches by controlled radical polymerizations and interesting applications," Current Opinion in Chemical Biology, Dec. 2010, 14(6): 818-827.
Hook et al., "Variations in Coupled Water, Viscoelastic Properties, and Film Thickness of a Mefp-1 Protein Film during Adsorption and Cross-Linking: A Quartz Crystal Microbalance with Dissipation Monitoring, Ellipsometry, and Surface Plasmon Resonance Study," Analytical Chemistry, Nov. 2001, 73(24):5796-5804.
Jeon et al., "Protein—surface interactions in the presence of polyethylene oxide: I. Simplified theory," Journal of Colloid and Interface Science, Mar. 1991, 142(1): 149-158.
Jevsevar et al., "PEGylation of therapeutic proteins," Biotechnology Journal, Jan. 2010, 5(1):113-128.
Kurzban et al., "Shielding of tryptophan residues of avidin by the binding of biotin," Biochemistry, Oct. 1989, 28(21):8537-8542.
Kurzban et al., "Biotin binding changes the conformation and decreases tryptophan accessibility of streptavidin," Journal of Protein Chemistry, Dec. 1990, 9:673-682.
Leigh et al., "Photopolymerizable Zwitterionic Polymer Patterns Control Cell Adhesion and Guide Neural Growth," Biomacromolecules, Jul. 2017, 18(8):2389-2401.
Lin et al., "Different in vitro and in vivo behaviors between Poly(carboxybetaine methacrylate) and poly(sulfobetaine methacrylate)," Colloids and Surfaces B: Biointerfaces, Oct. 2016, 146:888-894.
Liu et al., "Molecular Sieving on the Surface of a Protein Provides Protection Without Loss of Activity," Advanced Functional Materials, Nov. 2012, 23(16):2007-2015.
Luan et al., ""Hearing Loss" in QCM Measurement of Protein Adsorption to Protein Resistant Polymer Brush Layers," Analytical Chemistry, Mar. 2017, 89(7):4184-4191.
Macbeath et al., "Printing Small Molecules as Microarrays and Detecting Protein-Ligand Interactions en Masse," Journal of the American Chemical Society, Aug. 1999, 121(34):7967-7968.
Muegge et al., "A General and Fast Scoring Function for Protein-Ligand Interactions: A Simplified Potential Approach," Journal of Medicinal Chemistry, Feb. 1999, 42(5):791-804.
PCT International Preliminary Report on Patentability in International Application No. PCT/US2019/055977, dated Apr. 8, 2021, 5 pages.
PCT International Search Report and Written Opinion in International Application No. PCT/US2019/055977, dated Jun. 17, 2020, 10 pages.
Sarker et al., "Excited States of Bromine-Substituted Distyrylbenzenes: Models for Conjugated Polymer Emission," The Journal of Physical Chemistiy A, Aug. 2003, 107(34):6533-6537.
Schlenoff, "Zwitteration: Coating Surfaces with Zwitterionic Functionality to Reduce Nonspecific Adsorption," Langmuir, Apr. 2014, 30(32):9625-9636.
Skelly et al., "Conformational effects of nucleotide exchange in ras p21 proteins as studied by fluorescence spectroscopy," FEBS Letters, Mar. 1990, 262(1): 127-130.
Sofia et al., "Poly(ethylene oxide) Grafted to Silicon Surfaces: Grafting Density and Protein Adsorption," Macromolecules, Jul. 1998, 31(15):5059-5070.
Szleifer, "Protein adsorption on surfaces with grafted polymers: a theoretical approach," Biophysical Journal, Feb. 1997, 72(2):595-612.
Treethammathurot et al., "Effect of PEG molecular weight and linking chemistry on the biological activity and thermal stability of PEGylated trypsin," International Journal of Pharmaceutics, Jun. 2008, 357(1-2):252-259.
Vivian et al., "Mechanisms of Tryptophan Fluorescence Shifts in Proteins," Biophysical Journal, May 2001, 80(5):2093-2109.
Wilchek et al., "Essentials of biorecognition: The (strept)avidin-biotin system as a model for protein-protein and protein-ligand interaction," Immunology Letters, Feb. 2006, 103(1):27-32.
Wu et al., "Protein-polymer therapeutics: a macromolecular perspective," Biomaterials Science, Oct. 2014, 3(2):214-230.
Yee et al., "NMR and X-ray Crystallography, Complementary Tools in Structural Proteomics of Small Proteins," Journal of the American Chemical Society, Nov. 2005, 127(47): 16512-16517.
Enciso et al., "A Breathing Atom-Transfer Radical Polymerization: Fully Oxygen-Tolerant Polymerization Inspired by Aerobic Respiration of Cells," Angewandte Chemie, 2018, 57:933-936.
Fu et al., "Synthesis of Polymer Bioconjugates via Photoinduced Atom Transfer Radical Polymerization under Blue Light Irradiation," ACS Macro Letters, 2018, 7:1248-1253.

(56) References Cited

OTHER PUBLICATIONS

Abian et al., "Stabilization of penicillin G acylase from *Escherichia coli*: site-directed mutagenesis of the protein surface to increase multipoint covalent attachment," J. M. Appl. Environ. Microbiol., 2004, 70(2):1249-51.
Advances in Polymer Science; Springer Berlin / Heidelberg: 2002, vol. 159 (Table of Contents).
Affleck et al., "Enzymatic catalysis and dynamics in low-water environments," Proceedings of the National Academy of Sciences of the United States of America, 1992, 89(3):1100-1104.
Al-Ajlan et al., "Purification and partial characterization of camel anionic chymotrypsin," Arch. Biochem. Biophys., 1997, 348(2):363-8.
Alconcel et al., "FDA-approved poly(ethylene glycol)-protein conjugate drugs," Polymer Chem., 2011, 2:1442-1448.
Amitai et al., "Decontamination of chemical and biological warfare agents with a single multi-functional material," Biomaterials, May 2010, 31(15):4417-4425.
Arotcarena et al., "Switching the Inside and the Outside of Aggregates of Water-Soluble Block Copolymers with Double Thermoresponsivity," J. Am. Chem. Soc., 2002, 124(14):3787-3793.
Asgeirsson et al., "Structural and kinetic properties of chymotrypsin from Atlantic cod (*Gadus morhua*). Comparison with bovine chymotiypsin," Comp. Biochem. Physiol B., 1991, 99(2):327-35.
Ashani et al., "Estimation of the Upper Limit of Human Butyrylcholinesterase Dose Required for Protection against Organophosphates Toxicity: a Mathematically Based Toxicokinetic Model", Toxicological Sciences, 2004, 77(2):358-367.
Asmus et al., "Low-temperature NMR characterization of reaction of sodium pyruvate with hydrogen peroxide," J. Phys. Chem. A., 2015, 119(6):966-977.
Averick et al., "ATRP under Biologically Relevant Conditions: Grafting from a Protein", ACS Macro Letters, 2012, 1(1):6-10.
Averick et al., "Preparation of Cationic Nanogels for Nucleic Acid Delivery," Biomacromolecules, 2012, 13(11):3445-3449.
Averick et al., "Well-defined biohybrids using reversible-deactivation radical polymerization procedures," J. Control. Release, 2015, 205:45-57.
Baldassarre et al., "Detection of endoplasmic reticulum stress markers and production enhancement treatments in transgenic goats expressing recombinant human butvrvlcholinesterase," Transgenic Res, Dec. 2011, 20(6):1265-1272.
Baldwin, "How Hofmeister Ion Interactions Affect Protein Stability," Biophys J., 1996, 71(4):2056-2063.
Bas et al., "Very Fast Prediction and Rationalization of pKa Values for Protein-ligand Complexes," Proteins: Struct., Funct., Bioinf., 2008, 73: 765-783.
Bennion et al., "Counteraction of urea-induced protein denaturation by trimethylamine N-oxide: a chemical chaperone at atomic resolution," Natl. Acad. Sci. U.S.A., 2004, 101(17):6433-8.
Benns et al., "pH-Sensitive Cationic Polymer Gene Delivery Vehicle: N-Ac-poly(L-histidine)-graft-poly(L-lysine) Comb Shaped Polymer," Bioconjugate Chem, 2000, 11(5):637-645.
Benschop et al., "Nerve agent stereoisomers: analysis, isolation and toxicology," Acc. Chem. Res., 1988, 21(10):368-374.
Berberich et al., "Use of Salt Hydrate Pairs to Control Water Activity for Enzyme Catalysis in Ionic Liquids," Biotechnology Progress, 2003, 19(3):1029-1032.
Bigley et al., "Enzymatic Neutralization of the Chemical Warfare Agent VX: Evolution of Phosphotriesterase for Phosphorothiolate Hydrolysis," J. Am. Chem. Soc., 2013, 135(28):10426-10432.
Blencowe et al., "Core cross-linked star polymers via controlled radical polymerisation," Polymer, 2009, 50(1):5-32.
Blow "The study of alpha-chymotrypsin by x-ray diffraction. The Third CIBA Medal Lecture," Biochem. J., 1969, 112(3):261-268.
Boal et al., "Structural biology of copper trafficking," Chemical Reviews, 2009, 109(10):4760-4779.
Bonet et al., "Glucose oxidase effect on dough rheology and bread quality: A study from macroscopic to molecular level," Food Chemistiy, 2006, 99(2):408-415.
Bordusa, "Proteases in Organic Synthesis," Chemical Reviews, 2002, 102(12):4817-4868.
Borowitz et al., "Study of a novel pancreatic enzyme replacement therapy in pancreatic insufficient subjects with cystic fibrosis," J. Pediatr., 2006, 149(5):658-662.
Bovara et al., "Activity, stability and conformation of methoxypoly(ethylene glycol)-subtilisin at different concentrations of water in dioxane," Biotechnol Bioeng, 1997, 54(1):50-57.
Bowers et al., "Scalable Algorithms for Molecular Dynamics Simulations on Commodity Clusters," F. D. In SC 2006 Conference, Proceedings of the ACM/IEEE;IEEE: 2006, 43.
Boyer et al., "Well-Defined Protein-Polymer Conjugates via in Situ RAFT Polymerization," J. Am Chem. Soc., 2007, 129(22):7145-7154.
Braunecker, "Controlled/living radical polymerization: Features, developments, and perspectives," Prog. Polym. Sci., 2007, 32(1):93-146.
Brittain et al., "A Structural Definition of Polymer Brushes," Polym. Sci., Part A, Polym. Chem. 2007, 45(16):3505-3512.
Bultz et al., "Ferrocene cocatalysis for ruthenium-catalyzed radical miniemulsion polymerization," Polymer, 2016, 106:313-319.
Callahan et al., "Triple Stimulus-Responsive Polypeptide Nanoparticles That Enhance Intratumoral Spatial Distribution," Nano Lett., 2012, 12(4):2165-2170.
Campbell et al., "Polymer-Based Protein Engineering Grown Ferrocene-Containing Redox Polymers Improve Current Generation in an Enzymatic Biofuel Cell," Biosensors and Bioelectronics, Jun. 2016, 86, 446-453.
Carrea et al., "Properties and Synthetic Applications of Enzymes in Organic Solvents," Angewandte Chemie International Edition, 2000, 39(13):2226-2254.
Castillo-Yanez et al., "Biochemical characterization of an isoform of chymotrypsin from the viscera of Monterey sardine (*Sardinops sagax caerulea*), and comparison with bovine chymotrypsin," Food Chem., 2009, 112(3):634-639.
Chan et al., "Chapter 2—Building on What Nature Gave Us: Engineering Cell Glycosylation Pathways," Biotechnology Bioengineering, 2008, pp. 37-74.
Chao et al., "Two structural scenarios for protein stabilization by PEG," J. Phys. Chem. B, 2014, 118(28):8388-95.
Chapman et al., "Combinatorial Low-Volume Synthesis of Well-Defined Polymers by Enzyme Degassing," Angew. Chem. Int. Ed., 2016, 55(14):4500-4503.
Chapman et al., "Highly Controlled Open Vessel RAFT Polymerizations by Enzyme Degassing," Macromol., 2014, 47(24):8541-8547.
Charles, "Soluble-Insoluble Enzyme Catalysts," Biotechnol Bioeng., 1974, 16(11):1553-1556.
Chen et al., "Quaternary Ammonium Functionalized Poly(propylene imine) Dendrimers as Effective Antimicrobials: Structure-Activity Studies," Biomacromolecules, 2000, 1(3):473-480.
Chen et al., "Effects of poly electrolyte complexation on the UCST of zwitterionic polymer," Polymer, 2000, 41:141-147.
Chen et al., "Polymer-protein conjugates: II. Affinity precipitation separation of human immunogammaglobulbin by a poly(isopropylacrylamide-) protein A conjugate," Biomaterials, 1990, 11(9):631-634.
Chilkoti et al., "Targeted drug delivery by thermally responsive polymers," Adv Drug Deliver Rev, 2002, 54(5):613-630.
Ciampolini et al., "Five-Coordinated High-Spin Complexes of Bivalent Cobalt, Nickel, and Copper withTris(2-dimethylaminoethyl)amine," Inorg. Chem., 1966, 5(1):41-44.
Coessens et al., "Functional polymers by atom transfer radical polymerization," Prog. Polym. Sci., 2001, 26(3):337-377.
Cummings et al., "Dramatically Increased pH and Temperature Stability of Chymotrypsin Using Dual Block Polymer-Based Protein Engineering," Biomacromolecules, 2014, 15(3):763-771.
Cummings et al., "Polymer-Based Protein Engineering Enables Molecular Dissolution of Chymotrypsin in Acetonitrile," ACS Macro Letters, 2016, 5(4):493-497.

(56) References Cited

OTHER PUBLICATIONS

Cummings et al., "Tailoring enzyme activity and stability using polymer-based protein Engineering," Biomaterials, 2013, 34(30):7437-7443.

Davidovich-Pinhas et al., "Mucoadhesion: a review of characterization techniques," Expert Opin. Drug Deliveiy, 2010, 7(2):259-71.

Davis et al., "A place for thioether chemistry in cellular copper ion recognition and trafficking," Nature Chem. Bio., 2008, 4(3):148-151.

De et al., "Temperature-Regulated Activity of Responsive Polymer-Protein Conjugates Prepared by Grafting-from via RAFT Polymerization," J. Am. Chem. Soc., 2008, 130(34):11288-11289.

Debuigne et al., "Synthesis of Poly(vinyl acetate) and Poly(vinyl alcohol) Containing Block Copolymers by Combination of Cobalt-Mediated Radical Polymerization and ATRP," Macromol., 2005, 38(23):9488-9496.

Depp et al., "Enzyme Sheathing Enables Nanoscale Solubilization of Biocatalyst and Dramatically Increases Activity in Organic Solvent," Biomacromolecules, 2008, 9(4):1348-1351.

Desie et al., "Study of the time-resolved tryptophan fluorescence of crystalline alpha-chymotrypsin," Biochemistry, 1986, 25(25):8301-8.

Dinndorf, P., et al., "FDA Drug Approval Summary: Pegaspargase (Oncaspar®) for the First-Line Treatment of Children with Acute Lymphoblastic Leukemia (ALL)," Oncologist, 2007, 12(8):991-998.

DiPalma et al., "Enzyme replacement for lactose malabsorption using a beta-D-galactosidase," J. Clin. Gastroenterol., 1989, 11(3):290-3.

Dong et al., "Synthesis and responsive behavior of poly(N,N-dimethylaminoethyl methacrylate) brushes grafted on silica nanoparticles and their quaternized derivatives," Polymer, 2012, 53(10):2074-2084.

Drevon et al., "Enzyme-Containing Michael-Adduct-Based Coatings," Biomacromolecules, 2003, 4(3):675-682.

Eckstein et al., "At low water activity α-chymotrypsin is more active in an ionic liquid than in non-ionic organic solvents," Biotechnology Letters, 2002, 24(11):867-872.

Eddleston et al., "Management of acute organophosphoms pesticide poisoning," Lancet, Feb. 2008, 371(9612):597-607.

Estevez et al. "Model equations for the kinetics of covalent irreversible enzyme inhibition and spontaneous reactivation: Esterases and organophosphoms compounds," Critical Reviews in Toxicology, 2009, 39(5):427-448.

Eyer, "The Role of Oximes in the Management of Organophosphoms Pesticide Poisoning," Toxicological Reviews, 2003, 22(3):165-190.

Falatach et al., "Why synthesize protein-polymer conjugates? The stability and activity of chymotiypsin-polymer bioconjugates synthesized by RAFT," Polymer, 2015, 72(18):382-386.

Fantin et al., "Atom Transfer Radical Polymerization of Methacrylic Acid: A Won Challenge," J. Am. Chem. Soc., 2016, 138(23):7216-7219.

Fantin et al., "ATRP in Water: Kinetic Analysis of Active and Super-Active Catalysts for Enhanced Polymerization Control," Macromol., 2017, 50(7):2696-2705.

Fieker et al., "Enzyme replacement therapy for pancreatic insufficiency: present and future," M. Clin. Exp. Gastroenterol., 2011, 4:55-73.

Fischer et al., "Inhibition of chymotrypsin through surface binding using nanoparticle-based receptors," P. Natl. Acad. Sci. U.S.A. 2002, 99(8)5018-23.

Fuhrmann et al., "Sustained gastrointestinal activity of dendronized polymer-enzyme conjugates," Nat. Chem. 2013, 5(7):582-589.

Gao et al., "Synthesis of functional polymers with controlled architecture by CRP of monomers in the presence of cross-linkers: From stars to gels," Prog. Polym. Sci., 2009, 34(4):317-350.

Gao et al., "In situ growth of a stoichiometric PEG-like conjugate at a protein's N-terminus with significantly improved pharmacokinetics," Proc. Natl. Acad. Sci. USA, 2009, 106(36):15231-15236.

Gauthier et al., "Polymer-protein conjugates: an enzymatic activity perspective," Poly. Chem., 2010, 1(9);1341-1520.

Geokas et al., "The aging gastrointestinal tract, liver, and pancreas," P. Clin. Geriatr. Med., 1985, 1(1):177-205.

Goldsmith, "Enzyme Engineering by Targeted Libraries," Meth Enzymol, 2013, 523:257-283.

Gormley et al., "Polymerization amplified detection for nanoparticle-based biosensing," Nano Letters, 2014, 14(11):6368-6373.

Graham, "Enzyme replacement therapy of exocrine pancreatic insufficiency in man. Relations between in vitro enzyme activities and in vivo potency in commercial pancreatic extracts," N. Engl. J. Med., 1977, 296(23):1314-7.

Gulla et al., "Reactivation of immobilized acetyl cholinesterase in an amperometric biosensor for organophosphorus pesticide," Biochim Biophys Acta, 2002, 1597(1):133-139.

Günther et al., "Trypsin-specific acyl-4-guanidinophenyl esters for alpha-chymotrypsin-catalysed reactions computational predictions, hydrolyses, and peptide bond formation," J. Biochem., 2000, 267(12) 3496-501.

Gupta et al., "Directed evolution of hydrolases for prevention of G-type nerve agent intoxication," Nature Chemical Biology, 2011, 7(2):120-125.

Han et al., "Fluorometric Assay Protocol for Protease-Catalyzed Transesterification Reactions in Organic Solvents," The Journal of Organic Chemistiy, 2004, 69(8):2853-2855.

Handbook of Radical Polymerization, K. Matyjaszewski and T. Davis, Ed., John Wiley & Sons, Inc. pub. (2002), pp. 553-555, 567.

Hedstrom et al., "Serine Protease Mechanism and Specificity," Chem. Rev. 2002, 102(12):4501-4523.

Helsel et al., "Pharmacological activity of metal binding agents that alter copper bioavailability," Dalton Transactions, 2015, 44(19):8760-8770.

Heredia et al., "In Situ Preparation of Protein-"Smart" Polymer Conjugates with Retention of Bioactivity," J Am Chem Soc, 2005, 127(48):16955-16960.

Heyman, "Lactose intolerance in infants, children, and adolescents," Pediatrics, 2006, 118(3)1279-86.

Hoffman et al., "Conjugates of Stimuli-responsive polymers and proteins," Prog. Polymer Sci., 2007, 32(8-9):922-932.

Hong et al., "Conjugation of α-chymotrypsin on a polymeric hydrophilic nanolayer covering magnetic nanoparticles," J. Mol. Catal. B: Enzym., 2006, 42(3-4):99-105.

Huang et al., "Nonleaching Antibacterial Glass Surfaces via "Grafting Onto": The Effect of the Number of Quaternary Ammonium Groups on Biocidal Activity," Langmuir, 2008, 24(13):6785-6795.

Iwata et al., "Initiation of radical polymerization by glucose oxidase utilizing dissolved oxygen," J. Polym. Sci. Part A, Polym. Chem., 1991, 29(8):1217-1218.

Jesson et al., "H2O2 Enables Convenient Removal of RAFT End-Groups from Block Copolymer Nano-Objects Prepared via Polymerization-Induced Self-Assembly in Water," Macromolecules, 2017, 50(1):182-191.

Jockusch et al., "The active role of excited states of phenothiazines in photoinduced metal free atom transfer radical polymerization: singlet or triplet excited states?" Polymer Chemistry, 2016, 7(39):6039-6043.

Kaar et al., "Impact of Ionic Liquid Physical Properties on Lipase Activity and Stability," J Am Chem Soc, 2003, 125(14):4125-4131.

Kamigaito et al., "Metal-catalyzed living radical polymerization," Chem Rev, 2001, 101(12):3689-3746.

Keefe et al., "Poly(zwitterionic)protein conjugates offer increased stability without sacrificing binding affinity or bioactivity," Nat Chem, 2012, 4(1):59-63.

Kijima et al., "Study on tryptophan fluorescence and catalytic activity of α-chymotrypsin in aqueous-organic media," Enzyme Microb. Technol., 1996, 18(1):2-6.

Kitz et al., "Activity-structure relationships in the reactivation of diethylphosphoryl acetylcholinesterase by phenyl-1-methyl-pyridinium," Biochem Pharmacol, 1965, 14(10):1471-1477.

Klibanov, "Improving enzymes by using them in organic solvents," Nature, 2001, 409(6817):241-6.

(56) References Cited

OTHER PUBLICATIONS

Kolb et al., "Click Chemistry: Diverse Chemical Function from a Few Good Reactions," Agnew. Chem. Int. Ed., 2001, 40(11):2004-2021.
Konieczny et al., "Investigations on the activity of poly(2-oxazoline) enzyme conjugates dissolved in organic solvents", Journal of Biotechnology, 2014, 181(5):55-63.
Konkolewicz et al., "ICAR ATRP with ppm Cu Catalyst in Water," Macromol., 2012, 45(11):4461-4468.
Kostina et al., "Non-fouling hydrogels of 2-hydroxyethyl methacrylate and zwitterionic carboxybetaine (meth)acrylamides," Biomacromolecules, 2012, 13(12)4164-70.
Kovarik et al., "Mutation of acetylcholinesterase to enhance oxime-assisted catalytic turnover of methylphosphonates," Toxicology, 2007, 233(1-3):79-84.
Kovarik et al., "Oximes: Reactivators of phosphorylated-acetylcholinesterase and antidotes in therapy against tabun poisoning," Chemico-Biological Interactions, 2008, 175(1-3):173-179.
Kuca et al., "Synthesis of the three monopyridinium oximes and evaluation of their potency to reactivate acetylcholinesterase inhibited by nerve agents," J Appl Biomed, 2004, 2:51-56.
Kulkarni et al., "Controlling the Aggregation of Conjugates of Streptavidin with Smart Block Copolymers Prepared via the RAFT Copolymerization Technique," Biomacromolecules, 2006, 7(10):2736-2741.
Kulkarni et al., "Reversible Meso-Scale Smart Polymer-Protein Particles of Controlled Sizes," Bioconjugate Chem., 2004, 15(4):747-753.
Kumar et al., "Overview of the Stability of α-Chymotrypsin in Different Solvent Media," Chem. Rev., 2012, 112(7):4283-4307.
Kurinomaru et al., "Effects of multivalency and hydrophobicity of polyamines on enzyme hyperactivation of α-chymotrypsin," J. Mol. Catal. B: Enzym., 2015, 115:135-139.
Lackey et al., "Hemolytic Activity of pH-Responsive Polymer-Streptavidin Bioconjugates," Bioconjugate Chem., 1999, 10(3):401-405.
Larger et al., "Pancreatic exocrine function in patients with diabetes," Diabetic Medicine, 2012, 29(8):1047-1054.
Laszlo et al., "alpha-chymotrypsin catalysis in imidazolium-based ionic liquids," Biotechnol Bioeng, 2001, 75(2):181-186.
Lawrence et al., "Conjugation Strategy Strongly Impacts the Conformational Stability of a PEG-Protein Conjugate," ACS Chem. Biol., 2016, 11(7):1805-1809.
Lawrence et al., "Criteria for Selecting PEGylation Sites on Proteins for Higher Thermodynamic and Proteolytic Stability," J. Am. Chem. Soc., 2014, 136(50):17547-17560.
Lawrence et al., "How PEGylation influences protein conformational stability," Curr. Opin. Chem. Biol., 2016, 34:88-94.
Leach, "Release and breakdown of sialic acid from human salivary mucin and its role in the formation of dental plaque," Nature, 1963, 199:486-7.
Lee et al., "Activation of Oxygen and Hydrogen Peroxide by Copper(II) Coupled with Hydroxylamine for Oxidation of Organic Contaminants," Environ. Sci. Technol., 2016, 50(15):8231-8238.
LeJeune et al., "Covalent linkage of mammalian cholinesterases within polyurethane foams," Med. Def. Biosc. Rev. Proc., 1996, 1:223-230.
Lele et al., "Enhancing Enzyme Stability Against TiO2-UV Induced Inactivation," Biomacromolecules, 2005, 6(1):475-482.
Lele et al., "Synthesis of Uniform Protein-Polymer Conjugates," Biomacromolecules, 2005, 6(6):3380-3387.
Lele, "Rational Protein Modification Leading to Resistance of Enzymes to TiO2-UV Irradiation-Induced Inactivation," Biomacromolecules, 2004, 5(5):1947-1955.
Li et al., "Block copolymer conjugates prepared by sequentially grafting from proteins via RAFT," Polym. Chem., 2011, 2:1531-1535.
Li et al., "Thermoresponsive Block Copolymer-Protein Conjugates Prepared by Grafting-from via RAFT Polymerization," Macromol. Rapid Commun., 2011, 32(4):354-359.
Li et.al., "Single-Ion Homopolymer Electrolytes with High Transference No. Prepared by Click Chemistry and Photoinduced Metal-Free Atom-Transfer Radical Polymerization," ACS Energy Letters, 2018, 3:20-27.
Limer et al., "Amide Functional Initiators for Transition-Metal-Mediated Living Radical Polymerization," Macromolecules, 2006, 39(4):1353-1358.
Lisowska et al., "Unresponsive or non-compliant steatorrhea in cystic fibrosis?," J. Cystic Fibrosis, 2006, 5(4):253-5.
Liu et al., "In Situ Formation of Protein-Polymer Conjugates through Reversible Addition Fragmentation Chain Transfer Polymerization," Angew. Chem., Int. Ed. 2007, 46(17):3099-3103.
Lo Nostro et al., "Hofmeister Phenomena: An Update on Ion Specificity in Biology," Chem Rev 2012, 112(4):2286-2322.
Loke et al., "O-Substituted derivatives of pralidoxime: muscarinic properties and protection against soman effects in rats," European Journal of Pharmacology, 2002, 442(3):279-287.
Lu et al., "Controllable synthesis of poly(N-vinylpyrrolidone) and its block copolymers by atom transfer radical polymerization," Polymer 2007, 48(10):2835-2842.
Lucius et al., "Investigating the Impact of Polymer Functional Groups on the Stability and Activity of Lysozyme-Polymer Conjugates," Biomacromolecules, 2016, 17(3)1123-34.
Lundy et al., "Development of the Bisquatemary oxime HI-6 Toward Clinical Use in the Treatment of Organophosphate Nerve Agent Poisoning," Toxicological Reviews, 2006, 25(4):231-243.
Lv et al., "Glucose oxidase deoxygenation—redox initiation for RAFT polymerization in air," J. Polym. Sci. Part A, Polym. Chem., 2017, 55(1):164-174.
Magnusson et al., "In Situ Growth of Side-Chain PEG Polymers from Functionalized Human Growth Hormone—A New Technique for Preparation of Enhanced Protein-Polymer Conjugates," Bioconjugate Chem., 2010, 21(4):671-678.
Mancini et al., "Trehalose glycopolymers for stabilization of protein conjugates to environmental stressors," J. Am. Chem. Soc., 2012, 134(20):8474-9.
Masson, "Catalytic Bioscavengers Against Toxic Esters, an Alternative Approach for Prophylaxis and Treatments of Poisonings," Acta Naturae, 2009, No. 1(1):68-79.
Matyjaszewski et al, "Controlled/"Living" Radical Polymerization. Kinetics of the Homogeneous Atom Transfer Radical Polymerization of Styrene," J. Am. Chem. Soc., 1997, 119(4):674-680.
Matyjaszewski et al., "Macromolecular engineering by atom transfer radical polymerization," J. Am. Chem. Soc., 2014, 136(18):6513-6533.
Matyjaszewski, "Atom Transfer Radical Polymerization (ATRP): Current Status and Future Perspectives," Macromol., 2012, 45(10):4015-4039.
Matyjaszewski, "Atom transfer radical polymerization," Chem. Rev., 2001, 101(9):2921-2990.
Matyjaszewski, "Atom Transfer Radical Polymerization: From Mechanisms to Applications", Isr. J. Chem., 2012, 52(3-4):206-220.
Matyjaszewski, "Chemistry. Architecturally complex polymers with controlled heterogeneity," Science, 2011, 333(6046):1104-1105.
Matyjaszewski, Abstracts of Papers, Mar. 2018 ACS Meeting, POLY-157.
Mazor et al., "Aging-Resistant Organophosphate Bioscavenger Based on Polyethylene Glycol-Conjugated F338A Human Acetylcholinesterase," Molecular Pharmacology, 2008, 74(3):755-763.
McDaniel et al., "Actively targeting solid tumours with thermoresponsive drug delivery systems that respond to mild hyperthermia," Int. J. Hyperthermia. 2013, 29:501-510.
Millard et al., "Controlled/Living Radical Polymerization: Progress in ATRP," American Chemical Society, 2009, 1023:127-136.
Millard et al., "Design and Expression of Organophosphorus Acid Anhydride Hydrolase Activity in Human Butyiylcholinesterase," Biochemistry, 1995, 34(49):15925-15933.
Millard et al., "Organosphosphorus Acid Anhydride Hydrolase Activity in Human Butyrylcholinesterase: Synergy Results in a Somanase," Biochemistry, 1998, 37(1):237-247.
Montalto et al., "Management and treatment of lactose malabsorption," World J. Gastroenterol., 2006, 12(2):187-91.

(56) References Cited

OTHER PUBLICATIONS

Murata et al. "Solid-Phase Synthesis of Protein-Polymers on Reversible Immobilization Supports," Nature Communications, Feb. 2018, 9(1):1-10.
Murata et al., "Rational tailoring of substrate and inhibitor affinity via ATRP polymer-based protein engineering," Biomacromolecules, 2014, 15(7):2817-23.
Murata et al., "Polymer-Based Protein Engineering Can Rationally Tune Enzyme Activity, pH-Dependence, and Stability," Biomacromolecules, Jun. 2013, 14(6):1919-1926.
Naito, "Three-Dimensional Cardiac Tissue Engineering Using a Thermoresponsive Artificial Extracellular Matrix," ASAIO J. 2004, 50:344-348.
Nasongkla et al., "Multifunctional Polymeric Micelles as Cancer-Targeted, MRI-Ultrasensitive Drug Delivery Systems," Nano Lett, 2006, 6(11):2427-2430.
Nesbitt et al., "Mechanism of action of certolizumab pegol (CDP870): in vitro comparison with other anti-tumor necrosis factor alpha agents," Inflamm Bowel Dis, 2007, 13(11):1323-1332.
Nicolas et al., "Fluorescently tagged polymer bioconjugates from protein derived macroinitiators," Chem. Commun. 2006, 45:4697-4699.
Nordwald et al., "Stabilization of Enzymes in Ionic Liquids via Modification of Enzyme Charge," Biotechnology and Bioengineering, Apr. 2013, 110(9):2352-2360.
Nothling et al., "Self-deoxygenating glassware," Chem. Commun., 2019, 55(59):8544-8547.
Ordentlich et al., "The role of AChE active site gorge in determining stereoselectivity of charged and noncharged VX enantiomers," Chemico-Biological Interactions, 2005, 157-158:191-198.
O'Sullivan, "Use of Peginterferon Alfa-2B in Chronic Hepatitis C Patients Failing Prior Therapy: A Cost-Effectiveness Analysis," Value Health, 2008, 11(6):A437.
Oytun et al., "Sugar overcomes oxygen inhibition in photoinitiated free radical polymerization," J. Polym. Sci. Part A, Polym. Chem., 2013, 51(8):1685-1689.
Pan et al., "Automated Synthesis of Well-Defined Polymers and Biohybrids by Atom Transfer Radical Polymerization Using a DNA Synthesizer," Angew. Chem. Int. Ed., 2017, 56(10):2740-2743.
Pandey et al., "Impact of site-specific PEGylation on the conformational stability and folding rate of the Pin WW domain depends strongly on PEG oligomer length," Bioconjugate Chem., 2013, 24(5):796-802.
Park et al., "Mechanisms of mucoadhesion of poly(acrylic acid) hydrogels," Pharm. Res., 1987, 4(6):457-64.
Paterova et al., "Reversal of the Hofmeister Series: Specific Ion Effects on Peptides," J Phys Chem B, 2013, 117(27):8150-8158.
PCT International Preliminary Report on Patentability in International Appln. No. PCT/US2018/013552, dated Jul. 16, 2019, 9 pages.
PCT International Search Report and Written Opinion in International Appln. No. PCT/US2018/013552, dated Aug. 14, 2018, 17 pages.
Pettersen et al., "UCSF Chimera—a visualization system for exploratory research and analysis," J. Comput. Chem., 2004, 25(13):1605-12.
Pham et al., "Fenton-like copper redox chemistry revisited: Hydrogen peroxide and superoxide mediation of copper-catalyzed oxidant production," J. Catalysis, 2013, 301:54-64.
Polymer Science: A Comprehensive Reference, Eds., 2012;377-428.
Qi et al., "A brush-polymer/exendin-4 conjugate reduces blood glucose levels for up to five days and eliminates poly(ethylene glycol) antigenicity," Nat. Biomed. Eng., 2016, 1(1):1-12.
Qi et al., "PEGylated porcine glucagon-like peptide-2 improved the intestinal digestive function and prevented inflammation of weaning piglets challenged with LPS," Animal, 2015, 9(9):1481-9.
Qi et al., "Sortase-Catalyzed Initiator Attachment Enables High Yield Growth of a Stealth Polymer from the C-Terminus of a Protein," Macromol. Rapid Commun., 2013, 34(15):1256-1260.
Qiu et al., "Controlled/living radical polymerization in aqueous media: homogeneous and heterogeneous systems," Prog. Polym. Sci., 2001, 26(10):2083-2134.
Qiu et al., "Polymerization of Substituted Styrenes by Atom Transfer Radical Polymerization," Macromol., 1997, 30(19):5643-5648.
Radic et al., "Catalytic detoxification of nerve agent and pesticide organophosphates by butyrylcholinesterase assisted with non-pyridinium oximes," Biochem. J., 2013, 450(1):231-242.
Reineke et al., "Can bioadhesive nanoparticles allow for more effective particle uptake from the small intestine?," J. Controlled Release, 2013, 170(3):477-484.
Riccardi et al., "Toward "stable-on-the-table" enzymes: improving key properties of catalase by covalent conjugation with poly(acrylic acid)," Bioconjugate Chem., 2014, 25(8):1501-10.
Riener et al., "Quick measurement of protein sulfhydryls with Ellman's reagent and with 4,4'-dithiodipyridine," Anal Bioanal Chem, 2002, 373(4-5):266-276.
Robinson et al., "Copper Metallochaperones," Ann. Rev. Biochem., 2010, 79(1):537-562.
Röcker et al., "The use of glucose oxidase and catalase for the enzymatic reduction of the potential ethanol content in wine," Food Chemistry, 2016, 210:660-670.
Rodriguez et al., "Site-directed mutagenesis improves catalytic efficiency and thermostability of *Escherichia coli* pH 2.5 acid phosphatase/phytase expressed in Pichia pastoris," Arch. Biochem. Biophys., 2000, 382(1):105-12.
Rodríguez-Martínez et al., "Enzymatic activity and thermal stability of PEG-a-chymotrypsin conjugates," Biotechnol. Lett., 2009, 31(6):883-887.
Rodríguez-Martínez, et al., "Stabilization of a-Chymotrypsin Upon PEGylation Correlates With Reduced Structural Dynamics," Biotechnol. Bioeng., 2008, 101(6):1142-1149.
Russell et al., "Rational Modification of enzyme catalysis by engineering surface charge," Nature, 1987, 328(6130):496-500.
Russell et al., "Electrostatic Effects on Modification of Charged Groups in the Active Site Cleft of Subtilisin by Protein Engineering," Mol. Biol. 1987, 193(4):803-813.
Sandanaraj et al., "Noncovalent Modification of Chymotrypsin Surface Using an Amphiphilic Polymer Scaffold: Implications in Modulating Protein Function," J Am Chem Soc, 2005, 127:10693-10698.
Scheidig et al., "Crystal structures of bovine chymotrypsin and trypsin complexed to the inhibitor domain of Alzheimer's amyloid beta-protein precursor (APPI) and basic pancreatic trypsin inhibitor (BPTI): engineering of inhibitors with altered specificities," Protein Sci., 1997, 6(9):1806-24.
Schild, "Poly(N-Isopropylacrylamide): Experiment, Theory and Application," Prog. Polym., Sci. 1992, 17(2):163-249.
Schröder et al., "Substituted Tris(2-pyridylmethyl)amine Ligands for Highly Active ATRP Catalysts," ACS Macro Letters, 2012, 1(8):1037-1040.
Shan et al., "Chloride accelerated Fenton chemistry for the ultrasensitive and selective colorimetric detection of copper," Chem. Commun., 2016, 52(10):2087-2090.
Simakova et al., "Aqueous ARGET ATRP," Macromol., 2012, 45(16):6371-6379.
Simon et al., "Structure and activity of alpha-chymotrypsin and trypsin in aqueous organic media," Biochem. Biophys. Res. Commun., 2001, 280(5)1367-71.
Sioud et al., "Cationic liposome-mediated delivery of siRNAs in adult mice," Biochemical and Biophysical Research Communications 2003, 312(4):1220-1225.
Smart, "The basics and underlying mechanisms of mucoadhesion," Adv. Drug Delivery Rev., 2005, 57(11):1556-68.
Smith et al., "Vascular Catheters with a Nonleaching Poly-Sulfobetaine Surface Modification Reduce Thrombus Formation and Microbial Attachment," Sci. Transl. Med., 2012, 4(153):153ra132.
Somaraju et al., "Pancreatic enzyme replacement therapy for people with cystic fibrosis," Cochrane Db. Syst. Rev., 2014, 13(10):CD008227.
Stepankova et al., "Strategies for Stabilization of Enzymes in Organic Solvents," ACS Catalysis 2013, 3(12);2823-2836.
Street et al., "A molecular mechanism for osmolyte-induced protein stability," P. Natl. Acad. Sci. U.S.A., 2006, 103(38):13997-4002.

(56) References Cited

OTHER PUBLICATIONS

Strozyk et al., "Protein/Polymer-Based Dual-Responsive Gold Nanoparticles with pH-Dependent Thermal Sensitivity," Adv. Funct. Mater., 2012, 22(7):1436-1444.

Su et al. "Catechol Polymers for pH-Responsive, Targeted Drug Delivery to Cancer Cells," J. Am. Chem. Soc., 2011, 133(31):11850-11853.

Tan et al., "Enzyme-Assisted Photoinitiated Polymerization-Induced Self-Assembly: An Oxygen-Tolerant Method for Preparing Block Copolymer Nano-Objects in Open Vessels and Multiwell Plates," Macromolecules, 2017, 50(15):5798-5806.

Tang et al., "Effects of Initiator Structure on Activation Rate Constants in ATRP," Macromol., 2007, 40(6):1858-1863.

Taylor et al., "Acetylcholinesterase: Converting a vulnerable target to a template for antidotes and detection of inhibitor exposure," Toxicology, 2007, 233(1-3):70-78.

Taylor, "Chapter 6, Anticholinesterase Agents," Goodman and Gillman's The Pharmacological Basis of Therapeutics, 7th Ed., Macmillan Publishing Company, NY, 1985, pp. 110-129.

Teodorescu et al., "Atom Transfer Radical Polymerization of (Meth)acrylamides," Macromol., 1999, 32(15):4826-4831.

Terrier et al., "Revisiting the reactivity of oximate α-nucleophiles with electrophilic phosphorus centers. Relevance to detoxification of sarin, soman and DFP under mild conditions," Organic & Biomolecular Chemistry, 2006, 4(23):4352-4363.

Timasheff, "Protein-solvent preferential interactions, protein hydration, and the modulation of biochemical reactions by solvent components," P. Natl. Acad. Sci. U.S.A., 2002, 99(15):9721-6.

Trapnell et al., "Relationship Between Pancreatic Enzyme Replacement Therapy and Healthcare Use in Children with Cystic Fibrosis," M. Pediatr. Pulm., 2014, 49:406-407.

Tsarevsky et al., "Deactivation Efficiency and Degree of Control over Polymerization in ATRP in Protic Solvents," Macromolecules, 2004, 37(26):9768-9778.

Turner et al., "Stabilization of a supplemental digestive enzyme by post-translational engineering using chemically-activated polyethylene glycol," Biotechnol. Lett., 2011, 33(3):617-621.

Uchida et al., "Topography of Polymer Chains Grafted on a Polymer Surface Underwater," Macromolecules, 1997, 30(18):5464-5469.

Van de Wetering et al., "A Mechanistic Study of the Hydrolytic Stability of Poly(2-(dimethylamino)ethyl methacrylate)," Macromolecules, 1998, 31:8063-8068.

Van Hooidonk et al., "On the reactivity of organophosphorus compounds Part IV. The alkaline hydrolysis of some O-phosphorylated 2-pyridine oximes," Rec. Trav. Chim. 1968, 87(6):673-686.

Van Leemputten et al., "Soluble-Insoluble Complex of Trypsin Immobilized on Acrolein-Acrylic Acid Copolymer," Biotech. Bioeng., 1976, 18(4):587-590.

Venkataraman et al., "ATRP from an amino acid-based initiator: A facile approach for α-functionalized polymers," Macromolecules, 2006, 39(26):9661-9664.

Veronese, "Peptide and Protein PEGylation: a review of problems and solutions," Biomaterials, 2001, 22(5):405-417.

Wang et al., "Controlled/"living" radical polymerization, atom transfer radical polymerization in the presence of transition," J. Am. Chem. Soc., 1995, 117(20):5614-5615.

Wang et al., "Improving the Protein Activity and Stability Under Acidic Conditions via Site-Specific Conjugation of a pH-Responsive Polyelectrolyte," Journal of Materials Chemistry B, Jan. 2015, 3(3):498-504.

Wang et al., "Functional protein-organic/inorganic hybrid nanomaterials," Wiley Interdisciplinary Reviews: Nanomedicine and Nanobiotechnology, 2013, 5(4):320-328.

Wang, "Lyophilization and development of solid protein pharmaceuticals," Int. J. Appl. Pharm., 2000, 203(1-2):1-60.

Watson, "Exocrine insufficiency and pancreatic enzyme replacement therapy in pancreatic cancer," Clin. Oncol. (R Coll Radiol), 2010, 22(5):391.

Weaver, et al. "Synthesis and aqueous solution properties of a well-defined thermo-responsive schizophrenic diblock copolymer," Chem. Commun., 2002, 18:2122-2123.

Webb, "Drugmakers dance with autism," Nat. Biotechnol., 2010, 28(8):722-4.

Werle, "Strategies to improve plasma half life time of peptide and protein drugs," Amino Acids, 2006, 30(4):351-67.

Wever et al., "Acrylamide Homopolymers and Acrylamide-N-Isopropylacrylamide Block Copolymers by Atomic Transfer Radical Polymerization in Water," Macromol., 2012, 45(10):4040-4045.

Wijmans et al., "Polymer Brushes at Curved Surfaces," Macromolecules, 1993, 26(26):7214-7224.

Written Opinion of the International Searching Authority for International Appln. No. PCT/US2014/035033, dated Aug. 28, 2014, 5 pages.

Wysocka et al., "Designing of Substrates and Inhibitors of Bovine α-Chymotrypsin with Synthetic Phenylalanine Analogues in Position P1," Protein Pept. Lett., 2008, 15(3):260-264(5).

Xenos et al., "Treatment of lactose intolerance with exogenous beta-D-galactosidase in pellet form," Eur. J. Drug Metab. Ph., 1998, 23(2):350-5.

Xu et al., "Scalable method to produce biodegradable nanoparticles that rapidly penetrate human mucus," J. Controlled Release, 2013, 170(2):279-286.

Yang et al., "Polyethylene glycol-induced stabilization of subtilisin," Enzyme Microb. Technol., 1996, 18(2):82-89.

Yaşayan et al., "Responsive hybrid block co-polymer conjugates of proteins-controlled architecture to modulate substrate specificity and solution behavior," C. Polym., Chem., 2011, 2(7):1567-1578.

Yin et al., "Drug permeability and mucoadhesion properties of thiolated trimethyl chitosan nanoparticles in oral insulin delivery," Biomaterials, 2009, 30(29):5691-700.

Zhang et al., "Effects of Hofmeister Anions on the LCST of PNIPAM as a Function of Molecular Weight," J. Phys. Chem. C 2007, 111(25):8916-8924.

Zhang et al., "Enhanced catalytic activity in organic solvents using molecularly dispersed haemoglobin-polymer surfactant constructs," Chem Commun. 2013, 49(83):9561-9563.

Zhang et al., "Interactions between macromolecules and ions: the Hofmeister series," Current Opinion in Chemical Biology, 2006, 10(6):658-663.

Zhang et al., "Polysulfobetaine-Grafted Surfaces as Environmentally Benign Ultralow Fouling Marine Coatings," Langmuir, 2009, 25(23):13516-13521.

Zhou et al., "Electrophoretic separation of DNA using a new matrix in uncoated capillaries," J. Chromatography A, 2005, 1083(1-2):173-178.

Abuchowski et al., "Alteration of Immunological Properties of Bovine Serum Albumin by Covalent Attachment of Polyethylene Glycol," J. Control. Rel., 1997, 252(11):3578-3581.

Abuchowski et al., "Effect of Covalent Attachment of Polyethylene Glycol on Immunogenicity and Circulating Life of Bovine," J Bio. Chem., 1976, 252(11):3582-3586.

Bahulekar et al., "Polyethyleneimine in Immobilization of Biocatalysts," Enzyme Microb. Technol., 1991, 13(11):858-868.

Barbosa et al., "Strategies for the One-Step Immobilization-Purification of Enzymes as Industrial Biocatalysts," Biotechnol. Adv., 2015, 33(5):435-456.

Caldwell et al., "Immobilization of Enzymes Based on Hydrophobic Interaction. I. Preparation and Properties of a Beta-Amylase Adsorbate," Biotechnol. Bioeng., 1976, 18(11):1573-1 588.

Chatterjee et al., "Signatures of Protein Thermal Denaturation and Local Hydrophobicity in Domain Specific Hydration Behavior: A Comparative Molecular Dynamics Study," Mol. Biosyst., 2016, 12(4):1139-1150.

CN Office Action in Chinese Appln. No. 201680021192.1, dated May 6, 2020, 5 pages.

Cobo et al., "Smart Hybrid Materials by Conjugation of Responsive Polymers to Biomacromolecules," Nat. Mater., 2014, 14(2):143-159.

Cummings et al., "Design of Stomach Acid-Stable and Mucin-Binding Enzyme Polymer Conjugates," Biomacromolecules, 2017, 18(2):576-586.

(56) References Cited

OTHER PUBLICATIONS

Dimitrov, "Therapeutic Proteins," Methods Mal. Biol., 2012, 899:1-26.
Gaudriault et al., "Selective Labeling of Alpha- or Epsilon-Amino Groups in Peptides by the Bolton-Hunter Reagent," Peptides, 1992, 13(6):1187-1192.
Gong et al., "Releasable Conjugation of Polymers to Proteins," Bioconjug. Chem., 2015, 26(7):1179-1181.
Green, "A Spectrophotometric Assay for Avidin and Biotin Based on Binding of Dyes by Avidin," Biochem. J., 1965, 94:23-24.
Griengl et al., "The Synthesis of Chiral Cyanohydrins by Oxynitrilases," Trends Biotechnol., 2000, 18(6):252-256.
Hanis et al., "Effect of Pegylation on Pharmaceuticals," Nat. Rev. Drug Discov., 2003, 2(3):214-221.
Hills, "Industrial use of lipases to produce fatty acid esters," Eur. J Lipid Sci. Technol., 2003, 105(10):601-607.
Isarov et al., ""Graft-to" Protein/Polymer Conjugates Using Polynorbornene Block Copolymers," Biomacromolecules, 2016, 17(2):641-648.
Jansen et al., "Inhibition of the Proteinase and Esterase Activities of Trypsin and Chymotrypsin by Diisopropyl Fluorophosphate; Crystallization of Inhibited Chymotrypsin," J Biol Chem., 1949, 179(1):189-199.
Jiang et al., "Structural and Dynamic Evolution of the Amphipathic N-terminus Diversifies Enzyme Thermostability in the Glycoside Hydrolase Family 12," Phys. Chem. Chem. Phys., 2016, 18(31):21340-21350.
Kim et al., "Activity-Based Assay of Matrix Metalloproteinase on Nonbiofouling Surfaces Using Time-of-Flight Secondary Ion Mass Spectrometry," Anal. Chem., 2008, 80(13):5094-5102.
Laurell et al., "Thiol-disulfide Interchange Chromatography Using Sepharose-linked Thiol Compounds to Separate Plasma Proteins," Anal. Biochem., 1997, 81(2):336-345.
Mahler et al., "Studies on Uricase. I. Preparation, Purification, and Properties of a Cuproprotein," J. Biol. Chem., 1955, 216(2):625-641.
Matyjaszewski et al., "Controlled Radical Polymerization, Copyright, Advisory Board, Foreword," ACS Symp. Ser., 1998, 685:258-83.
Matyjaszewski, "Bulk Atom Transfer Radical Polymerization," ACS Symp. Ser., 1998, 713:96-112.
Matyjaszewski, "Comparison and Classification of Controlled/Living Radical Polymerizations," ACS Symp. Ser., 2000, 768:2-26.
Matyjaszewski, "Controlled Radical Polymerization: State of the Art in 2008," ACS Symp. Ser., 2009, 1023:3-13.
Matyjaszewski, "Controlled Radical Polymerization: State-of-the-Art in 2011," ACS Symp. Ser., 2012, 1100:1-13.
Matyjaszewski, "Controlled/Living Radical Polymerization: State of the Art in 2002," ACS Symp. Ser., 2003, 854:2-9.
Matyjaszewski, "Organic-Inorganic Hybrid Polymers from Atom Transfer Radical Polymerization and Poly(dimethylsiloxane),"ACS Symp. Ser., 2000, 729:270-283.
Matyjaszewski, "The Preparation of Well-Defined Water Soluble-Swellable (Co)Polymers by Atom Transfer Radical Polymerization,"ACS Symp. Ser., 2000, 765:52-71.
Merrifield, "The role of the support in solid phase peptide synthesis," Br. Polym. J., 1984, 16:173-178.
Moon et al., "Enzyme-catalyzed reactions in ionic liquids," Korean J. Chem. Eng., 2006, 23(2):247-263.
Nieto et al., "Effects of Temperature and pH on the Regeneration of the Amino Groups of Ovalbumin After Modification With Citraconic and Dimethylmaleic Anhydrides," Biochim. Biophys. Acta., 1983, 749(2):204-210.
PCT International Preliminary Report on Patentability in International Appln. PCT/US2018/044859, dated Feb. 4, 2020, 9 pages.
PCT International Search Report and Written Opinion in International Appln. No. PCT/US19/44742, dated Oct. 16, 2019, 15 pages.
PCT International Search Report and Written Opinion in International Appln. No. PCT/US2018044859, dated Oct. 22, 2018, 12 pages.
PCT International Search Report and Written Opinion in International Appln. No. PCT/US19/44723, dated Dec. 5, 2019, 12 pages.
PCT Invitation to Pay Fees in International Appln. No. PCT/US19/44723, dated Sep. 20, 2019, 2 pages.
Porath, "Immobilized Metal Ion Affinity Chromatography," Protein Expr. Purif., 1992, 3(4):263-281.
Sanderova et al., "The N-terminal Region Is Crucial for the Thennostability of the G-domain of Bacillus Stearothermophilus EF-Tu," Biochim. Biophys. Acta., 2010, 1804(1):147-155.
Schulz et al., "Site-Specific Polymer Conjugation Stabilizes Therapeutic Enzymes in the Gastrointestinal Tract," Adv. Mater., 2016, 28(7):1455-1460.
Smolelis et al., "The Determination of Lysozyme," J. Bacterial., 1949, 58(6):731-736.
Tang et al., "N-succinimidyl propionate: Characterisation and optimum conditions for use as a tritium labelling reagent for proteins. Journal of Labelled Compounds and Radiopharmaceuticals," Journal of Labelled Compunds and Radiopharmaceuticals, 1983, 20(2):277-284.
Thomas et al., "Tailoring the pH dependence of enzyme catalysis using protein engineering," Nature, 1985, 318(6044):375-376.
Wang et al., "A Novel Mechanism of Protein Thermostability: A Unique N-terminal Domain Confers Heat Resistance to Fe/Mn-SODs," Sci. Rep., 2014, 4:7284.
Ward et al. "Thermostable Enzymes," Biotechnol. 1988, Adv., 6(1):39-69.
Wilson, "Synthesis and Applications of Protein/Peptide-Polymer Conjugates," Macromol. Chem. Phys., 2017, 218(9):1600595.
Yaphe, "The Use of Agarase From Pseudomonas Atlantica in the Identification of Agar in Marine Algae (*Rhodophyceae*)," Can. J Microbial., 1957, 3(7):987-993.
Zeikus et al., "Thermozymes: biotechnology and structure—function relationships," Trends Biotechnol., 1996, 14(6):183-190.
Zhao et al., "Synthesis of well-defined protein-polymer conjugates for biomedicine," Polymer, 2015, 66:A1-A10.
Hucknall et al., "In Pursuit of Zero: Polymer Brushes that Resist the Adsorption of Proteins," Advanced Materials, 2009, 21(23):2441-2446.
Kreutzer, "Atom-Transfer Radical Polymerization: New Method Breathes Life Into ATRP," Nature Reviews Chemistry, 2018, 2(2):0111.
U.S. Appl. No. 17/284,837, filed Apr. 13, 2021, Hironobu Murata.
U.S. Appl. No. 14/785,868, filed Oct. 21, 2015, Alan J. Russell.
U.S. Appl. No. 15/026,093, filed Mar. 30, 2016, Alan J. Russell.
U.S. Appl. No. 15/549,852, filed Aug. 9, 2017, Alan J. Russell.
U.S. Appl. No. 16/477,843, filed Jul. 12, 2019, Alan J. Russell.
U.S. Appl. No. 16/635,343, filed Jan. 30, 2020, Hironobu Murata.
U.S. Appl. No. 17/264,519, filed Jan. 29, 2021, Alan J. Russell.
U.S. Appl. No. 17/264,455, filed Jan. 29, 2021, Alan J. Russell.

\* cited by examiner

ENZYME-ASSISTED ATRP PROCEDURES

CROSS-REFERENCE TO RELATED APPLICATIONS

This application claims priority from U.S. Provisional Application Ser. No. 62/764,221, filed Jul. 23, 2018, which is incorporated herein by reference in its entirety.

TECHNICAL FIELD

The present invention discloses methods for conducting atom transfer radical polymerization (ATRP) in the presence of oxygen using, for example, coordinated enzymatic activities to remove or utilize oxygen during controlled polymerization procedures.

BACKGROUND

ATRP is a controlled radical polymerization process that allows effective control over the molecular weight (MW) of the formed polymer, preparation of polymers with narrow molecular weight distributions (dispersity, D), incorporation of precisely placed functionalities within the polymer, and fabrication of polymers with various architectures in addition to the synthesis of well-defined composite materials. ATRP is one of the most widely used Controlled Radical Polymerization (CRP) or Reversible-Deactivation Radical Polymerization (RDRP) techniques, due to the range of (co)monomers that can be polymerized and the spectrum of initiators that allow the synthesis of polymers with multiple complex architectures (Tsarevsky and Matyjaszewski, *J. Am. Chem. Soc.* 2014, 136:6513-6533). Over time, the fundamental ATRP procedure has been expanded to provide diverse experimental procedures that allow for a reduction in the amount of catalyst required for polymerization, and permit the reaction to be conducted in a range of media, including the synthesis of polymers under homogeneous and heterogeneous aqueous conditions (Averick et al., *ACS Macro Letters* 2012, 1:6-10). This allowed for the use of ATRP to develop an area of research based on the synthesis and modification of biological systems (Pan et al., *Angew. Chem. Int. Ed.* 2017, 56:2740-2743; Cummings et al., *ACS Macro Letters* 2016, 5:493-497; Qi et al., *Nat. Biomed. Eng.* 2016, 1:1-12; and Averick et al., *J. Control. Release* 2015, 205:45-57).

During the course of an ATRP, there often is an accumulation of the deactivator form of the catalyst as a result of bimolecular termination. This increase in deactivator concentration can change the equilibrium between the dormant and active species, and eventually the polymerization rate can slow or even stop at incomplete conversion if incorrect polymerization conditions are selected. This limitation was initially overcome by adding high concentrations of relatively less active catalysts. More recent developments have overcome this phenomenon through the use of reducing agents that can re-form the activator and allow higher (to almost complete) conversion of monomers to be realized, with much lower concentrations of added active catalyst complexes (Bultz et al., *Polymer* 2016, 106:313-319).

Historically, industrial scale radical-based polymerizations were performed in anaerobic environments ensuring that air did not penetrate the reaction mixture, as propagating radicals can react with oxygen and form stable peroxy radicals and hydroperoxides that react very slowly with monomers, thus quenching chain growth. Although ATRP displays a degree of robustness that permits the use of protic solvents (Simakova et al., *Macromol.* 2012, 45:6371-6379), high tolerance to oxygen represents a major challenge, particularly in small scale laboratory polymerizations. Oxygen is a diatomic molecule with two unpaired electrons in separate orbitals in its outer shell. Oxygen captures radicals in a very efficient manner, and thus can stop the propagation of radical polymerizations. Due to this reactivity and its abundance in the atmosphere, oxygen is the most undesired radical scavenger in polymer synthesis. To address this limitation, degassing for long periods of time with inert gasses, use of a glove box or more complicated techniques that are not always scalable (e.g., "freeze, pump, thaw") are regularly used for the effective removal of oxygen in small scale laboratory procedures. Until now, however, large scale, economic methods that allow the execution of RDRP procedures (including ATRP) in oxygen-rich environments have not been achieved.

SUMMARY

This document is based, at least in part, on the development of materials and methods that permit efficient and effective ATRP reactions in the presence of oxygen. For example, this document is based, at least in part, on the discovery that fully-oxygen tolerant ATRP can be enabled by the continuous conversion of oxygen to carbon dioxide, catalyzed by the interaction of glucose oxidase (GOx) or another oxidase (e.g., pyranose-2-oxidase; P2Ox) with glucose or another oxidase substrate (e.g., another sugar) in the presence of a reactive oxygen species (ROS) scavenger (e.g., sodium pyruvate or another radical mediator, such as horseradish peroxidase; HRP), as sequential sacrificial substrates that remove the formed hydrogen peroxide ($H_2O_2$) from the reaction. This document also is based, at least in part, on the discovery that "oxygen fueled" enzymatic ATRP can be driven by consumption of oxygen to enzymatically generate radicals in situ and initiate an enzymatic-Initiators for Continuous Activator Regeneration-(ICAR-)ATRP. Further, this document is based, at least in part, on the discovery that nano-molar concentrations of enzymes and ppm amounts of Cu in a vessel completely open to air under physiologically relevant conditions can provide excellent control over the polymerization of biocompatible monomers, generating bioconjugates linked to polymer segments with controlled high molecular weight and low D in less than an hour. In addition, this document is based, at least in part, on the discovery that surface-initiated ATRP (SI-ATRP) can be conducted from substrates of any topology in an open vessel in the presence of GOx, glucose, and a ROS scavenger.

Thus, in some embodiments, this document provides methods for oxygen-tolerant ATRP that include using GOx and glucose to convert oxygen to carbon dioxide in the presence of a ROS scavenger (e.g., sodium pyruvate) or another radical mediator (e.g., HRP) to remove hydrogen peroxide from the reaction. In some embodiments, this document also provides "oxygen fueled" enzymatic ATRP methods in which the reaction is driven by consumption of oxygen to enzymatically generate radicals in situ and initiate enzymatic-ICAR-ATRP. In some embodiments, this document provides ATRP methods that include the use of nano-molar concentrations of enzymes and ppm amounts of Cu in a vessel that is open to air under physiologically relevant conditions. Further, in some embodiments, this document provides SI-ATRP methods conducted from a solid substrate in an open vessel in the presence of GOx, glucose, and a ROS scavenger.

In a first aspect, this document features a method for polymerizing free radically copolymerizable monomers. The method can include combining (a) a deoxygenated polymerization medium containing (i) a transition metal catalyst or metal-free organic complex that can participate in a redox reaction, and (ii) an initiator including one or more redox transferable atoms or groups; (b) an oxygen scavenger; and (c) a ROS scavenger. The polymerization medium can be an aqueous medium. The method can be carried out in a reactor with a limited head space comprising air. The method can be carried out in a reactor open to the atmosphere. The oxygen scavenger can include glucose and GOx. The ROS scavenger can include one or more of pyruvate, horseradish peroxidase, an α-keto-acid, catalase, and a catalase-like enzyme selected from the group consisting of ascorbate peroxidase, cytochrome C peroxidase, haloperoxidase, hemoprotein, glutathione peroxidase, glucose oxidase, laccase, monoamine oxidase, cytochrome P450 oxidase, NADPH oxidase, xanthine oxidase, L-gulonolactone oxidase, and superoxide dismutase. In some cases, the oxygen scavenger can include glucose and GOx, and the ROS scavenger can include one or more of pyruvate, horseradish peroxidase, an α-keto-acid, catalase, and a catalase-like enzyme selected from the group consisting of ascorbate peroxidase, cytochrome C peroxidase, haloperoxidase, hemoprotein, glutathione peroxidase, glucose oxidase, laccase, monoamine oxidase, cytochrome P450 oxidase, NADPH oxidase, xanthine oxidase, L-gulonolactone oxidase, and superoxide dismutase. The initiator can be a bioresponsive molecule with one or more site specific functional initiators. The bio-responsive molecule can be a protein, polypeptide, polynucleotide, aptamer, nucleic acid, or other biomolecule that is incorporated into the formed conjugate with the polymer grown from the site-specific incorporated initiator site(s). The method can include transition metal-mediated controlled polymerizing of vinyl monomers in an aqueous based polymerization medium. The method can be an ICAR-ATRP, and a free radical source can be generated in situ by reaction of an enzyme with the product of the oxygen scavenging reaction. The method can be a photo-ATRP, where a free radical source is generated in situ by photo-based reaction of a reducing agent, and where oxygen is removed by reaction of an enzyme with the product of the oxygen scavenging reaction. The method can be an activator regenerated by electron transfer (ARGET) ATRP, where a free radical source is generated in situ by reaction of a reducing agent, and where oxygen is removed by reaction of an enzyme with the product of the oxygen scavenging reaction. The method can be a surface-initiated polymerization. The oxygen scavenger can include glucose and GOx, where the GOx is immobilized on a solid substrate (e.g., glass, metal, or plastic).

In another aspect, this document features an oxygen-driven ATRP method. The method can include combining (a) a deoxygenated polymerization medium containing (i) copper at a concentration less than 1500 ppm, wherein the copper is capable of participating in a redox reaction, and (ii) a halogen-containing initiator having one or more redox transferable atoms or groups; (b) an oxygen scavenger comprising glucose and GOx; and (c) a ROS scavenger, where the ROS scavenger can be a pyruvate, horseradish peroxidase, an α-keto-acid, a catalase, or a catalase-like enzyme, and where the concentrations of the oxygen scavenger and the ROS scavenger are sufficient to provide a continuous source of radicals for controlled polymerization from the halogen-containing initiator. The polymerization medium can be an aqueous medium. The method can be carried out in a reactor with a limited head space comprising air. The method can be carried out in a reactor open to the atmosphere. The ROS scavenger can include a catalase-like enzyme selected from the group consisting of ascorbate peroxidase, cytochrome C peroxidase, haloperoxidase, hemoprotein, glutathione peroxidase, glucose oxidase, laccase, monoamine oxidase, cytochrome P450 oxidase, NADPH oxidase, xanthine oxidase, L-gulonolactone oxidase, and superoxide dismutase. The GOx can be immobilized on a solid substrate (e.g., glass, metal, or plastic).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

The figures assist in clarifying certain embodiments of the invention but are not intended to limit the invention to the examples described in the figures, as other monomers and other ratios of reagents, and indeed other reagents, can be employed in the disclosed oxygen tolerant, enzymatically activated polymerization methods.

FIG. 10A is a kinetic plot, FIG. 10B is a graph plotting $M_n$ and Đ evolution with conversion, and FIG. 10C is a series of GPC curves at various time points.

DETAILED DESCRIPTION

Figure 1:
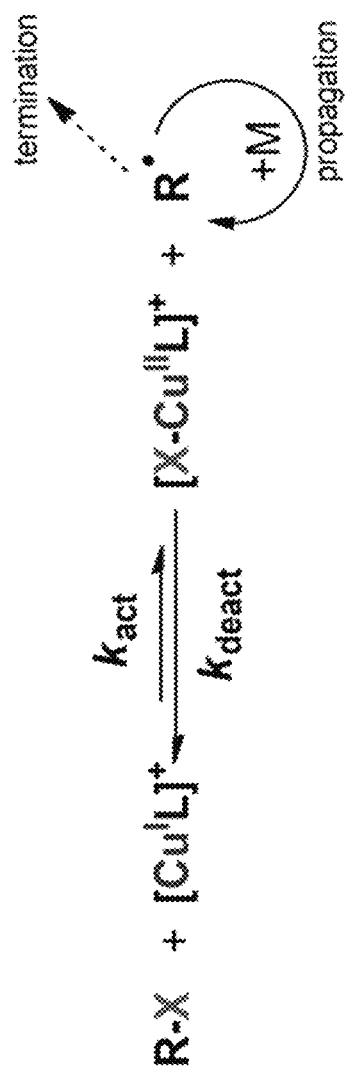
FIG. 1 is a scheme showing a generally accepted mechanism for ATRP.

ATRP is a type of a reversible-deactivation radical polymerization, and is a means of forming a carbon-carbon bond with a transition metal catalyst. ATRP typically employs an alkyl halide (R—X) initiator and a transition metal complex (e.g., a complex of Cu, Fe, Ru, Ni, or Os) as the catalyst. In an ATRP reaction, the dormant species is activated by the transition metal complex to generate radicals via electron transfer. Simultaneously, the transition metal is oxidized to a higher oxidation state. This reversible process rapidly establishes an equilibrium that predominately is shifted to the side with very low radical concentrations. The number of polymer chains is determined by the number of initiators, and each growing chain has the same probability of propagating with monomers to form living/dormant polymer chains (R-Pn-X). As a result, polymers with similar molecular weights and narrow molecular weight distribution can be prepared.

The basic ATRP process and a number of improvements are described elsewhere. See, for example, U.S. Pat. Nos. 5,763,546; 5,807,937; 5,789,487; 5,945,491; 6,111,022; 6,121,371; 6,124,411; 6,162,882; 6,624,262; 6,407,187; 6,512,060; 6,538,091; 6,541,580; 6,624,262; 6,627,314; 6,759,491; 6,790,919; 6,887,962; 7,019,082; 7,049,373; 7,064,166; 7,125,938; 7,157,530; 7,332,550; 7,407,995; 7,572,874; 7,678,869; 7,795,355; 7,825,199; 7,893,173; 7,893,174; 8,252,880; 8,273,823; 8,349,410; 8,367,051; 8,404,788; 8,445,610; 8,816,001; 8,865,795; 8,871,831; 8,962,764; 9,243,274; 9,410,020; 9,447,042; 9,533,297; and 9,644,042; and Publication Nos. 2014/0183055; 2014/0275420; and 2015/0087795, all of which are incorporated herein by reference to provide background and definitions for the present disclosure.

ATRP also is discussed in a number of publications and reviewed in several book chapters. See, e.g., Matyjaszewski and Zia, *Chem. Rev.* 2001, 101:2921-2990; Qiu et al., *Prog. Polym. Sci.* 2001, 26:2083-2134; Wang and Matyjaszewski, *J. Am. Chem. Soc.* 1995, 117:5614-5615; Coessens et al., *Prog. Polym. Sci.* 2001, 26:337-377; Braunecker and Matyjaszewski, *Prog. Polym. Sci.* 2007, 32:93-146; Matyjaszewski, *Macromol.* 2012, 45:4015-4039; Schroder et al., *ACS Macro Letters* 2012, 1:1037-1040; Matyjaszewski and Tsarevsky, *J. Am. Chem. Soc.* 2014, 136:6513-6533; and Kamigaito et al., *Chem Rev* 2001, 101:3689-3746. Indeed, ATRP can control polymer composition, topology, and position of functionalities within a copolymer (Coessens et al., supra; *Advances in Polymer Science;* Springer Berlin/Heidelberg: 2002, Vol. 159; Gao and Matyjaszewski, *Prog. Polym. Sci.* 2009, 34:317-350; Blencowe et al., *Polymer* 2009, 50:5-32; Matyjaszewski, *Science* 2011, 333:1104-1105; and *Polymer Science: A Comprehensive Reference*, Matyjaszewski and Martin, Eds., Elsevier: Amsterdam, 2012; pp 377-428).

Monomers and initiators having a variety of functional groups (e.g., allyl, amino, epoxy, hydroxy, and vinyl groups) can be used in ATRP. ATRP has been used to polymerize a wide range of commercially available monomers, including various styrenes, (meth)acrylates, (meth)acrylamides, N-vinylpyrrolidone, acrylonitrile, and vinyl acetate as well as vinyl chloride (Qiu and Matyjaszewski, *Macromol.* 1997, 30:5643-5648; Matyjaszewski et al, *J. Am. Chem. Soc.* 1997, 119:674-680; Teodorescu and Matyjaszewski, *Macromol.* 1999, 32:4826-4831; Debuigne et al., *Macromol.* 2005, 38:9488-9496; Lu et al., *Polymer* 2007, 48:2835-2842; Wever et al., *Macromol.* 2012, 45:4040-4045; and Fantin et al., *J. Am. Chem. Soc.* 2016, 138:7216-7219). Non-limiting examples of particular monomers that can be used in ATRP reactions include (oligo(ethylene glycol) methacrylate) (POEGMA), poly(2-dimethylaminoethyl methacrylate) (PDMAEMA), poly(sulfobetaine methacrylate) (PSBMA), poly (2-(methylsulfinyl)ethyl acrylate (PMSEA), oligo(ethylene oxide) methyl ether methacrylate (OEOMA), and (hydroxyethyl)methacrylate (HEMA).

A scheme for a generally accepted ATRP mechanism is shown in FIG. 1. In a classic ATRP, a copper-amine complex in its lower oxidation state (a $Cu^I L^+$ complex) activates a low fraction of an added alkyl halide initiator (R—X) or a dormant chain end ($P_n$—X), forming a propagating radical and the deactivator catalyst complex in the higher oxidation state, $X-CO^{II}L^+$. After the addition of a few monomer units, the growing radicals are reverted back to their dormant state ($P_n$—X), hence minimizing termination reactions and providing concurrent growth of all chains. More recent developments include metal-free ATRP procedures (Jockusch and Yagci, *Polymer Chemistry* 2016, 10; 1039/c6py01410k), which also can be applied to metal free photo-ATRP (Matyjaszewski, Abstracts of Papers, March 2018 ACS Meeting, POLY-157; and Li et. al., *ACS Energy Letters* 2018, 3:20-27).

Enzymes are the most potent biological catalysts. One of their main functions in the body is the assembly of monomers (e.g., nucleic bases, saccharides and amino-acids) into biopolymers such as DNA, carbohydrates and proteins. This assembly is initiated by a signal or stimulus (air, light, heat, stress, etc.) that triggers the action of enzymatic interactions through the cells until the demand for the desired biopolymer is satisfied. One class of enzymes that can activate biological pathways includes copper-containing metalloenzymes that serve as oxido-reductases (Boal and Rosenzweig, *Chemical Reviews* 2009, 109(10):4760-4779), such as laccase, cytochrome c, and superoxide dismutase, or copper transporters including copper chaperones (Davis and O'Halloran, *Nature Chem. Bio.* 2008, 4(3):148-151) and transmembrane proteins (Robinson and Winge, *Ann. Rev. Biochem.* 2010, 79(1):537-562) designed to bring copper from one protein to another or across the cell membrane. Enzymes such as catalase can convert hydrogen peroxide into water and oxygen, as can pyruvic acid and other α-keto-acids (Asmus et al., *J. Phys. Chem. A.* 2015, 119: 966-977).

GOx can be an effective scavenger for oxygen in free radical polymerization (FRP) (Oytun et al., *J. Polym. Sci. Part A, Polym. Chem.* 2013, 51:1685-1689) and in Enzyme-assisted Reversible Addition-Fragmentation chain Transfer (Enz-RAFT) polymerization (Chapman et al., *Angew. Chem. Int. Ed.* 2016, 55:4500-4503; Chapman et al., *Macromol.* 2014, 47:8541-8547; and Gormley et al., *Nano Letters* 2014, 14:6368-6373). The feasibility of polymerization in open air in the presence of GOx also has been demonstrated (Lv et al., *J. Polym. Sci. Part A, Polym. Chem.* 2017, 55:164-174; and Tan et al., *Macromolecules* 2017, 50:5798-5806). In these reports, however, where the generation of extra radicals was not intended (Iwata et al., *J. Polym. Sci. Part A, Polym. Chem.* 1991, 29:1217-1218), the production of hydrogen peroxide as a side product was ignored even though hydrogen peroxide had been reported to remove the Reversible Addition-Fragmentation chain Transfer (RAFT) end groups from polymers (Jesson et al., *Macromolecules* 2017, 50:182-191).

Hydrogen peroxide is not a side product that can be ignored in an ATRP, as it is well documented that many transition metals, including those required as catalysts for ATRP, undergo Fenton-like reactions (Pham et al., *J. Catalysis* 2013, 301:54-64) in the presence of hydrogen peroxide (Helsel and Franz, *Dalton Transactions* 2015, 44:8760-8770; Shan et al., *Chem. Commun.* 2016, 52:2087-2090; and Lee et al., *Environ. Sci. Technol.* 2016, 50:8231-8238), thereby generating many more radical initiators than those accounted for in the planned reaction. This phenomenon precludes controlled polymerization with the ability to prepare polymers having predetermined α-functionality and targeted molecular weight with narrow dispersity.

As disclosed herein, GOx can inexpensively degas solution phase polymerization reactions enzymatically by consuming oxygen as it oxidizes glucose. The examples discussed herein, in which GOx was the only added enzyme, confirmed that generated hydrogen peroxide resulted in poor control over an ATRP, which is in contrast to the reports for FRP and RAFT polymerizations cited above. The methods provided herein extend the ability to use GOx for oxygen removal from an ATRP, as they utilize reaction conditions that avoid any reaction between hydrogen peroxide and the frequently employed copper- or iron-based catalysts.

Figure 2:
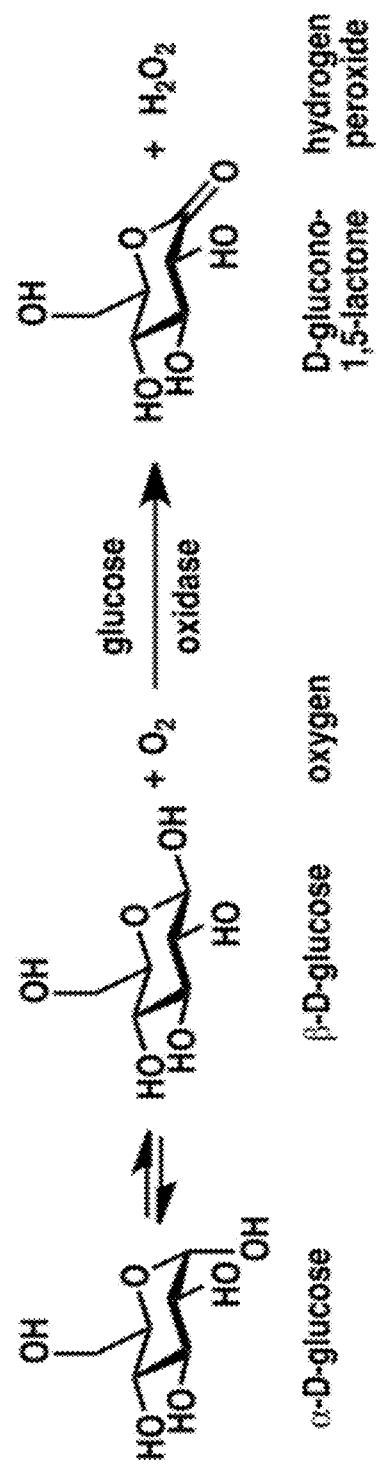
FIG. 2 is a scheme illustrating the reaction of GOx with oxygen.
Figure 3:
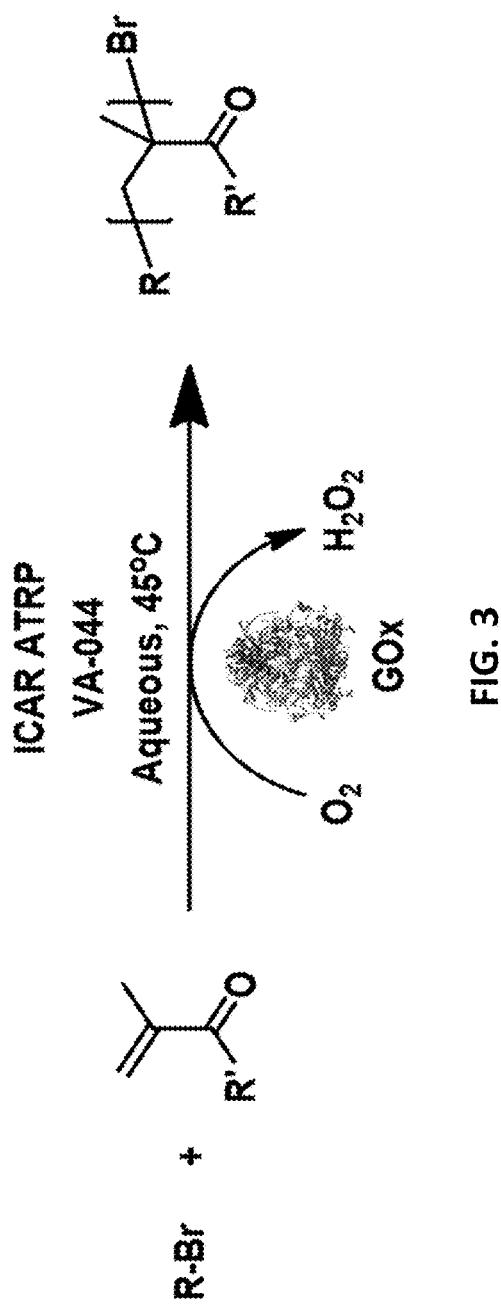
FIG. 3 is a scheme showing the use of GOx-catalyzed oxygen removal in an ICAR ATRP.

For example, to address the generation of free radicals due to the use of GOx-catalyzed oxygen removal through reaction with glucose (FIG. 2), an initial series of experiments was conducted under ICAR-ATRP conditions (FIG. 3). In these studies, the generated peroxide radicals could act to reactive any formed X—$Cu^{II}$/L complex, reducing it to an activator $Cu^{I}$/L complex with concurrent formation of a new ATRP initiator, R—X.

Figures 10A, 10B, 10C:
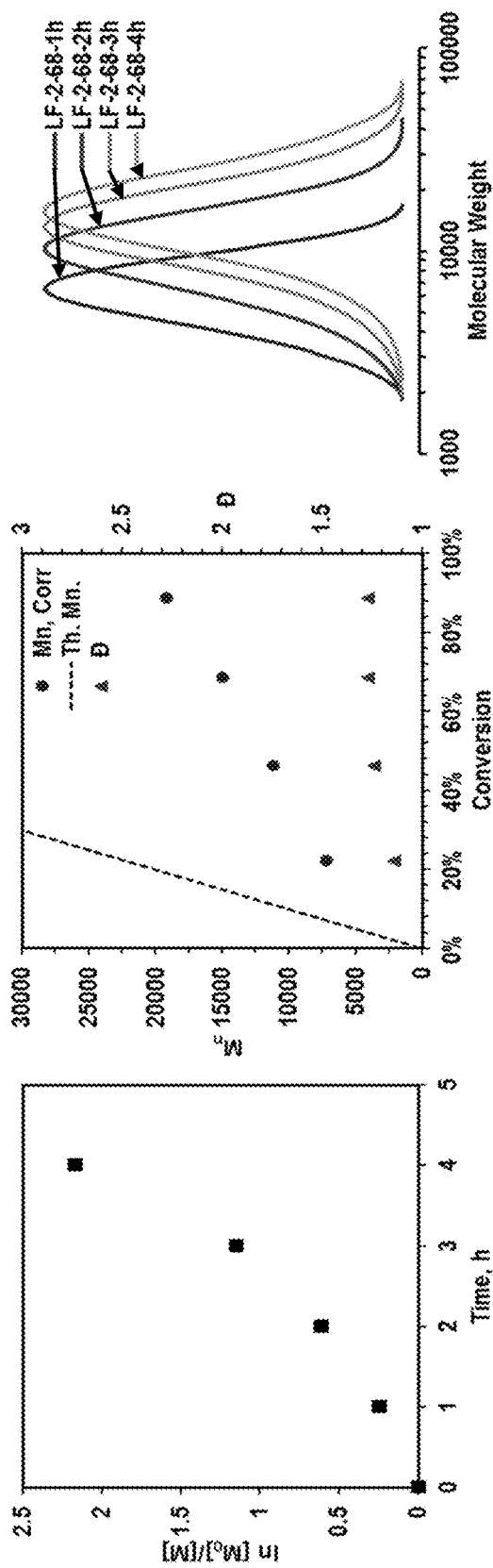
FIGS. 10A-10C illustrate the kinetics of GOx deoxygenated aqueous ICAR-ATRP polymerization of oligo(ethylene oxide) methyl ether methacrylate, molecular weight 500 ($OEOMA_{500}$).

FIGS. 10A-10C and Example 1A show the results of polymerization of two water-soluble, biocompatible monomers, $OEOMA_{500}$ and HEMA. Both reactions showed increased conversion with time and increasing MW with conversion. The reactions were conducted with 1000 ppm of Cu and a target $DP_n$=200. After 4 hours, conversion reached 88%, but the experimental molecular weight ($M_{n, exp}$) was much lower than the theoretical molecular weight ($M_{n, Th}$) even though the dispersity was acceptable. The results are presented in TABLE 1. Various polymerization parameters were examined, and it was concluded that a significant number of new chains were being generated from a Fenton like reaction between the Cu(I) complex and the hydrogen peroxide product of the oxygen scavenging reaction.

Figure 4:
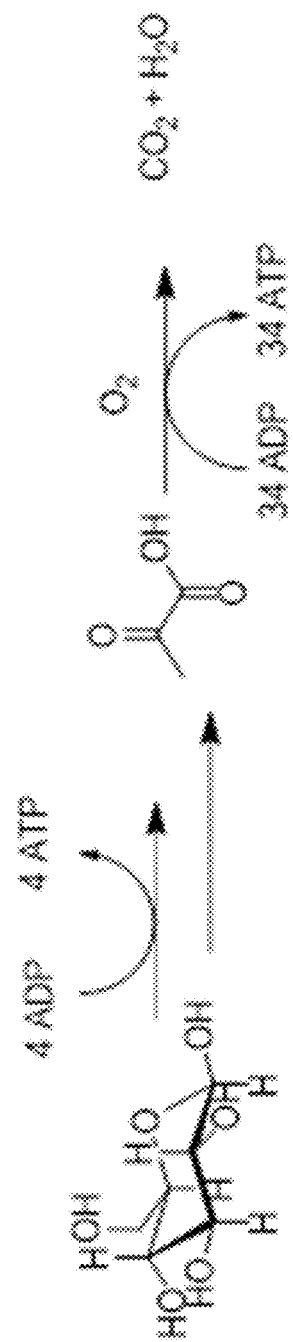
FIG. 4 is a scheme illustrating aerobic respiration using adenosine diphosphate (ADP), illustrating the consumption of $O_2$ present in the reaction medium and flask and the release of $CO_2$.

This obstacle was resolved by developing a novel approach to almost immediately remove the hydrogen peroxide from the reaction medium prior to its interaction with the copper catalyst. The approach taken was an aerobic respiration-like process using glucose and oxygen as starting materials that, after a cycle of several enzymatic reactions, results in electron transport and formation of $CO_2$ and adenosine triphosphate (ATP; FIG. 4). In the aerobic respiration cycle, glucose goes through a series of glycolytic transformations to yield pyruvate and ATP. Pyruvate then reacts with oxygen to generate acetyl-CoA that in the Krebs cycle becomes $CO_2$ and forms more ATP molecules. Pyruvate is an excellent hydrogen peroxide scavenger in the human body; the reaction of sodium pyruvate with hydrogen peroxide is fast and efficient. Experiments were conducted with GOx and sodium pyruvate, which through a cascade of reactions consumed $O_2$ present in the reaction medium and flask, releasing $CO_2$.

Figure 5:
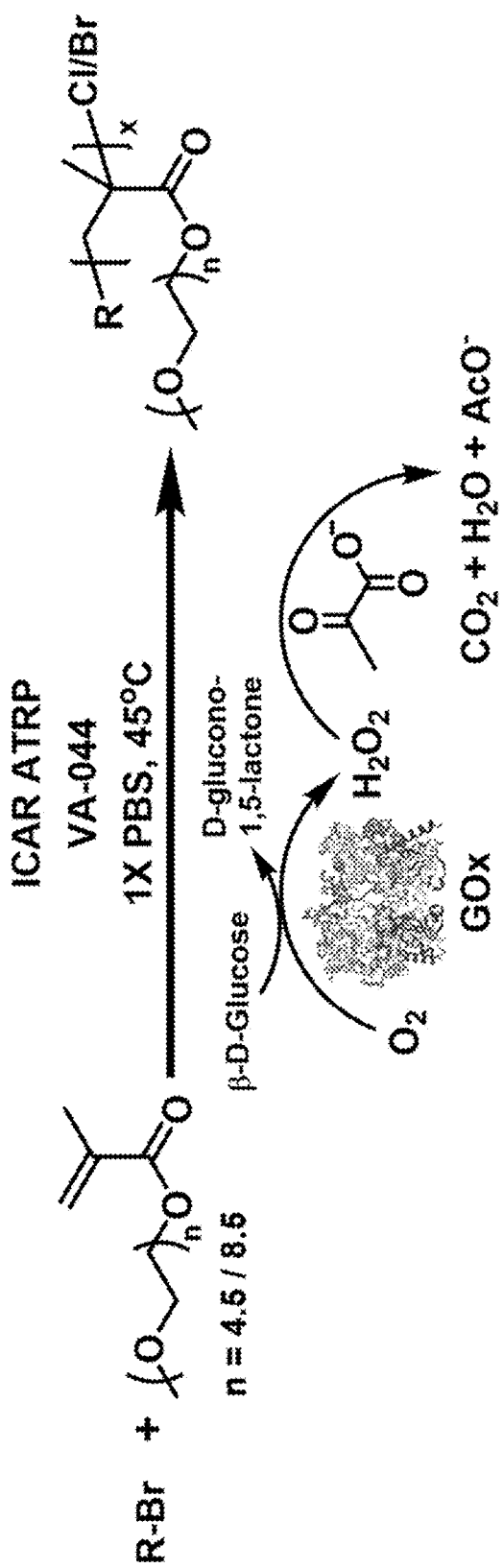
FIG. 5 is a scheme showing oxygen tolerant ICAR-ATRP.

In some embodiments of the polymerization system disclosed herein, glucose and oxygen are catalyzed by GOx into D-glucono-1,5-lactone and hydrogen peroxide, allowing for radical propagation in the presence of air. The hydrogen peroxide then can react extremely quickly with pyruvate to yield $CO_2$+acetate+water. Taking this procedure into consideration results in the mechanism shown in FIG. 5 for the exemplary aqueous ICAR-ATRP of various methacrylate monomers. In addition to being a potential "green approach" for the synthesis of polymers in the presence of air, the products of the enzymatic elimination of oxygen can be considered commodity chemicals. For example, acetates frequently are used as a feedstock in the chemical industry, and the need for metal acetates is millions of tons annually. In addition, since $CO_2$ is denser than air, it can provide a protective layer between the reaction mixture and the atmosphere, thereby providing an oxygen insulating layer at the surface of the polymerization.

This system, which included using a combined enzymatic cascade, allowed the controlled polymerization of $OEOMA_{500}$ via aqueous ICAR-ATRP at different targeted DPs, confirming that hydrogen peroxide was successfully removed from the reaction. Polymers with narrow dispersity (1.09≥Đ≤1.2) were obtained, even when high DPs were targeted. After the procedure was optimized, well controlled polymerizations with a good match between theoretical $M_n$ and $M_n$ measured by corrected GPC ($M_{nGPC}$) were obtained (TABLE 2). Successful chain extension by the direct addition of $OEOMA_{300}$ monomers to the vial after the first block reached ~85% conversion, monitored by NMR, demonstrated the retention of chain end functionality and hence the control of the polymerization with low dispersity (Đ=1.3).

Figure 12B:
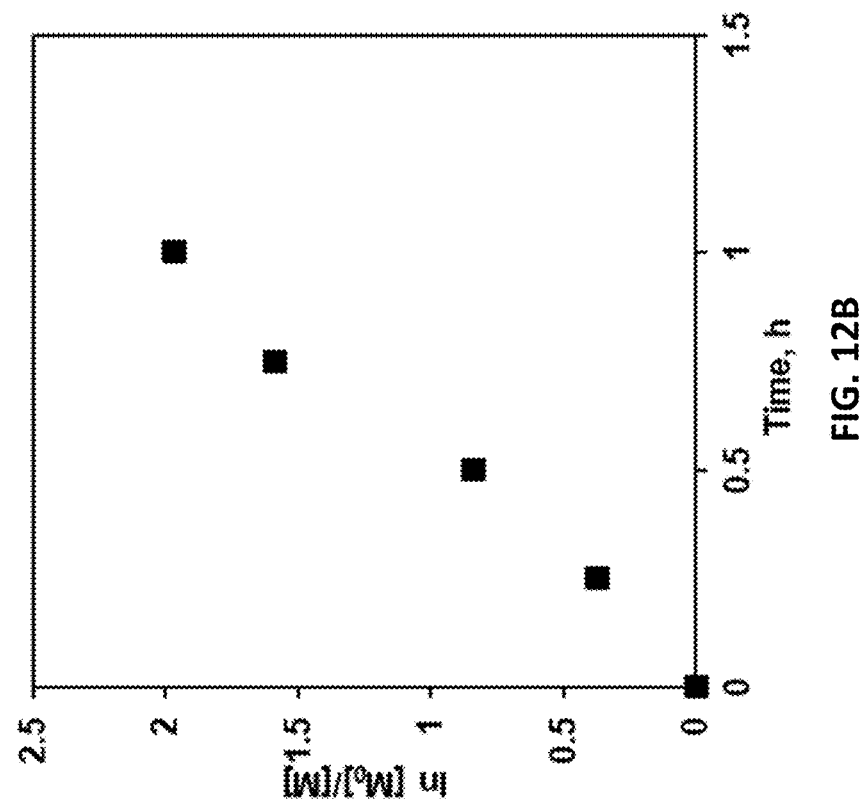
FIG. 12B is a graph plotting reaction kinetics.
Figure 12A:
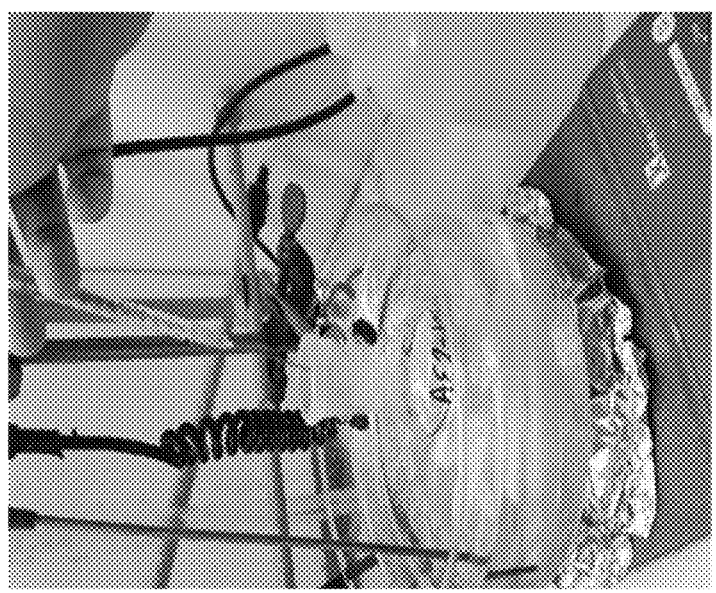
FIG. 12A is an image showing a reaction carried out in an open 50 ml flask.
Figure 12C:
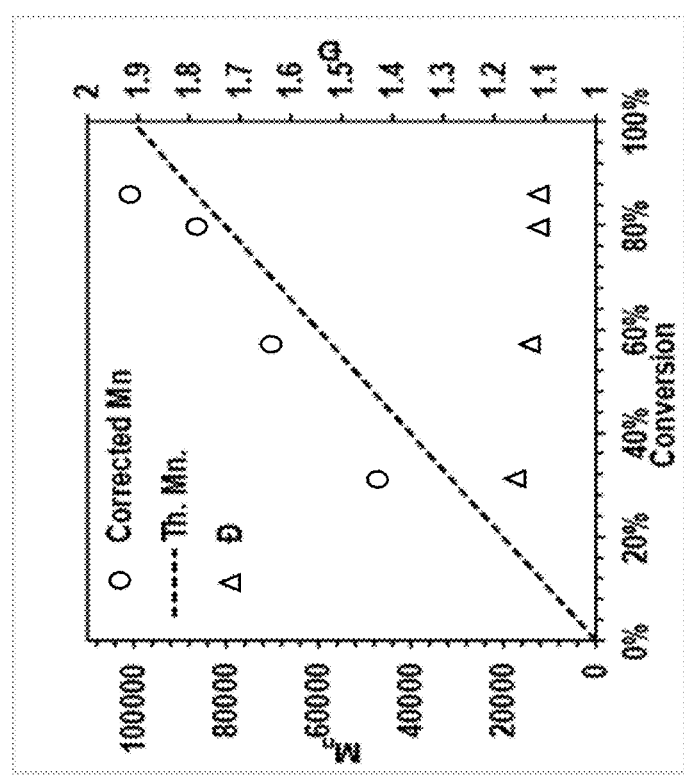
FIG. 12C is a graph plotting evolution of the $M_n$ and dispersity of the generated polymers.

The developed conditions resulted in robust, broadly applicable procedures, indicating that larger scale polymerizations can readily be carried out. The fact that controlled ATRP reactions were accomplished in open air vials indicated that the polymerization conditions were scalable to larger volumes. This was exemplified in the laboratory by using larger containers (50 mL), which provided polymers with low Đ and molecular weights identical to the theoretical targets in the model reactions, FIG. 12.

Any appropriate concentrations of GOx (or other oxidase), glucose (or other oxidase substrate), ROS scavenger can be used in the methods provided herein. In general, the concentrations of these components can be sufficient to provide a continuous source of radicals for controlled polymerization from the initiator. In some cases, suitable concentrations of oxidase (e.g., GOx) can range from about 1 nM to about 500 mM (e.g., about 1 nM to about 10 nM, about 10 nM to about 100 nM, about 100 nM to about 500 nM, about 500 nM to about 1 about 1 μM to about 10 about 10 μM to about 100 about 100 μM to about 1 mM, about 1 mM to about 10 mM, about 10 mM to about 100 mM, or about 100 mM to about 500 mM). In some cases, suitable concentrations of oxidase substrate (e.g., glucose) can range from about 1 mM to about 1 M (e.g., about 1 mM to about 10 mM, about 10 mM to about 100 mM, about 100 mM to about 300 mM, about 200 mM to about 400 mM, about 300 mM to about 500 mM, or about 500 mM to about 1 M). In some cases, suitable concentrations of ROS scavenger can range from about 100 µM to about 1 M (e.g., about 100 µM to about 1 mM, about 1 mM to about 10 mM, about 10 mM to about 100 mM, about 100 mM to about 300 mM, about 200 mM to about 400 mM, about 300 mM to about 500 mM, or about 500 mM to about 1 M).

In order to probe the feasible modification of biological systems using this novel enzymatic cascade model, the synthesis of protein-polymer biohybrids was examined via "self-promoted" polymerization of GOx to demonstrate that the enzymes remain catalytically active during and after the polymerization procedure. Two different ATRP initiators—one containing HO-EBiB-like moieties and the other containing BPAA-like moieties—were synthesized with cleavable ester functionalities in their structures, and were tethered separately onto the surface of GOx using—NHS chemistry in PBS (Averick et al. 2015, supra). The polymerizations proceeded following air breathing ICAR-ATRP conditions. After the polymerization of OEOMA$_{500}$ monomer was finished, the polymer was cleaved from the enzymatic structure under basic conditions and analyzed by GPC. The dispersity obtained from the cleaved polymers was close to Đ~1.17, confirming a well-controlled grafting from reaction.

Figure 6:
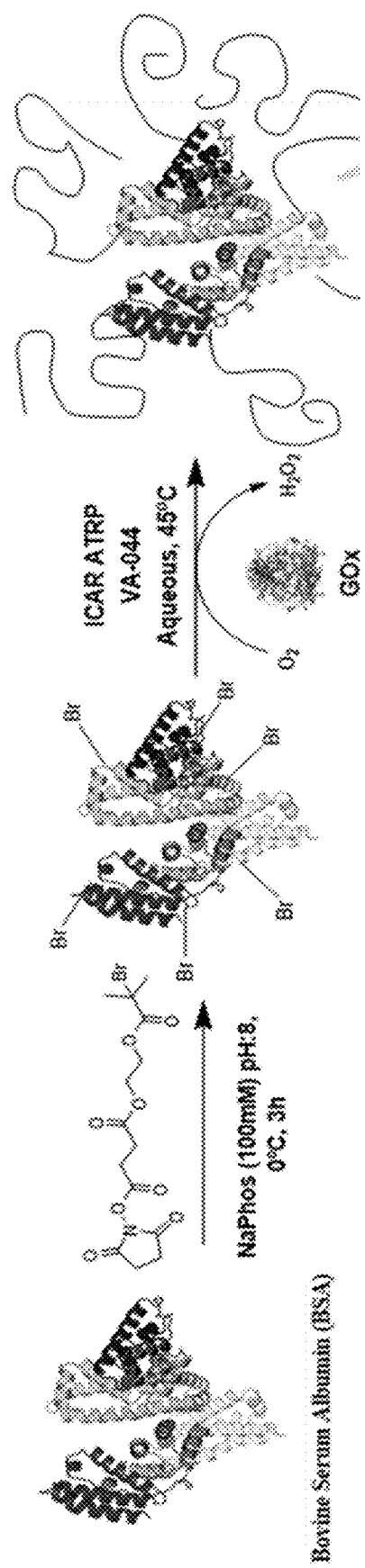
FIG. 6 is a scheme showing a procedure for grafting from BSA followed by polymer cleavage.

Since the conditions of this enzyme-initiated ATRP are considered biocompatible, a protein-polymer bioconjugate was synthesized using a Bovine Serum Albumin (BSA) based macroinitiator, generated as described elsewhere (Averick et al., supra). The α-bromoisobutyrate (iBBr) groups containing ester tethers were incorporated via NHS-chemistry on the accessible lysine units on the BSA molecules. After the polymerization of OEOMA$_{500}$ using this "oxygen fueled" ATRP system was complete (FIG. 6), the polymer was cleaved from the protein structure under basic conditions (5% NaOH) and analyzed using THF GPC. The results confirmed that the biohybrid (BSA-b-POEOMA) was prepared in a well-controlled manner, providing conjugated polymer chains with $M_n$=63,100 and Đ=1.18. The conditions for the grafting from reaction are shown in TABLE 3. This example confirmed that novel air tolerant ATRP procedure can be applied to the formation of bio-conjugated molecules with well-defined copolymer conjugates.

In addition to pyruvate salt or pyruvic acid, other biocompatible organic and inorganic-based radical scavengers can be used in the methods provided herein. Suitable radical scavengers include, without limitation, thiocarboxylates and other sources of sulfur carboxylate compounds, and catalase-like enzymes. Examples of suitable catalase-like enzymes include, without limitation, ascorbate peroxidase, cytochrome C peroxidase, haloperoxidase, hemoprotein, glutathione peroxidase and the oxidoreductase family—glucose oxidase, laccase, monoamine oxidase, cytochrome P450 oxidase, NADPH oxidase, xanthine oxidase, L-gulonolactone oxidase, and others, such as superoxide dismutase.

Figure 7:
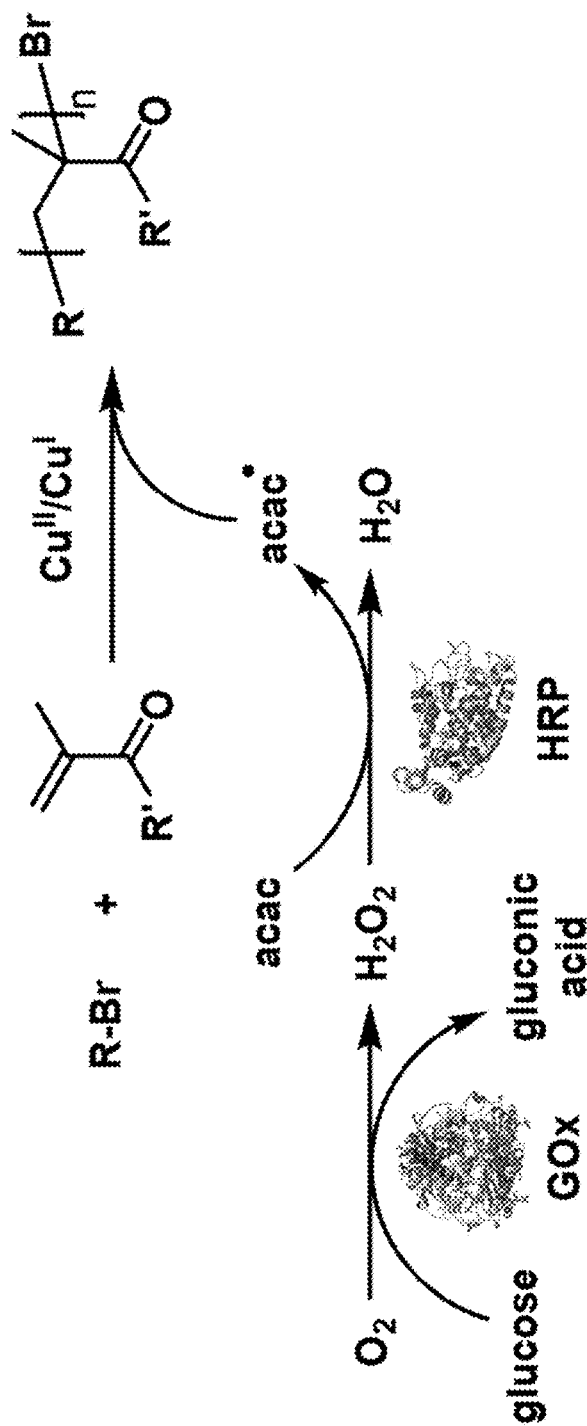
FIG. 7 is a scheme illustrating oxygen-fueled ATRP driven by the use of glucose, GOx, horseradish peroxidase (HRP), and acetylacetonate (ACAC) enzymatic cascade to continuously generate radicals for an ICAR-ATRP from the formed peroxide.
Figure 8:
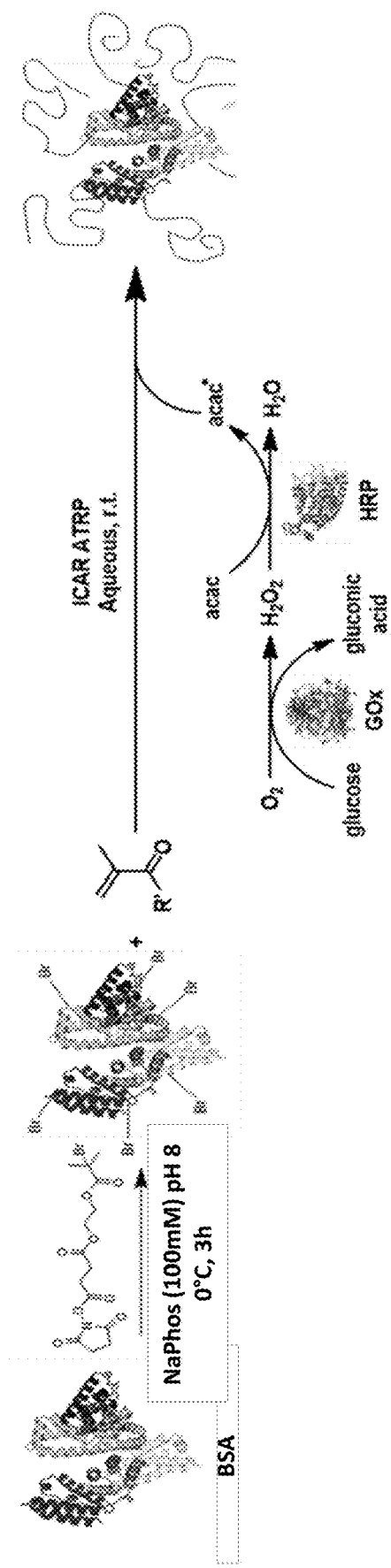
FIG. 8 is a scheme showing polymerization of bioconjugates via ATRP using enzymes.

A further extension of the use of biological agents in the oxygen tolerant ATRP process is the use of an enzymatic cascade comprising HRP and ACAC to drive bio-fueled ICAR-ATRP (FIG. 7). This can result in a true enzymatic bio-conjugate self-promoted polymerization (FIG. 8).

Figure 9:
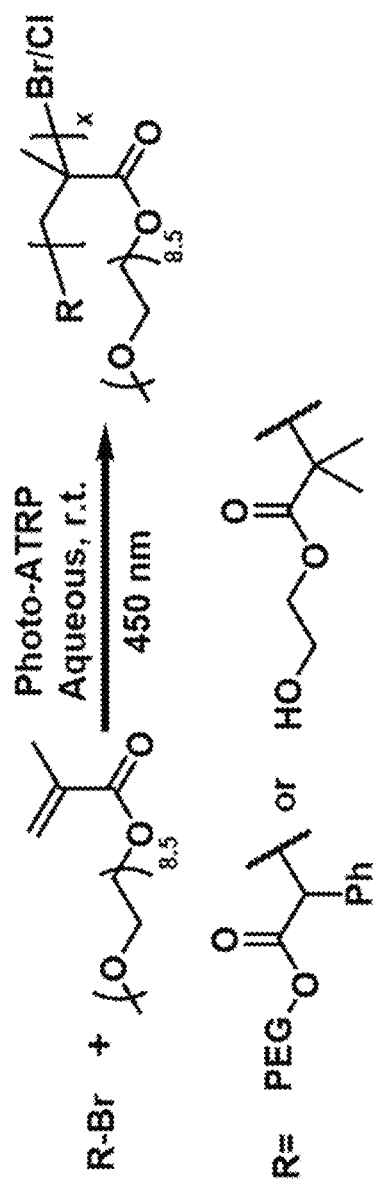
FIG. 9 is a scheme for a photo-ATRP method.

Oxygen-tolerant photo-ATRP methods also are provided herein. Previously, photo-ATRP using blue light irradiation in aqueous media was only achievable in the presence of high Cu loading, 5000-7000 ppm. However when a series of reactions were carried out in the presence of glucose, GOx, and pyruvate (GGP), the reaction attained high conversions (>90%) within 2 hours while the $M_n$ and Đ were well controlled using blue light irradiation at 450 nm. A scheme for photo-ATRP is shown in FIG. 9.

The following ratio of reagents were employed in all the reactions summarized in TABLE 12; [Glucose]=200 mM, [GOx]=2 µM, [sodium pyruvate]=100 mM. Total volume=5 mL. All reactions produced polymers with low Đ (the majority lower than 1.25) in high yield, with the majority of products formed with over 90% conversion in 2 hours at copper concentrations as low as to 100 ppm. These aspects of the disclosed methods were exemplified by conducting homogeneous aqueous ICAR-ATRP or photo-ATRP in the presence of oxygen.

In some cases, this document provides ATRP reactivating procedures. For example, surface-initiated ARGET ATRP (SIP) reactions can be carried out using functionalized solid surfaces as initiators to form functionalized particles or functionalized surfaces. GOx-assisted SIP has all the benefits of GOx-assisted solution phase polymerization, enabling the production of polymer brush coatings without degassing. GOx-assistance can makes non-degassed ARGET ATRP far more reliable by reducing variability. In some cases, a monomer such as POEGMA, PDMAEMA, or PMSEA can be grown from a solid surfaces. Oxygen-tolerant ARGET ATRP can be particularly useful for such methods because its oxygen tolerance can be tuned by varying the ratio of reducing agent (e.g., L-ascorbic acid; LAscA) to copper complex. LAscA can reduce Cu(II) species to Cu(I), which can then scavenge oxygen that inhibits polymerization. The amount of LAscA can be chosen to react with both copper and dissolved oxygen, or to reduce only a fraction of the copper.

In any of the methods provided herein, any appropriate amount of transition metal catalyst (e.g., Cu) and reducing agent can be used. In some cases, the concentration of transition metal catalyst can range from about 10 ppm to about 1200 ppm (e.g., about 10 ppm to about 20 ppm, about 20 ppm to about 50 ppm, about 50 ppm to about 100 ppm, about 100 ppm to about 200 ppm, about 200 ppm to about 300 ppm, about 300 ppm to about 500 ppm, about 500 ppm to about 750 ppm, about 750 ppm to about 1000 ppm, or about 1000 ppm to about 1200 ppm). In some cases, suitable amounts of reducing agent can range from about 0.1 µM to about 500 mM (e.g., about 0.1 µM to about 1 µM, about 1 µM to about 10 µM, about 10 µM to about 100 about 100 µM to about 1 mM, about 1 mM to about 10 mM, about 10 mM to about 100 mM, or about 100 mM to about 500 mM). In some cases, the ratio of reducing agent to transition metal catalyst can range from about 0.2:1 to about 20:1 (e.g., about 0.2;1, about 0.3:1, about 0.4:1, about 0.5:1, about 0.6:1, about 0.7:1, about 0.8:1, about 0.9:1, about 1:1, about 2:1, about 3:1, about 4:1, about 5:1, about 6:1, about 7:1, about 8:1, about 9:1, about 10:1, about 12:1, about 15:1, or about 20:1).

The ability to graft copolymers from the active biological agents utilized in the exemplary reactions discussed above can allow similar reactions to occur in less polar or even organic polymerization media simply by tuning the graft density and graft composition of the biological agents to retain agent activity while allowing solubility in the selected medium comprising the desired monomers.

In some embodiments, this document provides methods resulting from the development of the first fully-oxygen tolerant ATRP, exemplified by utilizing ICAR-ATRP and photo-ATRP, enabled by the continuous conversion of oxygen to carbon dioxide catalyzed by GOx (or another suitable oxidase) with glucose (or another suitable sugar) and a ROS scavenger such as sodium pyruvate or HRP as sequential sacrificial substrates to remove formed hydrogen peroxide, without interaction with either the catalyst or the growing polymerization radical. This procedure was created to eliminate the oxygen present in air in contact with the reaction medium, allowing for grafting of antifouling polymers from solid surfaces, but it also led to development of a new and intriguing approach which can be considered an air stimulated ATRP.

The methods disclosed herein provide open reactors of any scale. These methods can be used to add polymer chains to any appropriate solid surface (e.g., metal, plastic, or glass) or any appropriate molecule. In some cases, the methods provided herein can be used to generate polymer chains on medical device or instrument (e.g., a stent or a hospital instrument), or on a biological molecule such as a protein (e.g., an enzyme such as an esterase, a lipase, an organophosphate hydrolase, a cholinesterase, etc.). Moreover, is noted that the GOx can be added to the reaction medium or, in some cases, can be immobilized on a surface (see, e.g., Nothling et al., *Chem. Commun.* 2019, 55:8544-8547). The methods disclosed herein also can be used for preparation of functional gels and 3D printing.

As disclosed herein, naturally occurring signals driven by enzymatic cascades and triggered by an oxygen stimulus can be applied to a controlled radical polymerization exemplified by the polymerization of monomers from ATRP imitators, linked to activated amino acids, to create protein-polymer biohybrids. In similar fashion, the chain extension of a DNA strand with methacrylate monomers can be achieved upon exposure to oxygen for the initiation of an enzymatic cascade by oxygen orchestrated by a Cu/tris(2-pyridylmethyl)amine (TPMA) catalyst complex.

Figure 14B:
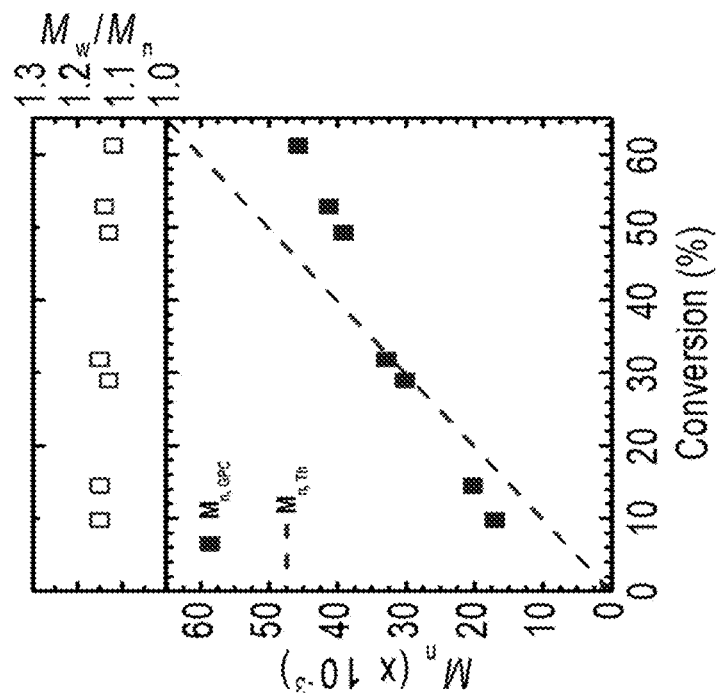
FIG. 14B is a graph plotting the evolution of molecular weight and Đ.
Figure 14A:
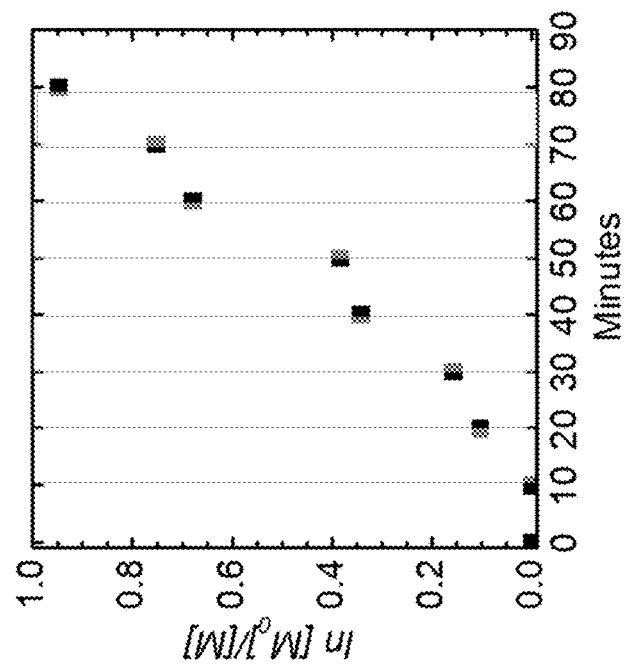
FIG. 14A is a graph plotting the kinetics of a temporally-controlled oxygen-fueled ATRP reaction.

The experimental set up consisted of mixing the varied amounts of substrate and products with GOx, HRP, and ppm amounts of Cu/TPMA catalyst. The sequence of reactions is plotted in FIGS. 14A and 14B, and consists of the catalytic conversion of β-D-glucose and oxygen to hydrogen peroxide and gluconate by GOx. The produced hydrogen peroxide and acetylacetonate (ACAC) reacted with horseradish peroxidase and generated a controlled supply of radicals into the system that reacted with monomers which produced carbon-based radicals, subsequently reducing Cu(II) into Cu (I). A reversible homolytic (pseudo)halogen transfer between a dormant species and the metal complex in the lower state ($Cu^I X/L_n$) then resulted in the formation of propagating polymer chain and a metal complex in a higher oxidation state with a coordinated halide ligand.

Figure 14C:
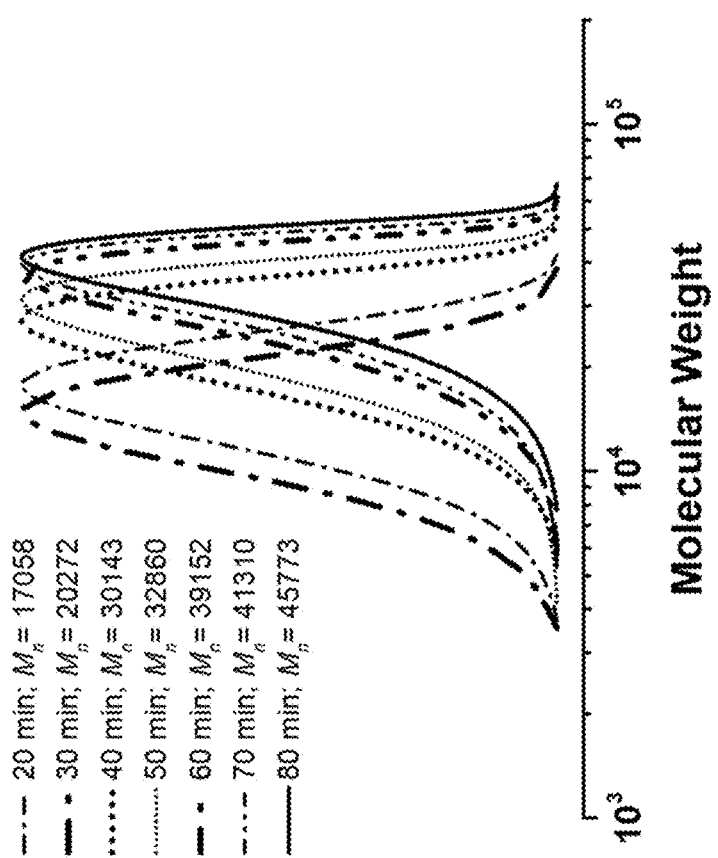
FIG. 14C is a graph showing GPC traces of samples taken periodically from the polymerization.

Due to the similarities of this procedure to ICAR-ATRP, this approach could be also termed as an enzymatic ICAR-ATRP (enz-ICAR-ATRP). The polymerization experiments reported herein were performed under physiologically relevant conditions and consisted of the use of PBS 1× pH: 6 at 37° C., with a ppm level of Cu/tris(2-pyridylmethyl)amine (TPMA) catalyst. The slight acidity of the reaction medium was selected to ensure optimum working conditions for both enzymes. OEOMA, Mn=500 ($OEOMA_{500}$), was polymerized in a completely open vial using alkyl α-bromophenylacetate as an initiator and 21 mM of β-D-glucose. $Cu^{II}Br2$/TPMA was selected as the catalyst since it would form a robust complex that would not undergo a significant disproportionation in aqueous media (Fantin et al., *Macromol.* 2017, 50(7):2696-2705). Since PBS already contained 137 mM of NaCl, the addition of extra salts containing halogens to minimize the dissociation of the anion from the deactivators was not needed (Simakova et al., supra). Well-defined polymers with high molecular weight ($M_n$>70,000) and low dispersities (Đ≤1.13) were obtained in less than one hour under these conditions (FIG. 14C).

GOx and HRP are used commonly in the food industry because of their non-toxicity for humans. The most common uses are for the removal of glucose from egg-whites before drying for use in the baking industry, removal of oxygen from the head-space above bottled and canned drinks and reducing non-enzymatic browning in wines and mayonnaises (Rocker et al., *Food Chemistry* 2016, 210:660-670; and Bonet et al., *Food Chemistry* 2006, 99(2): 408-415). Nevertheless, it was decided to pursue very low concentrations of these enzymes in order not to interfere with the properties of the synthesized polymer. The total amount of protein was decreased to nanomolar (nM) concentrations, representing less than 0.06% (<300 μg) versus the mass of monomer used (500 mg) in the synthesis. In order to understand the role that each one of the links played in this "oxygen fueled" ATRP, their concentrations were modified and the effects on the rate of ATRP, molecular weight and dispersity were measured.

Once the core parameters in this enzymatic machinery were adjusted (TABLE 14) the limits of the control provided by $Cu^{II}$/TPMA complex at lower ppm concentrations ([Cu]) versus monomer was studied. The results revealed a correlation between the amount of Cu and the $M_w/M_n$. Higher concentrations of Cu yielded better control and provided copolymers with lower dispersities, while lower concentrations showed higher Đ and a slower rate of reaction, as expected for ATRP. Nevertheless, using only 100 ppm of catalyst (Entry 12), a polymer with $M_n$=33700 and Đ=1.31 was obtained in 30 minutes. These numbers are significant, considering that the actual concentration of Cu in a 5 mL reaction mixture is only 10 ppm.

Since air was needed to activate the cascade of reactions that produced a continuous flow of radicals, which then reacted with the monomer to produce carbon-based radicals for the (re)generation of $Cu^I$ activators, it was expected that polymerization could be switched on/off under aerobic/anaerobic conditions respectively. To verify the need of aerobic environments to induce polymer growth and demonstrate that this system displayed temporal control, an experiment in a Schlenk flask where air was intermittently supplied/removed to/from the reaction mixture. The chain growth stopped after switching to an anaerobic environment. This was achieved by performing a "freeze, pump, thaw" technique, and was restarted after reestablishing an aerobic environment by injecting air to the reaction. Excellent control was achieved over the polymerization and polymers with low dispersity, and predictable molecular weights were prepared. The slow rate of polymerization in the anaerobic (off) steps was attributed to the residual hydrogen peroxide in the solution that radicals generated by HRP, until the substrate was fully consumed. Chain extension was achieved by using a purified macroinitiator based on $POEOMA_{500}$-Br with $M_n$=38,214, Đ=1.13 for the copolymerization of $OEOMA_{300}$, yielding a well-defined block copolymer using this biocatalytic approach, $M_n$=50,765, Đ=1.23.

One main advantage of the procedures disclosed herein over previously known improvements in ATRP, such as procedures that use low concentrations of active catalyst complexes in conjunction with reducing agents, is that one can now remove low concentrations of oxygen from a sealed flask. Another advantage is that the enzymatic cascade of reactions allows ATRP to be conducted in an open reactor. This would be a particular utility if one wanted to run multiple reactions in a well plate reactor, where well defined bioconjugates can be easily prepared in high throughput with simple variation in reagent compositions/concentrations in each well, to prepare evaluate materials for evaluation in a spectrum of medical applications.

The procedure also can be applied to conducting grafting from solid surfaces (e.g., flat or curved metal or plastic surfaces) in "open" continuous flow procedures. Such methods can be used for coating food or beverage containers, metals or coatings for use in ships to reduce/halt biofilm formation, or on the surfaces of instruments for hospitals, for example. In addition, the fact that photo-ATRP can be carried out in the open air means that patterned surfaces can be readily prepared.

The oxygen fueled version of the procedure could be a less expensive method by which to prepare pure polymers or bioconjugates, as low concentrations of catalyst can provide well defined products in a short period of time, thereby allowing high throughput and low catalyst cost in addition to easy purification, with almost no additional reducing agent added to the reaction medium, thereby reducing cost and simplifying the need for post-polymerization purification.

The invention will be further described in the following examples, which do not limit the scope of the invention described in the claims.

EXAMPLES

The first series of experiments were designed based on previous experience with ICAR-ATRP in aqueous systems (Konkolewicz et al., *Macromol.* 2012, 45:4461-4468), and were adjusted according to the results obtained with the addition of GOx (2.5 µM), NaBr (100 mM) and glucose (200 mM) in environments exposed to air. ICAR-ATRP was selected due to its ability to prevent the sudden oxidation of Cu (I) to Cu (II) through the slow decomposition of VA-044 at contact with air, which in addition to bestowing thermoregulation to the system, offers the capability of turn on/off the reaction once that the oxygen is removed simply by reducing the temperature of the reaction. Interestingly, the first attempts performed in completely opened vials did not yield any polymerization with agitation of the reaction medium, but in the absence of agitation, polymerization was obtained. This situation taught us the importance of the oxygen diffusion in the reaction, which has been reported elsewhere (Lv et al., supra). Subsequently, reactions in a

TABLE 1

GOx assisted ICAR-ATRP

| M/I/VA-044/Cu/Ligand | Initiator | [M]/mM | [Cu]/ppm | [NaBr]/mM | time/h | Conv./% | Th · Mn/KD | Mn, GPC | Đ |
|---|---|---|---|---|---|---|---|---|---|
| 200/1/0.3/0.06/0.3 | BPAA | 216 | 300 | 100 | 3 | 95 | 95 | 96.8 | 1.27 |
| 400/1/0.3/0.12/0.6 | BPAA | 216 | 300 | 100 | 2 | 90 | 180 | 110 | 1.23 |
| 600/1/0.3/0.18/0.9 | BPAA | 216 | 300 | 100 | 2 | 50 | 152 | 73.3 | 1.33 |
| 800/1/0.3/0.24/1.2 | BPAA | 216 | 300 | 100 | 2 | 76 | 304 | 67.7 | 1.24 |
| 100/1/0.3/0.03/0.15 | BPAA | 216 | 300 | 100 | 2 | 51 | 25.5 | 23.5 | 1.25 |

TABLE 2

ICAR-ATRP of $OEOMA_{500}$ in the presence of GOx, sodium pyruvate, and oxygen.

| No. | M/I/VA-044/Cu/Ligand | [Cu] (ppm) | time (h) | Conv. (%) | Mn, Th* | $Mn_{GPC}$ | $Mn_{GPC}$ Corrected* | Đ |
|---|---|---|---|---|---|---|---|---|
| AE87 | 200/1/0.3/0.1/0.5 | 500 | 1.5 | 96.2 | 96.2 | 91.3 | 142.9 | 1.09 |
| AE88 | 400/1/0.3/0.2/1 | 500 | 1.5 | 98.1 | 196.3 | 144.8 | 233.9 | 1.12 |
| AE89 | 600/1/0.3/0.3/1.5 | 500 | 1.5 | 97.2 | 291.5 | 200.3 | 330.8 | 1.13 |
| AE90 | 800/1/0.3/0.4/2 | 500 | 1.5 | 96.98 | 387.9 | 233.9 | 390.5 | 1.18 |

*Mn expressed in $10^{-3}$; M = $OEOMA_{500}$, [M] = 10 vol % in PBS, [Br–] = 100 mM, [Glucose] = 200 mM, [Sodium Pyruvate] = 100 mM, [GOx] = 2.5 µM, RXN temperature = 45° C.; DP 200 [I] = 1 mM, DP 400 ][I] = 0.5 mM, DP 600 [I]= 0.33 mM, DP 800 [I] = 0.25 mM;
*Corrected Đ, Correction was executed using Mark-Houwink Equation based on PMMA-Toluene as universal calibration.

TABLE 3

Conditions for grafting from BSA polymerization

| No. | M/I/VA-044/Cu/Ligand | Initiator | [M] (mM) | [Cu] (ppm) | [NaBr] (mM) | time (h) | Conv. (%) | Th · Mn (KD) | $Mn_{GPC}$ Corrected* | Đ |
|---|---|---|---|---|---|---|---|---|---|---|
| 103 | 200/1/0.3/0.2/1 | BiBB | 216 | 1000 | 100 | 1.5 | 92.3 | 92.5 | 81.3 | 1.22 |

*M = $OEOMA_{500}$, [M] = 10 vol % in PBS, [Br–] = 100 mM, [Glucose] = 200 mM, [Sodium Pyruvate] = 100 mM, [GOx] = 2.5 µM, RXN temperature = 45° C;
Correction was executed using Mark-Houwink Equation based on PMMA-Toluene as universal calibration.

capped vial were executed yielding reproducible polymerizations even with a strong stirring.

The early polymerizations were conducted with a molar ratio of [OEOMA$_{500}$]/[Initiator]/[VA-044]/[Cu]/[TPMA]=200:1:0.3:0.2:0.4 and a volume ratio of monomer/PBS=1:9 at 45° C. The starting polymerization initiator was HO-EBiB, which generated homogeneous chains with relatively low dispersities, Đ~1.3. However, the molecular weights obtained were far lower than the theoretical values, approximately 4× lower, which made us aware of the possibility that new chains being generated by H$_2$O$_2$. For that reason, it was envisioned that a more reactive initiator (Tang and Matyjaszewski, *Macromol.* 2007, 40:1858-1863) such as α-bromophenyl acetic acid (BPAA), which has an approximately 500× faster K$_{ATRP}$ than HO-EBiB in MeCN, could suppress such side reactions. In fact, while the polymerizations using BPAA showed a better correlation with the theoretical value the dispersity was not significantly improved.

Therefore, a second screening exploring different ratios of reactants was conducted to optimize the polymerization conditions. Experiments with different loadings of catalyst (100, 300, 500 and 1000 ppm) revealed that the amount of Cu can be lowered down to 300 ppm with similar degrees of control; while lower concentrations resulted in broadened dispersity. Varying the ratios of Initiator/VA-044 (1:0.3, 0.1, 0.05, 0.02, 0.01) resulted in the observation that the reaction becomes sluggish and loses control with ratios lower than 1/0.05. Since the reactions were performed in PBS 1×, which contains 137 mM Cl$^-$ adding extra NaBr salt was not strictly required as reported in other aqueous systems (Konkolewicz et al., supra), although the addition of concentrations >100 mM slowed down the reaction.

During the third stage of the project when higher molecular weights and DPs (>200) were pursued, a new challenge was faced; the obtained experimental M$_n$ was again at an increasing distance from the Th. M$_n$, and the polymer chains that were expected to reach 300kD were as low as 68kD, almost 5× times lower than the planned molecular weight. This situation showed the limits of tolerance for our initial conditions to the degassing of ambient air by reaction with GOx as the reaction resulted in the continuous generation of H$_2$O$_2$, even using a closed vial.

Consequently, this required a search for optimum conditions that could get rid of H$_2$O$_2$ and at the same time generate clean side products that did not interfere with an ATRP.

Those requirements made us turn our attention to nature's solutions for intake of oxygen and prompted us to design a previously unreported cascade of reactions that, in a deferential manner, emulate the cycle of transformations of oxygen into CO$_2$ in living bodies, Scheme 4. The inclusion of sodium pyruvate, as an exemplary peroxide scavenger, to the system was also based recent mechanistic reports that have demonstrated its fast reactivity towards hydrogen peroxide in biological systems (Asmus et al., supra).

Thus, the designed cascade system, emulating the aerobic respiration cycle, did not just decrease the Đ and make the measured M$_n$ of the of the polymer chains match the Th. M$_n$., but also allowed high tolerance of oxygen that provided controlled ATRP polymerizations of non-deoxygenated reagents, indeed, even in vessels truly open to air.

Experiments using the improved bio-deoxygenation conditions with different amounts of Cu catalyst (300, 500 and 1000 ppm) at different DPs (200, 400, 600 and 800) showed narrower dispersities (1.09≥Đ≤1.2) and reached quantitative conversions in a maximum of 2 hours.

This oxygen resistant enzymatic ICAR-ATRP system also exhibited different degrees of control over the polymerization depending on the concentration of added catalyst. Higher amounts of catalyst provided better correlation of the Th. M$_n$. for low targeted DPs; however when high DPs were targeted lower amounts of catalyst gave a better correlation of Th. M$_n$ with measured M$_n$.

Example 1—Determining Conditions for Oxygen Tolerant ATRP

1A) GOx plus Glucose Assisted ICAR-ATRP (FIG. 3)

| Exp * | LF-2-68 |
|---|---|
| M:I:VA-044:Cu(II):TPMA | 200; 1:0.3:0.2:0.4 |
| Monomer | OEOMA$_{500}$ |
| Time (h) | 4 |
| Conv. (%) | 88 |
| Mn (kDa) | 19 |
| Đ | 1.27 |

I = HO-EBiB, [M] = 20% (v/v), [NaBr] = 100 mM, [GOx] = 2.5 µM, [Glucose] = 200 mM, solvent = 1X PBS, pH = 7.4

An ATRP reaction was conducted with 1000 ppm of Cu with target DP$_n$=200. After 4 hours the conversion reached 88%, but M$_{n,\,exp}$ was much lower than M$_{n,\,Th}$ even though the dispersity was acceptable. FIG. 10A shows the kinetics of the polymerization and FIG. 10B shows the relationship between the actual MW and theoretical MW while 1C shows the GPC curves, all displaying narrow Đ.

1B) Effect of Catalyst Loading

The second parameter examined was the Cu loading, which was varied from 1000 ppm to down to 100 ppm. As shown in TABLE 4, the polymerization maintained good control down to catalyst concentrations of 300 ppm. When using 100 ppm Cu, the reaction became much slower while the GPC peaks of kinetic samples did not show a significant increase in M$_n$ with conversion and dispersity became higher.

TABLE 4

Effect of different concentrations of catalyst

| No. | M/I/VA-044/Cu/Ligand | [Cu]/ppm | time/h | Conv./% | M$_{n,Th}$ | M$_{n,\,GPC}$ | Đ |
|---|---|---|---|---|---|---|---|
| 3-5a | 200/1/0.3/0.06/0.3 | 300 | 3 | 95 | 95 | 96.8 | 1.27 |
| 3-10 | 200/1/0.3/0.2/1 | 1000 | 1 | 91 | 91 | 97 | 1.18 |
| 3-11 | 200/1/0.3/0.02/0.1 | 100 | 4 | 34 | 34 | 59.6 | 1.52 |
| 3-12 | 200/1/0.3/0.1/0.5 | 500 | 1.5 | 71 | 71 | 66.5 | 1.23 |

M = OEOMA500, [M] = 10 vol %, I = BPAA, [Br$^-$] = 100 mM, [Glucose] = 200 mM, [GOx] = 2.5 µM, RXN temperature = 45° C.

Figure 11:
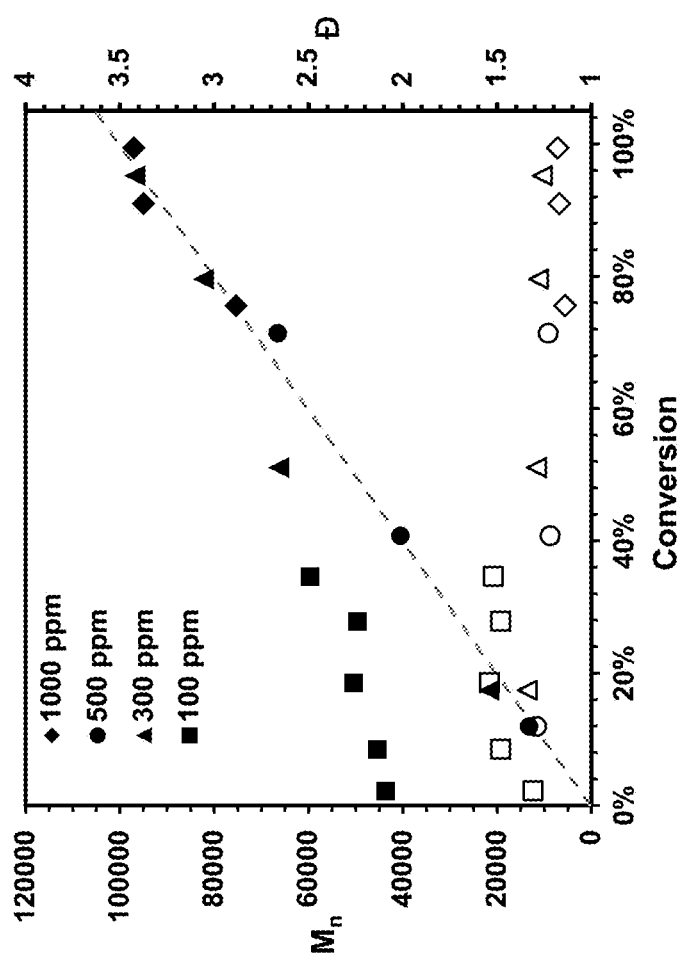
FIG. 11 is a graph plotting the effect of conducting the polymerization reaction with various concentration of copper.

The results are summarized in FIG. 11, which shows the effect of different concentrations of catalyst on the rate of increase in M$_n$ with conversion and dispersity.

1C) Effect of Targeted DP

The target $DP_n$, was varied from DP=800 down to DP=100 with monomer concentrations and Cu loading unchanged, i.e., initiator usage was altered to achieve such changes, as well as corresponding VA-044 usage. It was observed that MW control was not maintained for higher than DP=200. Higher target DP resulted in formation of polymers with $M_n$, GPC much lower than the theoretical value (TABLE 5). However, dispersities of all trials remained reasonably low for all runs with [Cu]=300 ppm or below.

TABLE 5

Effect of targeting different degrees of polymerization

| Run | M/I/VA-044/Cu/Ligand | Target DPn | time/h | Conv./% | $M_{n,Th}$ | $M_{n, GPC}$ | Đ |
|---|---|---|---|---|---|---|---|
| 3-5a | 200/1/0.3/0.06/0.3 | 200 | 3 | 95 | 95 | 96.8 | 1.27 |
| 3-6 | 400/1/0.3/0.12/0.6 | 400 | 2 | 90 | 180 | 110 | 1.23 |
| 3-7 | 600/1/0.3/0.18/0.9 | 600 | 2 | 50 | 152 | 73.3 | 1.33 |
| 3-8 | 800/1/0.3/0.24/1.2 | 800 | 2 | 76 | 304 | 67.7 | 1.24 |
| 3-9 | 100/1/0.3/0.03/0.15 | 100 | 2 | 51 | 25.5 | 23.5 | 1.25 |

M = $OEOMA_{500}$, [M] = 10 vol %, I = BPAA, [Br⁻] = 100 mM, [Glucose] = 200 mM, [GOx] = 2.5 µM, RXN temperature = 45° C.

1D) Effect of Changing Initiator to VA-044 Ratio

The next parameter examined was the Initiator: VA-044 ratio. The ratio was varied from 1:0.3 to 1:0.01. The results, presented in TABLE 6, show that the reaction proceeded in a controlled manner from 30% VA-044 to 5%, with the MW matching the theoretical value and narrow dispersity. While decreasing VA-044 portion to lower than 2%, the rate of polymerization became slower and dispersity increased.

TABLE 6

Effect of changing I:VA-044 ratio

| Run | M/I/VA-044/Cu/Ligand | I:VA-044 | time (h) | Conv. (%) | $M_{n,Th}$ | $M_{n, GPC}$ | Đ |
|---|---|---|---|---|---|---|---|
| 3-5a | 200/1/0.3/0.06/0.3 | 1:0.3 | 3 | 95 | 95.0 | 96.8 | 1.27 |
| 3-5 | 200/1/0.1/0.06/0.3 | 1:0.1 | 3 | 93 | 93.0 | 105.3 | 1.28 |
| 3-20 | 200/1/0.05/0.06/0.3 | 1:0.05 | 3 | 91 | 91.2 | 68.3 | 1.27 |
| 3-21 | 200/1/0.02/0.06/0.3 | 1:0.02 | 3 | 58 | 58.4 | 38.9 | 1.37 |
| 3-22 | 200/1/0.01/0.06/0.3 | 1:0.01 | 3 | 48 | 48.9 | 31.8 | 1.48 |

M = $OEOMA_{500}$, [M] = 10 vol %, I = BPAA, [Br⁻] = 100 mM, [Glucose] = 200 mM, [GOx] = 2.5 µM, RXN temperature = 45°

1E) Effect of Concentration of Added Salt

The last parameter modified was the concentration of the NaBr additive. Since the reaction was always carried out in 1×PBS, the solution contained 137 mM NaCl in all cases. As shown in TABLE 7, even in the case where no NaBr was added, the reaction still proceeded quickly and was well controlled. When increasing amounts of NaBr were added, the reaction rate dropped and the dispersity increased to 1.29.

TABLE 7

Effect of added salt

| Run | M/I/VA-044/Cu/Ligand | [NaBr] | time (h) | Conv. (%) | $M_{n,Th}$ | $M_{n, GPC}$ | Đ |
|---|---|---|---|---|---|---|---|
| 3-23 | 200/1/0.3/0.06/0.3 | 0 mM | 3 | 99 | 99.5 | 109.7 | 1.19 |
| 3-29 | 200/1/0.3/0.06/0.3 | 30 mM | 3 | 98 | 98.5 | 107.9 | 1.24 |

TABLE 7-continued

Effect of added salt

| Run | M/I/VA-044/Cu/Ligand | [NaBr] | time (h) | Conv. (%) | $M_{n,Th}$ | $M_{n, GPC}$ | Đ |
|---|---|---|---|---|---|---|---|
| 3-5a | 200/1/0.3/0.06/0.3 | 100 mM | 2 | 95 | 95.3 | 96.8 | 1.27 |
| 3-30 | 200/1/0.3/0.06/0.3 | 200 mM | 2 | 55 | 55.2 | 41.9 | 1.29 |

M = $OEOMA_{500}$, [M] = 10 vol %, I = BPAA, [Glucose] = 200 mM, [GOx] = 20 µM, RXN temperature = 45° C.

Example 2—GOx Plus Glucose Assisted ICAR-ATRP

2A) In the Absence of a Peroxide Scavenger

TABLE 8 shows the initial results of experiments conducted without the addition of a peroxide scavenger. The results show dispersities (Ds) that were broader than expected from a well-controlled polymerization, and also demonstrated that when high degrees of polymerization were targeted, the reactions did not reach the targeted molecular weights.

2B) Polymerizations Conducted in the Presence of a Peroxide Scavenger

When a peroxide scavenger (pyruvate) was included, the resulting Ds were narrow and the measured (corrected) $M_n$ was closer to theoretical values (TABLE 9).

2C) Reactions Conducted Using 500 ppm Copper Targeting Different DPs

Figure 13:
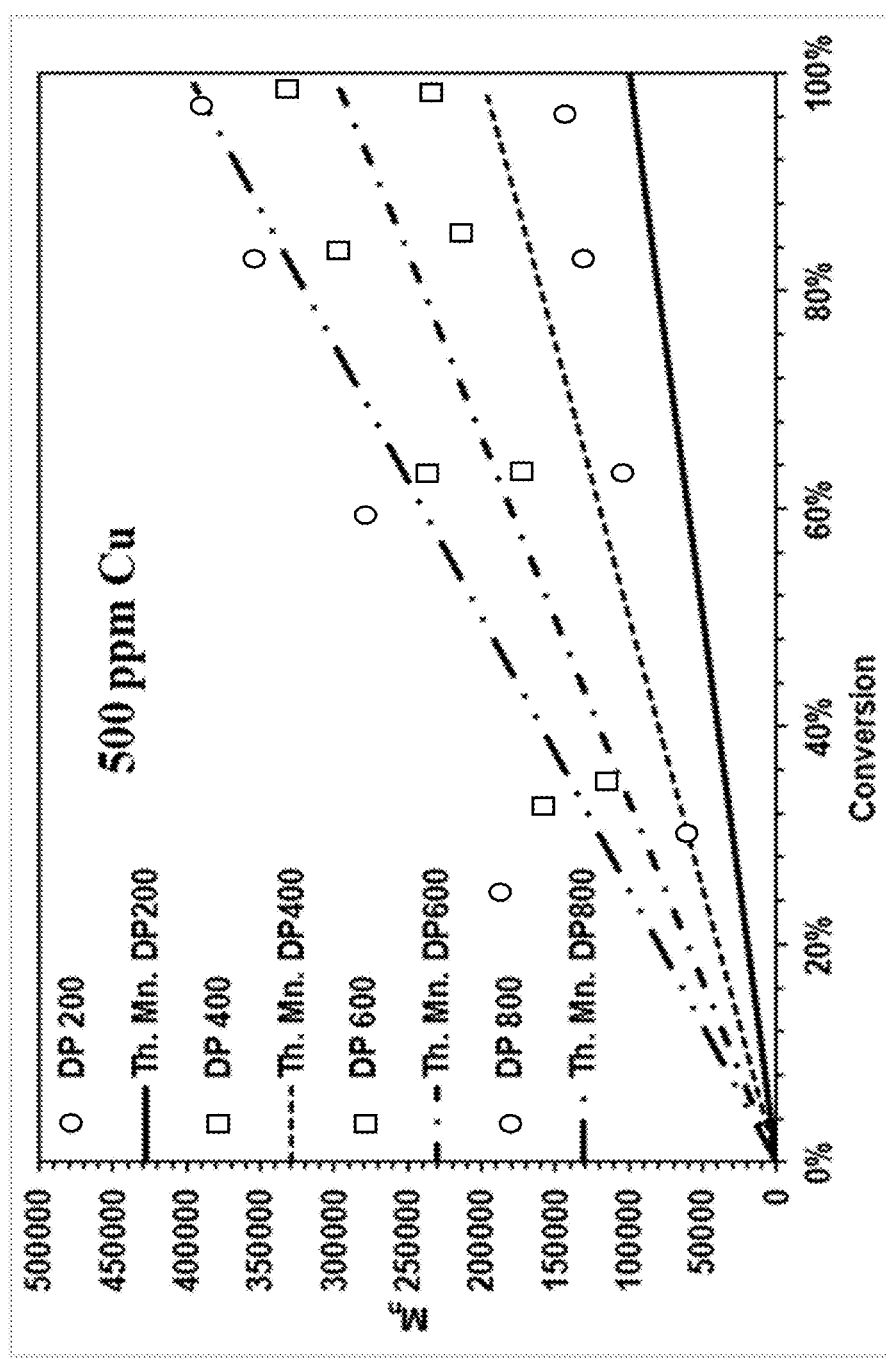
FIG. 13 is a graph plotting the evolution of measured molecular weight with conversion for a series of runs with 500 ppm copper targeting different degrees of polymerization (DPs) and a comparison with the theoretical molecular weights as molecular weight evolves.

When 500 ppm Cu was included, the polymers resulting from all reactions had narrow molecular weights that were close to theoretical for all targeted DP (TABLE 10). FIG. 13 shows the relationship between targeted DP and rate of polymerization, with lines indicating the evolution of the targeted DPs with conversion.

Example 3—Oxygen Fueled ICAR-ATRP

The schematic for this reaction is shown in FIG. 7 and the results of a series of experiments examining the role of different concentrations of horseradish peroxidase and different targeted DPs are shown in TABLE 11.

This series of ICAR-ATRP reactions conducted without the addition of a standard free radical initiator resulted in the formation of polymers with molecular weights close to theoretic numbers and low Đ indicating well controlled reactions were carried out.

TABLE 8

GOx + Glucose assisted ICAR-ATRP "non-improved conditions"

| M/I/VA-044/Cu/Ligand | Initiator | [M] (mM) | [Cu] (ppm) | [NaBr] (mM) | time (h) | Conv. (%) | Th · Mn (KD) | $M_{n, GPC}$ | Đ |
|---|---|---|---|---|---|---|---|---|---|
| 200/1/0.3/0.06/0.3 | BPAA | 216 | 300 | 100 | 3 | 95 | 95 | 96.8 | 1.27 |
| 400/1/0.3/0.12/0.6 | BPAA | 216 | 300 | 100 | 2 | 90 | 180 | 110 | 1.23 |
| 600/1/0.3/0.18/0.9 | BPAA | 216 | 300 | 100 | 2 | 50 | 152 | 73.3 | 1.33 |
| 800/1/0.3/0.24/1.2 | BPAA | 216 | 300 | 100 | 2 | 76 | 304 | 67.7 | 1.24 |
| 100/1/0.3/0.03/0.15 | BPAA | 216 | 300 | 100 | 2 | 51 | 25.5 | 23.5 | 1.25 |

TABLE 9

GOx + Glucose + Pyruvate assisted ICAR-ATRP

| No. | M/I/VA-044/Cu/Ligand | [M] (mM) | [Cu] (ppm) | [NaBr] (mM) | time (h) | Conv. (%) | Th · Mn* | Mn $_{GPC}$, before correction* | Mn, $_{GPC}$ corrected* | Đ |
|---|---|---|---|---|---|---|---|---|---|---|
| 82 | 100/1/0.3/0.03/0.15 | 216 | 300 | 100 | 1.5 | 91.6 | 45.8 | 82.8 | 128.7 | 1.15 |
| 81 | 200/1/0.3/0.06/0.3 | 216 | 300 | 100 | 2 | 95.4 | 95.4 | 110.9 | 175.9 | 1.17 |
| 78 | 400/1/0.3/0.12/0.6 | 216 | 300 | 100 | 1.5 | 97 | 194 | 148.1 | 239.6 | 1.17 |
| 79 | 600/1/0.3/0.18/0.9 | 216 | 300 | 100 | 1.5 | 94.4 | 283.3 | 203.5 | 336.5 | 1.18 |
| 80 | 800/1/0.3/0.24/1.2 | 216 | 300 | 100 | 1.5 | 96 | 384 | 263.2 | 442.9 | 1.27 |
| 83 | 200/1/0.3/0.2/1 | 216 | 1000 | 100 | 1 | 92.8 | 92.8 | 74.4 | 114.8 | 1.13 |
| 84 | 400/1/0.3/0.4/2 | 216 | 1000 | 100 | 1 | 94.23 | 188.5 | 106.7 | 168.8 | 1.17 |
| 85 | 600/1/0.3/0.6/3 | 216 | 1000 | 100 | 1 | 95.12 | 285.4 | 125.3 | 200.4 | 1.18 |
| 86 | 800/1/0.3/0.8/4 | 216 | 1000 | 100 | 1 | 95.1 | 380.3 | 147 | 237.7 | 1.2 |
| 76 | 200/1/0.3/0.1/0.5 | 216 | 500 | 100 | 1 NK | 92.5 | 92.5 | 109.2 | 173 | 1.12 |
| 77 | 500/1/0.3/0.1/0.5 | 216 | 200 | 100 | 2 NK | 99 | 247.5 | 237.5 | 396.9 | 1.17 |

*Mn expressed in $10^{-3}$; M = OEOMA$_{500}$, [M] = 10 vol %, I = BPAA, [Br−] = 100 mM, [Glucose] = 200 mM, [Sodium Pyruvate] = 100 mM, [GOx] = 2.5 μM, RXN temperature =

TABLE 10

Effect of targeting different DPs.

| Run | M/I/VA-044/Cu/Ligand | [Cu] (ppm) | time (h) | Conv. (%) | Mn, Th* | Mn$_{GPC}$* | Mn$_{GPC}$ corrected* | Đ |
|---|---|---|---|---|---|---|---|---|
| AE87 | 200/1/0.3/0.1/0.5 | 500 | 1.5 | 96.2 | 96.2 | 91.3 | 142.9 | 1.09 |
| AE88 | 400/1/0.3/0.2/1 | 500 | 1.5 | 98.1 | 196.3 | 144.8 | 233.9 | 1.12 |
| AE89 | 600/1/0.3/0.3/1.5 | 500 | 1.5 | 97.2 | 291.5 | 200.3 | 330.8 | 1.13 |
| AE90 | 800/1/0.3/0.4/2 | 500 | 1.5 | 96.98 | 387.9 | 233.9 | 390.5 | 1.18 |

*Mn expressed in $10^{-3}$; M = OEOMA$_{500}$, [M] = 10 vol % in PBS, [Br−] = 100 mM, [Glucose] = 200 mM, [Sodium Pyruvate] = 100 mM, [GOx] = 2.5 μM, RXN temperature = 45° C.;
DP 200 [I] = 1 mM, DP 400 [I] = 0.5 mM, DP 600 [I] = 0.33 mM, DP 800 [I] = 0.25 mM;
Correction was executed using Mark-Houwink Equation based on PMMA-Toluene as universal calibration.

TABLE 11

ICAR-ATRP controlled by hydrogen peroxide formed during GOx oxygen removal reaction

| No. | M/I/RI/Cu/TPMA | [M] (mM) | HRP (nM) | Radical Initiator | time (h) | Conv. (%) | Th · Mn* | $M_{n, GPC}$ Corrected* | Đ |
|---|---|---|---|---|---|---|---|---|---|
| 105 | 200/1/4/0.2/1 | 210 | 567 | HVA | 24 | — | — | — | — |
| 115 | 200/1/16/0.2/1 | 210 | 567 | ACAC | 0.5 | 79.1 | 79.3 | 58.5 | 1.13 |
| 104 | 200/1/4/0.2/1 | 210 | 567 | ACAC | 0.5 | 86.5 | 86.7 | 63.2 | 1.15 |
| 107 | 200/1/1/0.2/1 | 210 | 567 | ACAC | 0.5 | 55.6 | 55.6 | 62.5 | 1.27 |
| 111 | 200/1/0.25/0.2/1 | 210 | 567 | ACAC | 1 | 41 | 41 | 35.3 | 1.26 |
| 108 | 200/1/4/0.2/1 | 210 | 270 | ACAC | 1 | 54 | 54 | 75.3 | 1.21 |
| 112 | 200/1/4/0.2/1 | 210 | 1134 | ACAC | 0.5 | 94 | 94 | 70.9 | 1.17 |
| 116 | 200/1/4/0.2/1 | 210 | 105 | ACAC | — | — | — | — | — |
| 106 | 800/1/4/0.8/4 | 210 | 142 | ACAC | 24 | — | — | — | — |
| 110$^\alpha$ | 800/1/4/0.8/4 | 210 | 567 | ACAC | 0.25 | 11.1 | 44 | 41.1 | 1.32 |
| 114 | 800/1/16/0.8/4 | 210 | 567 | ACAC | 0.75 | 86.5 | 346 | 85.4 | 1.16 |

TABLE 11-continued

ICAR-ATRP controlled by hydrogen peroxide formed during GOx oxygen removal reaction

| No. | M/I/RI/Cu/TPMA | [M] (mM) | HRP (nM) | Radical Initiator | time (h) | Conv. (%) | Th · Mn* | $M_{n,\ GPC}$ Corrected* | Đ |
|---|---|---|---|---|---|---|---|---|---|
| 117 | 800/1/16/0.8/4 | 210 | 2268 | ACAC | NK | 99 | 396 | 107 | 1.2 |
| 118* | 800/1/64/0.8/4 | 210 | 2268 | ACAC | NK | 99 | 396 | 105 | 1.22 |

*Mn expressed in $10^{-3}$; M = OEOMA$_{500}$, [M] = 10 vol %, in PBS, [Glucose] = 21 mM, [GOx] = 210 nM, RXN temperature = 35° C.;
DP 200 [I] = 1 mM, DP 800 [I] = 0.25 mM;
*[GOx] = 840 nM & [Glucose] = 95 mM;
°[Glucose] = 5 mM & [ACAC] = 1 mM;
NK = No kinetics;
Correction was executed using Mark-Houwink Equation based on PMMA-Toluene as universal calibration.

Example 4—Oxygen Tolerant Aqueous Photo-ATRP Under Blue Light

A series of aqueous photo-ATRP reactions were conducted under blue light (450 nm) radiation with and initial ratio of reagents, [Glucose]=200 mM, [GOx]=2 µM, [sodium pyruvate]=100 mM; total volume=5 mL, TABLE 12 provides a list of reaction conditions and their results. It can be observed that the polymerizations were well controlled and reached high conversions in less than 2 hours. The "discrepancy" between the theoretical MW and measured MW can be attributed to the difference between the GPC standard and the higher molecular weight biocompatible monomer (PEG$_{2k}$BPA) employed for the polymerization which additionally formed a brush like molecule known to result in a lower measured MW than the actual MW.

TABLE 12

| Entry | M/I/Cu/TPMA | Degas | Initiator | Solvent | Time/h | Conv./% | $M_{n,Th}$ | $M_{n,\ GPC}$ | Đ |
|---|---|---|---|---|---|---|---|---|---|
| LF-3-81 | 200/1/0.2/1 | N$_2$ purge | PEG$_{2k}$BPA | H$_2$O + Br | 3.5 | 0 | — | — | — |
| LF-3-82 | 200/1/0.2/1 | Glu + GOx + Pyr | PEG$_{2k}$BPA | H$_2$O + Br | 2 | 97 | 98.9 | 58.8 | 1.29 |
| LF-3-83 | 200/1/0.2/0.24 | Glu + GOx + Pyr | PEG$_{2k}$BPA | H$_2$O + Br | 2 | 96 | 97.4 | 61.1 | 1.22 |
| LF-3-87 | 200/1/0.2/1 | Glu + GOx + Pyr | PEG$_{2k}$BPA | 1X PBS | 2 | 96 | 97.3 | 67.3 | 1.09 |
| LF-3-88 | 200/1/0.2/1 | Glu + GOx + Pyr | PEG$_{2k}$BPA | H$_2$O + Br | 2 | 96 | 96.5 | 46.4 | 1.16 |
| LF-3-89 | 400/1/0.4/2 | Glu + GOx + Pyr | PEG$_{2k}$BPA | 1X PBS | 2 | 82 | 164.7 | 130.2 | 1.09 |
| LF-3-90 | 100/1/0.1/0.5 | Glu + GOx + Pyr | PEG$_{2k}$BPA | 1X PBS | 2 | 55 | 29.7 | 32.2 | 1.11 |
| LF-3-91 | 200/1/0.2/1 | Glu + GOx + Pyr | BSA-[iBBr]$_{30}$ | 1X PBS | 1.5 | 66 | 66.0 | 67.2 | 1.09 |

Choice of solvent and initiator

| Entry | M/I/Cu/TPMA | Degas | Initiator | Solvent | Time/h | Conv./% | $M_{n,Th}$ | $M_{n,\ GPC}$ | Đ |
|---|---|---|---|---|---|---|---|---|---|
| LE-3-82 | 200/1/0.2/1 | Glu + GOx + Pyr | PEG$_{2k}$BPA | H$_2$O + Br | 2 | 97 | 98.9 | 58.8 | 1.29 |
| LE-3-87 | 200/1/0.2/1 | Glu + GOx + Pyr | PEG$_{2k}$BPA | 1X PBS | 2 | 96 | 97.3 | 67.3 | 1.09 |
| LE-3-88 | 200/1/0.2/1 | Glu + GOx + Pyr | HO-EBiB | H$_2$O + Br | 2 | 96 | 96.5 | 46.4 | 1.16 |

Effect of various Cu ppm

| Entry | M/I/Cu/TPMA | Degas | Cu ppm | Solvent | Time/h | Conv./% | $M_{n,Th}$ | $M_{n,\ GPC}$ | Đ |
|---|---|---|---|---|---|---|---|---|---|
| LF-3-89 | 400/1/0.4/2 | Glu + GOx + Pyr | 1000 | 1X PBS | 2 | 82 | 164.7 | 130.2 | 1.09 |
| LE-3-93 | 400/1/0.2/1 | Glu + GOx + Pyr | 500 | 1X PBS | 2 | 96 | 194.2 | 116.0 | 1.09 |
| LE-3-94 | 400/1/0.04/0.2 | Glu + GOx + Pyr | 100 | 1X PBS | 2 | 86 | 173.5 | 112.1 | 1.16 |
| LE-3-95 | 400/1/0.008/0.04 | Glu + GOx + Pyr | 50 | 1X PBS | 2 | 70 | 142.2 | 120.4 | 1.39 |
| LF-3-96 | 400/1/0.04/0.2 | Glu + GOx + Pyr | 100 | 1X PBS | 2 | 79 | 159.9 | 111.3 | 1.09 |

Effect of various target $DP_n$

| Entry | M/I/Cu/TPMA | Degas | Initiator | Solvent | Time/h | Conv./% | $M_{n,Th}$ | $M_{n,\ GPC}$ | Đ |
|---|---|---|---|---|---|---|---|---|---|
| LF-3-87 | 200/1/0.2/1 | Glu + GOx + Pyr | PEG$_{2k}$BPA | 1X PBS | 2 | 96 | 97.3 | 67.3 | 1.09 |
| LF-3-89 | 400/1/0.4/2 | Glu + GOx + Pyr | PEG$_{2k}$BPA | 1X PBS | 2 | 82 | 164.7 | 130.2 | 1.09 |
| LP-3-90 | 100/1/0.1/0.5 | Glu + GOx + Pyr | PEG$_{2k}$BPA | 1X PBS | 2 | 55 | 29.7 | 32.2 | 1.11 |
| LF-3-102 | 100/1/0.1/0.5 | Glu + GOx + Pyr | PEG$_{2k}$BPA | 1X PBS | 2 | 89 | 46.7 | 47.2 | 1.19 |

Effect of lowering [GOx] by half

| Entry | M/I/Cu/TPMA | Degas | [GOx] | Cu ppm | Time/h | Conv./% | $M_{n,Th}$ | $M_{n,\ GPC}$ | Đ |
|---|---|---|---|---|---|---|---|---|---|
| LF-3-94 | 400/1/0.04/0,2 | Glu + GOx + Pyr | 2 µM | 100 | 2 | 86 | 173.5 | 112.1 | 1.16 |
| LF-3-98 | 400/1/0.04/0,2 | Glu + GOx + Pyr | 1 µM | 100 | 4.5 | 83 | 168.2 | 92.9 | 1.30 |
| LF-3-87 | 200/1/0.2/1 | Glu + GOx + Pyr | 2 µM | 1000 | 2 | 96 | 97.3 | 67.3 | 1.09 |
| LF-3-99 | 200/1/0.2/1 | Glu + GOx + Pyr | 1 µM | 1000 | 4.5 | 92 | 92.2 | 59.4 | 1.21 |

TABLE 12-continued

Effect of changing [Na pyruvate]

| Entry | M/I/Cu/TPMA | Na pyruvate | Cu ppm | Time/h | Conv./% | $M_{n,Th}$ | $M_{n,\ GPC}$ | Đ |
|---|---|---|---|---|---|---|---|---|
| LF-3-87 | 200/1/0.2/1 | 100 mM | 1000 | 2 | 96 | 97.3 | 67.3 | 1.09 |
| LF-3-100 | 200/1/0.2/1 | 50 mM | 1000 | 2 | 96 | 97.6 | 69.7 | 1.18 |
| LF-3-101 | 200/1/0.2/1 | 200 mM | 1000 | 2 | 96 | 98.8 | 70.4 | 1.19 |
| LF-3-104 | 200/1/0.2/1 | 25 mM | 1000 | 2 | 85 | 85.7 | 59.4 | 1.25 |

Control exp with/without light; and no GOx/pyruvate

| Entry | M/I/Cu/TPMA | Degas | Irradiation | Time/h | Conv./% | $M_{n,Th}$ | $M_{n,\ GPC}$ | Đ |
|---|---|---|---|---|---|---|---|---|
| LF-3-82 | 200/1/0.2/1 | Glu + GOx + Pyr | Y | 2 | 97 | 98.9 | 58.8 | 1.29 |
| LF-3-82C | 200/1/0.2/1 | Glu + GOx + Pyr | N | 15 | 71 | 73.2 | 38.9 | 1.32 |
| LF-3-86 | 200/1/0.2/1 | +Glu, No degas | Y | — | — | — | — | — |

Grafting from protein

| Entry | M/I/Cu/TPMA | Degas | Initiator | Solvent | Time/h | Conv./% | $M_{n,Th}$ | $M_{n,\ GPC}$ | Đ |
|---|---|---|---|---|---|---|---|---|---|
| LF-3-91 | 200/1/0.2/1 | Glu + GOx + Pyr | BSA-[iBBr]$_{30}$ | 1X PBS | 1.5 | 66 | 66.0 | 67.2 | 1.09 |
| LF-3-103 | 200/1/0.2/1 | Glu + GOx + Pyr | BSA-[iBBr]$_{31}$ | 1X PBS | 2 | 93 | 93.3 | 84.3 | 1.17 |

*incubated in dark for 30 min

Example 5—Oxygen Fueled ATRP

Starting conditions for the polymerizations employed the following ratio of reagents: M/I/ACAC/GOx/HRP/Cu/TPMA of 200/1/1/0.0002/0.00054/0.2/1 unless a specific variation is described. The effect of ACAC concentration on the rate of polymerization is summarized in TABLE 13. Using lower equivalents of ACAC than the concentration of alkyl bromide initiator ([I]) (Entry 3) caused the reaction to proceed slowly reaching 41% conversion after 1 hour. When the amount of ACAC was equimolar to the [I] (Entry 4), the polymerization proceeded faster reaching 83% conversion in 30 minutes with dispersity similar to that reported for entry 3, Đ=1.27. Increasing the concentration of ACAC to 4× and 16× the [I] (Entries 5-6) increased the rate and reduced dispersity (Đ≤1.15).

tration of HRP less than half of GOx (100 nM, Entry 7) was not sufficient to consume the hydrogen peroxide present in the solution and create a steady flow of radicals to generate Cu (I) activators. By increasing the concentration of HRP to 270 nM (1.3× [GOx]) (Entry 8), conversion reached 58.1% in 30 minutes. However, by increasing the concentration of HRP to 567 nM (2.7× [GOx], (Entry 5) and 1130 nM (5.4× [GOx], (Entry 9), conversion reached 86.5% and 94%, respectively in 30 minutes. While plausible Fenton-like reactions may not be completely inhibited due to a lag in the catalytic activity of HRP, the experiments conducted in a completely open flask were fast and showed good correlation between theoretical $M_n$ and experimental values and low values of $M_w/M_n$. Control experiments (Entries 1-2) demonstrated that addition of both ACAC and HRP was necessary for the polymerization.

TABLE 13

Results for oxygen fueled ATRP under different conditions

| Entry[a] | M/I/ACAC | HRP (nM) | t (h) | $k_p^{app}$ (min$^{-1}$) | Conversion[b] | $M_{n,th}$[c] | $M_{n,GPC}$[d] | $M_w/M_n$[d] |
|---|---|---|---|---|---|---|---|---|
| 1 | 200/1/0 | 567 | 2.5 | — | — | — | — | — |
| 2 | 200/1/0 | — | 2.5 | — | — | — | — | — |
| 3 | 200/1/0.25 | 567 | 1 | 0.0094 | 41 | 41200 | 35300 | 1.26 |
| 4 | 200/1/1 | 567 | 0.5 | 0.0386 | 82.61 | 82800 | 65250 | 1.27 |
| 5 | 200/1/4 | 567 | 0.5 | 0.0798 | 86.5 | 86700 | 63200 | 1.15 |
| 6 | 200/1/16 | 567 | 0.5 | 0.0983 | 79.1 | 79300 | 58500 | 1.13 |
| 7 | 200/1/4 | 100 | 2.5 | — | — | — | — | — |
| 8 | 200/1/4 | 270 | 0.5 | 0.0323 | 58.1 | 58300 | 38350 | 1.13 |
| 9 | 200/1/4 | 1130 | 0.5 | 0.0951 | 94 | 94200 | 70900 | 1.17 |

[a]Reaction conditions: M = OEOMA500, [M] = 210 mM (10 vol %) in PBS, pH = 6, [Cu] = 1000 ppm, [Glucose] = 21 mM, [GOx] = 210 nM, RXN temperature = 37° C.; [I] = 1 mM;
[b]Conversion determined by $^1$H NMR.
[c]Calculated on the basis of conversion (i.e., Mn,th = BPAA + [OEOMA500]0/[BPA]0 × conversion × Mn of monomer).
[d]Determined by GPC in THF, using Mark-Houwink parameters.

Interestingly, although the difference in ACAC concentration between entries 5 and 6 is fourfold, the results obtained for the polymerization were very similar, which could indicate that the saturation limit of HRP under these conditions was reached. Consequently, the concentration of HRP was varied (Entries 5, 7-9). The changes in concentration can be more easily visualized for the comparison against GOx at concentration 210 nM. Therefore, a concen- Once that the core parameters in this enzymatic machinery were adjusted, (TABLE 14) the limits of the control provided by Cu$^{II}$/TPMA complex at lower ppm concentrations ([Cu]) versus monomer was studied. The results revealed a correlation between the amount of Cu and the $M_w/M_n$. Higher concentrations of Cu yielded better control and provided lower dispersities, while lower concentrations showed higher $M_w/M_n$ and a lower rate of reaction, as expected for ATRP. It is important to highlight that using only 100 ppm of catalyst (Entry 12) a polymer with $M_n$=33700 and Đ=1.31 in was obtained in 30 minutes. These numbers are significant, considering that the actual concentration of Cu in a 5 mL reaction mixture is 10 ppm, which approaches the concentration of Cu in drinking water.

functionalized with an ATRP initiator (e.g., 3-(triethoxysilyl)propylamine and α-bromoisobutyryl bromide for glass/silica oxide surfaces, or by direct anchoring with 12-(2-bromoisobutyramido)dodecanoic acid (BiBADA) for metal/metal oxide surfaces). Polymers were then grafted from the material surfaces. When the grafted copolymer contained a fraction of acetylethyl methacrylate (AEMA, a novel ketone containing monomer), GOx was attached to the material-polymer surface via lysine residues, through formation of an imine in the presence of a phosphate buffer under pH 8. The immobilization of GOx was reversible due to the nature of the imine linkage, and was hydrolysable under strong acidic conditions (pH 1-3). Ketone functionality could be restored, thereby reforming surfaces that were ready to be renewed for another batch of enzymes. It is noted that such immobilization also can be conducted for other enzymes (e.g., P2Ox).

TABLE 14

Results of aqueous oxygen fueled ATRP in the presence of various concentrations of Cu and targeting different $DP_n$

| Entry[a] | M/I/Cu/TPMA | Cu (ppm) | t (min) | $k_p^{app}$ (min$^{-1}$) | Conversion[b] | $M_{n,th}$[c] | $M_{n,GPC}$[d] | $M_w/M_n$[d] |
|---|---|---|---|---|---|---|---|---|
| 5 | 200/1/0.2/1 | 1000 | 30 | 0.0798 | 86.5% | 86700 | 63200 | 1.15 |
| 10 | 200/1/0.1/0.5 | 500 | 60 | 0.0408 | 81.6% | 81800 | 58600 | 1.25 |
| 11 | 200/1/0.06/0.3 | 300 | 60 | 0.0291 | 70.3% | 70500 | 49000 | 1.27 |
| 12 | 200/1/0.02/0.1 | 100 | 60 | 0.0144 | 37% | 37200 | 33700 | 1.31 |
| 13 | 50/1/0.005/0.025 | 1000 | 30 | 0.0736 | 77.9% | 19700 | 20500 | 1.14 |
| 14 | 100/1/0.01/0.05 | 1000 | 30 | 0.0876 | 81.6% | 41000 | 29400 | 1.13 |
| 15 | 150/1/0.015/0.075 | 1000 | 30 | 0.0588 | 71.8% | 54000 | 33360 | 1.15 |

[a]Reaction conditions: M = OEOMA$_{500}$, [M] = 210 mM (10 vol %) in PBS, pH = 6, [Cu] = 1000 ppm, [Glucose] = 21 mM, [GOx] = 210 nM, RXN temperature = 37° C.; [I] = 1 mM;
[b]Conversion determined by $^1$H NMR.
[c]Calculated on the basis of conversion (i.e., $M_{n,th}$ = BPAA + [OEOMA$_{500}$]$_0$/[BPA]$_0$ × conversion × $M_n$ of monomer).
[d]Determined by GPC in THF, using Mark-Houwink parameters.

Example 6—GOx Self-Deoxygenated ATRP

Figure 15:
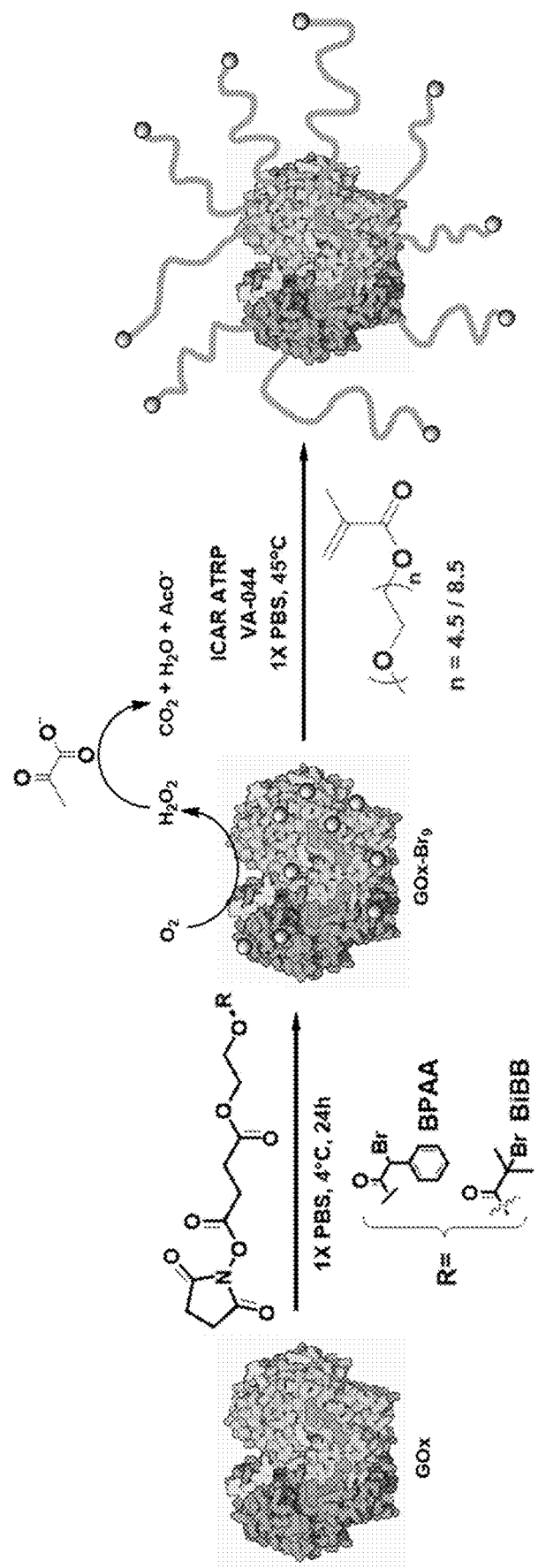
FIG. 15 is a schematic illustrating a self-deoxygenated ATRP reaction using ATRP initiator-modified GOx.

A series of Self-Deoxygenated ATRP reactions were conducted using the ATRP initiator-modified GOx. As illustrated in FIG. 15, native GOx was first modified with two versions of ATRP initiator, and then the modified GOx catalyzed deoxygenation while polymers were continuously grafted from GOx. TABLE 15 provides a list of reaction conditions of the two types of initiators and modified sites. The reaction conversion reached 70~93% within 10 minutes, yielding giving polymers with low dispersity (1.15~1.16) that were analyzed by cleaving the polymer by reaction with 5% NaOH solution for 2 hours.

TABLE 15

Results of GOx-initiator self-deoxygenated ATRP

| Entry | M/I/VA-44/Cu/Ligand | Initiator type | # initiators on Lys | RXN time (min) | Conv. (%) | $M_{n,Th} \times 10^{-3}$ | $M_{n,Corr} \times 10^{-3}$ | Đ |
|---|---|---|---|---|---|---|---|---|
| 1 | 400/1/0.3/0.2/1 | BPAA | 9 | 10 | 77 | 185 | 89.2 | 1.15 |
| 2 | 400/1/0.3/0.2/1 | BiBB | 7 | 10 | 92.5 | 154 | 60.9 | 1.16 |

M = OEOMA$_{500}$, [M] = 10 vol % in PBS, [NaBr] = 100 mM, [Glucose] = 200 mM, [Sodium Pyruvate] = 100 mM, [GOx] = 2 μM, RXN temperature = 45° C.;
Determined by GPC in THF, using Mark-Houwink parameters

Example 7—Reversible Immobilization of GOx onto Solid Surfaces

Immobilized enzymes typically are more robust and more resistant to environmental changes than free enzymes in solution. More importantly, the heterogeneity of an immobilized enzyme system can allow for easy recovery of enzymes and products, multiple reuses of enzymes, continuous manipulation of enzymatic processes, rapid termination of reactions, and a wider variety of bioreactor designs. In the present case, GOx was immobilized onto glassware or another solid support, permitting the GOx to be separated and reused, thus simplifying the reaction setup.

Figure 16:
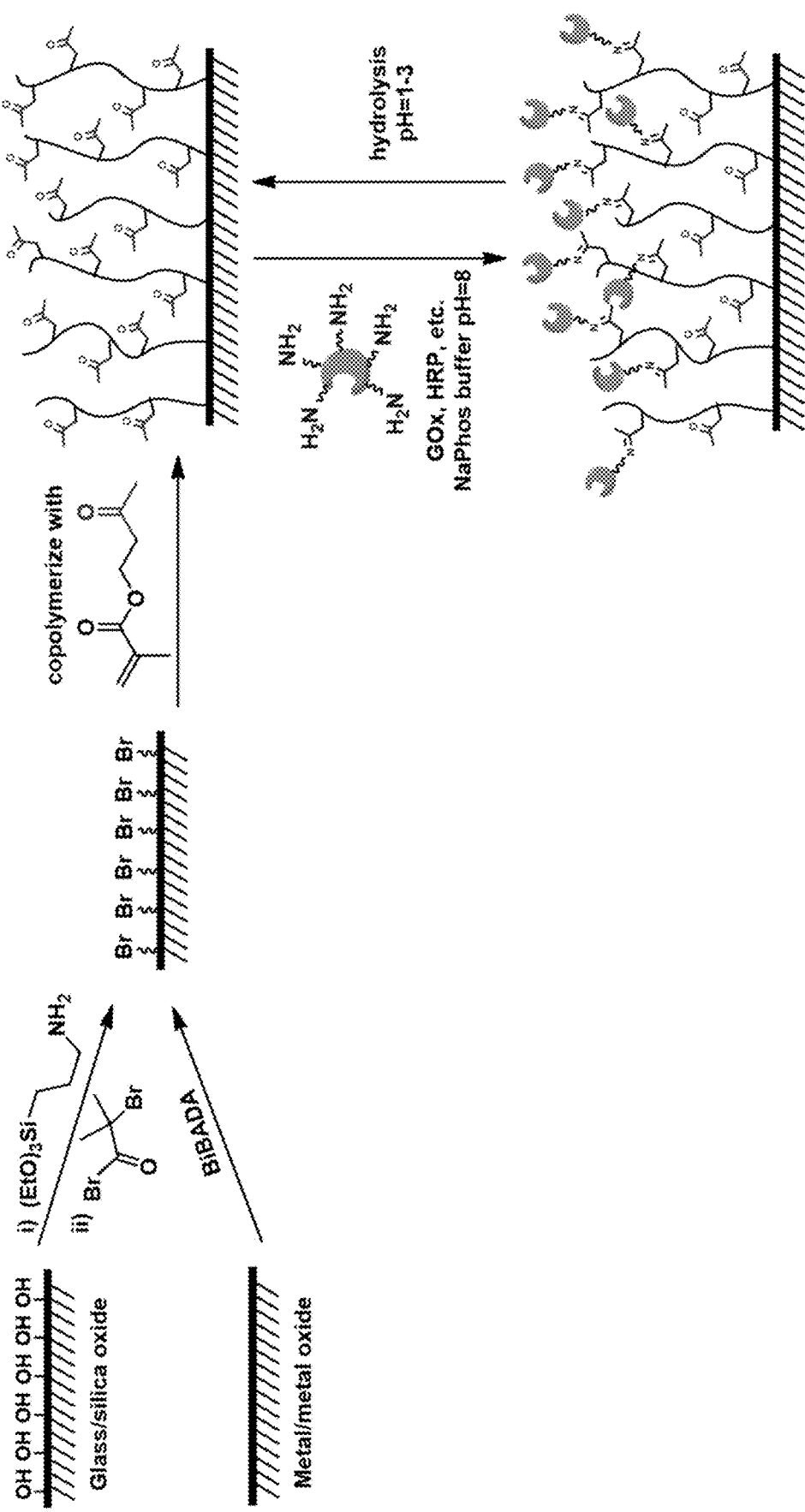
FIG. 16 is schematic illustrating the immobilization of GOx on a solid surface.

A general scheme illustrating the immobilization of GOx is illustrated in FIG. 16. A solid or material surface was

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for polymerizing free radically copolymerizable monomers, comprising combining the monomers with:
   (a) a deoxygenated, aqueous polymerization medium comprising (i) a transition metal catalyst, and (ii) an initiator comprising one or more redox transferable atoms or groups;

(b) an oxygen scavenger comprising glucose and glucose oxidase (GOx); and (c) a reactive oxygen species (ROS) scavenger comprising pyruvate, to form a conjugate.

2. The method of claim 1, wherein the method is carried out in a reactor with a limited head space comprising air.

3. The method of claim 1, wherein the method is carried out in a reactor open to the atmosphere.

4. The method of claim 1, wherein the initiator is a biomolecule with one or more functional initiators.

5. The method of claim 4, wherein the biomolecule comprises a protein, polypeptide, polynucleotide, aptamer, nucleic acid, or other biomolecule that is incorporated into the formed conjugate with the polymer grown from the incorporated initiator site(s).

6. The method of claim 1, comprising transition metal-mediated controlled polymerizing of vinyl monomers in an aqueous based polymerization medium.

7. The method of claim 1, wherein the method is an Initiators for Continuous Activator Regeneration (ICAR) atom transfer radical polymerization (ATRP), and wherein a free radical source is generated in situ by reaction of an enzyme with the product of the oxygen scavenging reaction.

8. The method of claim 1, wherein the method is a photo-ATRP, wherein a free radical source is generated in situ by photo-based reaction of a reducing agent, and wherein oxygen is removed by reaction of an enzyme with the product of the oxygen scavenging reaction.

9. The method of claim 1, wherein the method is an activator regenerated by electron transfer (ARGET) ATRP, wherein a free radical source is generated in situ by reaction of a reducing agent, and wherein oxygen is removed by reaction of an enzyme with the product of the oxygen scavenging reaction.

10. The method of claim 9, wherein the method is a surface-initiated polymerization.

11. The method of claim 1, wherein the GOx is immobilized on a solid surface.

12. The method of claim 11, wherein the solid surface comprises glass, metal, or plastic.

13. An oxygen-driven atom transfer radical polymerization (ATRP) method, wherein the method comprises combining:

(a) a deoxygenated, aqueous polymerization medium comprising (i) copper at a concentration less than 1500 ppm, wherein the copper is capable of participating in a redox reaction, and (ii) a halogen-containing initiator comprising one or more redox transferable atoms or groups;

(b) an oxygen scavenger comprising glucose and glucose oxidase (GOx); and (c) a reactive oxygen species (ROS) scavenger comprising pyruvate, wherein the concentrations of the oxygen scavenger and the ROS scavenger are sufficient to provide a continuous source of radicals for controlled polymerization from the halogen-containing initiator.

14. The method of claim 13, wherein the method is carried out in a reactor with a limited head space comprising air.

15. The method of claim 13, wherein the method is carried out in a reactor open to the atmosphere.

16. The method of claim 13, wherein the GOx is immobilized on a solid surface.

17. The method of claim 16, wherein the solid surface comprises glass, metal, or plastic.

18. A method for polymerizing free radically copolymerizable monomers to form a conjugate, comprising combining the monomers with:

(a) a deoxygenated, aqueous polymerization medium comprising (i) a transition metal catalyst and (ii) an initiator comprising one or more redox transferable atoms or groups;

(b) glucose and glucose oxidase (GOx); and (c) pyruvate, to form the conjugate.

* * * * *